(12) United States Patent
Connor

(10) Patent No.: US 12,721,539 B2
(45) Date of Patent: Sep. 1, 2026

(54) BIOMETRIC WEARABLE DEVICE (EG. SMART WATCH) WITH RADIOWAVE OR MICROWAVE ENERGY EMITTERS/TRANSMITTERS

(71) Applicant: Robert A. Connor, Wyoming, MN (US)

(72) Inventor: Robert A. Connor, Wyoming, MN (US)

(73) Assignee: Medibotics LLC, Ham Lake, MN (US)

( * ) Notice: Subject to any disclaimer, the term of this patent is extended or adjusted under 35 U.S.C. 154(b) by 0 days.

(21) Appl. No.: 19/002,583

(22) Filed: Dec. 26, 2024

(65) Prior Publication Data

US 2026/0114742 A1 Apr. 30, 2026

Related U.S. Application Data

(63) Continuation-in-part of application No. 18/775,128, filed on Jul. 17, 2024, now Pat. No. 12,405,211, and a continuation-in-part of application No. 18/885,728, filed on Sep. 15, 2024, and a continuation-in-part of application No. 18/977,824, filed on Dec. 11, 2024, now Pat. No. 12,484,815, and a continuation-in-part of application No. 18/977,825, filed on Dec. 11, 2024, which is a continuation-in-part of application No. 18/929,026, filed on Oct. 28, 2024, and a continuation-in-part of application No. 18/885,728, filed on Sep. 15, 2024, and a continuation-in-part of application No. 18/775,128, filed on Jul. 17, 2024, now Pat. No. 12,405,211, and a continuation-in-part of application No. 18/617,950, filed on Mar. 27, 2024, and a continuation-in-part of application No. 18/121,841, filed on Mar. 15, 2023, now abandoned, (Continued)

(51) Int. Cl.
*A61B 5/05* (2021.01)
*A61B 5/00* (2006.01)
*A61B 5/0507* (2021.01)
*A61B 5/145* (2006.01)

(52) U.S. Cl.
CPC ........ *A61B 5/0507* (2013.01); *A61B 5/14532* (2013.01); *A61B 5/14542* (2013.01); *A61B 5/4875* (2013.01); *A61B 5/681* (2013.01); *A61B 2560/0462* (2013.01); *A61B 2562/043* (2013.01); *A61B 2562/046* (2013.01)

(58) Field of Classification Search
CPC ........................................................ G06F 1/163
See application file for complete search history.

(56) References Cited

U.S. PATENT DOCUMENTS 6,448,788 B1 9/2002 Meaney et al.
7,371,217 B2 5/2008 Kim et al.

(Continued)

*Primary Examiner* — Rockshana D Chowdhury
*Assistant Examiner* — Douglas R Burtner

(57) ABSTRACT

A biometric wearable device is embodied in a smart watch or finger ring with radiowave or microwave energy emitters/transmitters and energy receivers to measure the level of a biometric parameter such as body oxygenation, hydration, or glucose level. The energy emitter/transmitter and the energy receiver can be parallel, nested, and/or comprise a two-dimensional array. The device can further comprise a split ring resonator located between the energy emitter/transmitter and the energy receiver.

12 Claims, 10 Drawing Sheets

Related U.S. Application Data said application No. 18/929,026 is a continuation-in-part of application No. 18/885,728, filed on Sep. 15, 2024, and a continuation-in-part of application No. 18/775,128, filed on Jul. 17, 2024, now Pat. No. 12,405,211, and a continuation-in-part of application No. 18/121,841, filed on Mar. 15, 2023, now abandoned, said application No. 18/885,728 is a continuation-in-part of application No. 18/775,128, filed on Jul. 17, 2024, now Pat. No. 12,405,211, and a continuation-in-part of application No. 18/617,950, filed on Mar. 27, 2024, and a continuation-in-part of application No. 18/121,841, filed on Mar. 15, 2023, now abandoned, said application No. 18/775,128 is a continuation-in-part of application No. 18/617,950, filed on Mar. 27, 2024, and a continuation-in-part of application No. 18/121,841, filed on Mar. 15, 2023, now abandoned, said application No. 18/617,950 is a continuation-in-part of application No. 18/121,841, filed on Mar. 15, 2023, now abandoned, which is a continuation-in-part of application No. 17/903,746, filed on Sep. 6, 2022, now abandoned, and a continuation-in-part of application No. 17/239,960, filed on Apr. 26, 2021, now abandoned, and a continuation-in-part of application No. 16/737,052, filed on Jan. 8, 2020, now Pat. No. 11,754,542, said application No. 17/903,746 is a continuation-in-part of application No. 17/239,960, filed on Apr. 26, 2021, now abandoned, and a continuation-in-part of application No. 16/737,052, filed on Jan. 8, 2020, now Pat. No. 11,754,542, and a continuation-in-part of application No. 16/568,580, filed on Sep. 12, 2019, now Pat. No. 11,478,158, said application No. 17/239,960 is a continuation-in-part of application No. 16/737,052, filed on Jan. 8, 2020, now Pat. No. 11,754,542, which is a continuation-in-part of application No. 16/568,580, filed on Sep. 12, 2019, now Pat. No. 11,478,158, and a continuation-in-part of application No. 15/963,061, filed on Apr. 25, 2018, now Pat. No. 10,772,559, and a continuation-in-part of application No. 15/725,330, filed on Oct. 5, 2017, now Pat. No. 10,607,507, and a continuation-in-part of application No. 15/431,769, filed on Feb. 14, 2017, now abandoned, and a continuation-in-part of application No. 15/294,746, filed on Oct. 16, 2016, now Pat. No. 10,627,861, said application No. 16/568,580 is a continuation-in-part of application No. 15/963,061, filed on Apr. 25, 2018, now Pat. No. 10,772,559, and a continuation-in-part of application No. 15/725,330, filed on Oct. 5, 2017, now Pat. No. 10,607,507, and a continuation-in-part of application No. 15/431,769, filed on Feb. 14, 2017, now abandoned, and a continuation-in-part of application No. 15/418,620, filed on Jan. 27, 2017, now abandoned, and a continuation-in-part of application No. 15/294,746, filed on Oct. 16, 2016, now Pat. No. 10,627,861, said application No. 15/963,061 is a continuation-in-part of application No. 14/992,073, filed on Jan. 11, 2016, now abandoned, and a continuation-in-part of application No. 14/550,953, filed on Nov. 22, 2014, now abandoned, said application No. 15/725,330 is a continuation-in-part of application No. 15/431,769, filed on Feb. 14, 2017, now abandoned, and a continuation-in-part of application No. 14/951,475, filed on Nov. 24, 2015, now Pat. No. 10,314,492, said application No. 15/431,769 is a continuation-in-part of application No. 15/294,746, filed on Oct. 16, 2016, now Pat. No. 10,627,861, and a continuation-in-part of application No. 15/206,215, filed on Jul. 8, 2016, now abandoned, and a continuation-in-part of application No. 14/992,073, filed on Jan. 11, 2016, now abandoned, and a continuation-in-part of application No. 14/330,649, filed on Jul. 14, 2014, now abandoned, said application No. 15/418,620 is a continuation-in-part of application No. 14/951,475, filed on Nov. 24, 2015, now Pat. No. 10,314,492, said application No. 15/294,746 is a continuation-in-part of application No. 14/951,475, filed on Nov. 24, 2015, now Pat. No. 10,314,492, said application No. 15/206,215 is a continuation-in-part of application No. 14/951,475, filed on Nov. 24, 2015, now Pat. No. 10,314,492, and a continuation-in-part of application No. 14/948,308, filed on Nov. 21, 2015, now abandoned, said application No. 14/992,073 is a continuation-in-part of application No. 14/562,719, filed on Dec. 7, 2014, now Pat. No. 10,130,277, and a continuation-in-part of application No. 13/616,238, filed on Sep. 14, 2012, now abandoned, said application No. 14/951,475 is a continuation-in-part of application No. 14/071,112, filed on Nov. 4, 2013, now abandoned, and a continuation-in-part of application No. 13/901,131, filed on May 23, 2013, now Pat. No. 9,536,449, said application No. 14/948,308 is a continuation-in-part of application No. 14/550,953, filed on Nov. 22, 2014, now abandoned, and a continuation-in-part of application No. 14/449,387, filed on Aug. 1, 2014, now abandoned, and a continuation-in-part of application No. 14/132,292, filed on Dec. 18, 2013, now Pat. No. 9,442,100, and a continuation-in-part of application No. 13/901,099, filed on May 23, 2013, now Pat. No. 9,254,099, said application No. 14/330,649 is a continuation-in-part of application No. 13/523,739, filed on Jun. 14, 2012, now Pat. No. 9,042,596.

(60) Provisional application No. 63/542,077, filed on Oct. 2, 2023, provisional application No. 63/279,773, filed on Nov. 16, 2021, provisional application No. 63/171,838, filed on Apr. 7, 2021, provisional application No. 62/930,013, filed on Nov. 4, 2019, provisional application No. 62/857,942, filed on Jun. 6, 2019, provisional application No. 62/814,713, filed on Mar. 6, 2019, provisional application No. 62/814,692, filed on Mar. 6, 2019, provisional application No. 62/800,478, filed on Feb. 2, 2019, provisional application No. 62/549,587, filed on Aug. 24, 2017, provisional application No. 62/439,147, filed on Dec. 26, 2016, provisional application No. 62/349,277, filed on Jun. 13, 2016, provisional application No. 62/311,462, filed on Mar. 22, 2016, provisional application No. 62/297,827, filed on Feb. 20, 2016, provisional application No. 62/245,311, filed on Oct. 23, 2015, provisional application No. 61/932,517, filed on Jan. 28, 2014.

(56) References Cited

U.S. PATENT DOCUMENTS

| | | | |
|---|---|---|---|
| 8,725,226 | B2 | 5/2014 | Isaacson |
| 8,868,149 | B2 | 10/2014 | Eisen et al. |
| 9,149,216 | B1 | 10/2015 | Eisen et al. |
| 9,314,197 | B2 | 4/2016 | Eisen et al. |

(56) References Cited

U.S. PATENT DOCUMENTS 9,498,158 B2 11/2016 Isaacson
9,582,034 B2 2/2017 von Badinski et al.
9,642,578 B2 5/2017 Newberry
9,730,622 B2 8/2017 Eisen et al.
9,861,314 B2 1/2018 Haverinen et al.
9,970,955 B1 * 5/2018 Homyk ................ A61B 5/0261
9,980,676 B2 5/2018 Newberry
10,092,225 B2 10/2018 Bharj
10,102,342 B1 10/2018 Vleugels et al.
10,139,859 B2 11/2018 von Badinski et al.
10,156,867 B2 12/2018 von Badinski et al.
10,317,200 B1 6/2019 Han et al.
10,321,860 B2 6/2019 Newberry
10,331,168 B2 6/2019 von Badinski et al.
10,349,847 B2 7/2019 Kwon et al.
10,357,165 B2 7/2019 Yoon
10,373,716 B2 8/2019 Vleugels et al.
10,401,800 B2 9/2019 Cardinali et al.
10,423,045 B2 9/2019 Roberts et al.
10,444,834 B2 10/2019 Vescovi
10,478,101 B1 11/2019 Cespedes et al.
10,496,131 B2 12/2019 von Badinski et al.
10,499,833 B2 12/2019 Li et al.
10,548,503 B2 2/2020 Bosua
10,739,820 B2 8/2020 Wang et al.
10,768,666 B2 9/2020 von Badinski et al.
10,790,054 B1 9/2020 Vleugels et al.
10,791,988 B2 10/2020 Dunki-Jacobs
10,842,429 B2 11/2020 Kinnunen et al.
10,874,314 B2 12/2020 Leabman
10,884,455 B2 1/2021 von Badinski et al.
10,893,833 B2 1/2021 Haverinen et al.
10,901,460 B2 1/2021 von Badinski et al.
10,912,500 B2 2/2021 Poeze et al.
10,952,162 B2 * 3/2021 Navarro .............. H04W 52/225
10,952,670 B2 3/2021 Mori et al.
11,031,970 B1 6/2021 Bosua
11,033,208 B1 6/2021 Bosua
11,058,317 B1 7/2021 Bosua
11,058,331 B1 7/2021 Bosua
11,063,373 B1 7/2021 Bosua
11,185,261 B2 11/2021 Saddow et al.
11,188,124 B2 11/2021 von Badinski et al.
11,188,160 B1 11/2021 Liu
11,193,923 B2 12/2021 Bosua
11,197,612 B2 12/2021 Costantine et al.
11,209,534 B2 12/2021 Leabman
11,223,383 B2 1/2022 Bosua
11,229,383 B2 1/2022 Pikov et al.
11,234,619 B2 2/2022 Bosua
11,275,453 B1 3/2022 Tham et al.
11,291,378 B2 4/2022 Laakkonen et al.
11,316,265 B2 * 4/2022 Noras .................... H01Q 1/245
11,330,997 B2 5/2022 Bosua
11,445,929 B2 9/2022 Leabman
11,462,107 B1 10/2022 Sanchez
11,479,258 B1 10/2022 Sanchez
11,510,597 B2 11/2022 Bosua
11,529,077 B1 12/2022 Bosua
11,540,599 B1 1/2023 Yokoyama et al.
11,580,300 B1 2/2023 Tham et al.
11,599,147 B2 3/2023 von Badinski et al.
11,660,228 B2 5/2023 Goff et al.
11,666,230 B1 6/2023 Piccinini et al.
11,696,698 B1 7/2023 Bosua
11,714,494 B2 8/2023 D'Amone et al.
11,733,790 B2 8/2023 Beyhs et al.
11,764,488 B2 9/2023 Bosua et al.
11,786,133 B2 10/2023 Leabman
11,802,843 B1 10/2023 Bosua
11,829,831 B1 11/2023 Ershov et al.
11,832,926 B2 12/2023 Bosua
11,850,069 B1 12/2023 Mars et al.
11,862,037 B1 1/2024 Seymore et al.
11,864,871 B2 1/2024 Kang et al.
11,868,178 B2 1/2024 von Badinski et al.
11,868,179 B2 1/2024 von Badinski et al.
11,874,701 B2 1/2024 von Badinski et al.
11,874,702 B2 1/2024 von Badinski et al.
11,892,372 B2 * 2/2024 Stowell .............. G06K 19/0672
11,895,383 B2 2/2024 Prushinskiy et al.
11,902,791 B2 2/2024 Mars et al.
11,903,689 B2 2/2024 Bosua et al.
11,911,181 B1 2/2024 Huttunen et al.
11,916,900 B2 2/2024 Mars et al.
11,925,441 B1 3/2024 Rantanen et al.
11,937,905 B2 3/2024 Singleton et al.
11,949,673 B1 4/2024 Sanchez
11,980,439 B2 5/2024 Koskela et al.
12,007,338 B2 6/2024 Bosua
12,007,727 B2 6/2024 Leith et al.
12,013,725 B2 6/2024 von Badinski et al.
12,019,034 B2 6/2024 Bosua
12,023,151 B2 7/2024 Bosua
12,029,557 B1 7/2024 Kenny et al.
12,042,258 B2 7/2024 Laakkonen et al.
12,051,858 B2 7/2024 Bosua et al.
12,074,637 B2 8/2024 Vallius et al.
12,076,142 B2 9/2024 Venugopal et al.
12,089,927 B2 9/2024 Bosua
12,092,589 B1 9/2024 Bosua
12,121,336 B2 10/2024 Leabman
12,146,841 B2 11/2024 Bosua et al.
12,156,716 B1 12/2024 Grajewski et al.
12,169,150 B2 * 12/2024 Schossmann ......... G01S 13/583
12,174,090 B2 * 12/2024 Stowell ............... G01M 5/0033
12,196,636 B2 * 1/2025 Stowell .................. G01B 15/02
12,270,785 B2 * 4/2025 Jardine ................. B60C 23/064
12,313,570 B2 * 5/2025 Jardine ................ H01Q 1/2241
12,376,754 B2 * 8/2025 Bteich .................. A61B 5/0507
12,379,339 B2 * 8/2025 Cook .................. G06Q 30/018
2005/0203387 A1 9/2005 Godshalk et al.
2008/0200790 A1 8/2008 Kim et al.
2008/0319285 A1 12/2008 Hancock
2009/0275896 A1 * 11/2009 Kamen ............... A61M 5/1413 604/151
2011/0082355 A1 4/2011 Eisen et al.
2011/0152725 A1 * 6/2011 Demir .................... A61B 5/103 600/587
2011/0263961 A1 10/2011 Craddock et al.
2012/0074313 A1 3/2012 Blick et al.
2012/0086463 A1 * 4/2012 Boybay .............. G01R 29/0878 324/149
2012/0185267 A1 * 7/2012 Kamen ................ A61B 5/0024 705/2
2012/0310055 A1 12/2012 Jean
2013/0131475 A1 5/2013 Eisen et al.
2013/0225960 A1 8/2013 Porch et al.
2013/0289370 A1 10/2013 Sun et al.
2013/0317753 A1 * 11/2013 Kamen .................. G16H 40/67 600/595
2014/0058226 A1 2/2014 Chernobro et al.
2014/0100823 A1 4/2014 Kosturko
2014/0200423 A1 7/2014 Eisen et al.
2014/0255882 A1 9/2014 Hadad et al.
2015/0018647 A1 * 1/2015 Mandel .................. A61B 5/681 600/323
2015/0105638 A1 4/2015 Eisen et al.
2015/0220109 A1 8/2015 von Badinski et al.
2015/0238125 A1 * 8/2015 Acosta .................. A61B 5/681 600/310
2015/0313496 A1 * 11/2015 Connor ................ A61B 5/6814 600/301
2016/0012749 A1 * 1/2016 Connor .............. G09B 19/0092 600/27
2016/0051171 A1 * 2/2016 Pikov .................. A61B 5/0507 600/407
2016/0146726 A1 5/2016 Aggarwal
2016/0198961 A1 * 7/2016 Homyk .................. A61B 5/681 600/476
2016/0206251 A1 7/2016 Kwon et al.
2016/0246326 A1 8/2016 von Badinski et al.
2016/0262673 A1 9/2016 Skorich et al.

(56) References Cited

U.S. PATENT DOCUMENTS

2016/0278676 A1 9/2016 Eisen et al.
2016/0292563 A1 10/2016 Park
2016/0338601 A1 11/2016 Yang
2016/0350581 A1 12/2016 Manuel et al.
2017/0071518 A1 3/2017 Xavier Da Silveira et al.
2017/0079563 A1 3/2017 Seo et al.
2017/0135600 A1* 5/2017 Chien .................. A61B 5/7207
2017/0156634 A1 6/2017 Li et al.
2017/0181658 A1 6/2017 Dettmann et al.
2017/0196493 A1 7/2017 Isaacson
2017/0209095 A1 7/2017 Wagner et al.
2017/0220772 A1 8/2017 Vleugels et al.
2017/0224263 A1 8/2017 Lobbestael et al.
2017/0231536 A1 8/2017 Bharj
2017/0231566 A1 8/2017 Klimek et al.
2017/0235332 A1 8/2017 von Badinski et al.
2017/0235933 A1 8/2017 von Badinski et al.
2017/0249445 A1 8/2017 Devries et al.
2017/0292908 A1 10/2017 Wilk et al.
2017/0303788 A1 10/2017 Xavier Da Silveira
2017/0311823 A1 11/2017 Rausch et al.
2017/0319131 A1 11/2017 Xavier Da Silveira
2017/0325742 A1 11/2017 Prior et al.
2018/0020979 A1 1/2018 Wagner et al.
2018/0042513 A1* 2/2018 Connor ................ A61B 5/0537
2018/0042554 A1 2/2018 Wagner et al.
2018/0055449 A1 3/2018 Ko et al.
2018/0070850 A1 3/2018 Stafford et al.
2018/0074010 A1 3/2018 Wang et al.
2018/0074012 A1 3/2018 Wang et al.
2018/0078209 A1 3/2018 Wagner et al.
2018/0103883 A1 4/2018 Darty et al.
2018/0103902 A1 4/2018 Haverinen et al.
2018/0123629 A1 5/2018 Wetzig
2018/0136042 A1 5/2018 Goldring et al.
2018/0140237 A1 5/2018 Rajan et al.
2018/0140238 A1 5/2018 Johnson et al.
2018/0143073 A1 5/2018 Goldring et al.
2018/0143150 A1 5/2018 Bezemer et al.
2018/0214077 A1 8/2018 Dunki-Jacobs
2018/0220906 A1 8/2018 LeBoeuf et al.
2018/0252580 A2 9/2018 Goldring et al.
2018/0271448 A1 9/2018 Bynam et al.
2018/0300458 A1 10/2018 Vleugels et al.
2018/0317786 A1 11/2018 Kulach et al.
2018/0325431 A1 11/2018 Guarin et al.
2018/0333107 A1 11/2018 Sada et al.
2019/0013368 A1 1/2019 Chung et al.
2019/0025120 A1 1/2019 Lee et al.
2019/0033130 A1 1/2019 Goldring et al.
2019/0033132 A1 1/2019 Goldring et al.
2019/0033217 A1 1/2019 Kim
2019/0041265 A1 2/2019 Rosen et al.
2019/0049296 A1 2/2019 Cho et al.
2019/0067257 A1 2/2019 Yeon et al.
2019/0069843 A1 3/2019 Chatterjee et al.
2019/0104939 A1 4/2019 Costantine et al.
2019/0104942 A1 4/2019 Peru et al.
2019/0113387 A1 4/2019 Lee et al.
2019/0117140 A1 4/2019 Al-Ali et al.
2019/0120689 A1 4/2019 Leem et al.
2019/0133469 A1 5/2019 Just et al.
2019/0142313 A1 5/2019 Abou Ismail et al.
2019/0150746 A1 5/2019 Kim
2019/0154584 A1 5/2019 Ahn et al.
2019/0155385 A1 5/2019 Lim et al.
2019/0159703 A1 5/2019 Aggarwal et al.
2019/0167170 A1 6/2019 Varsavsky et al.
2019/0167190 A1 6/2019 Choi et al.
2019/0167201 A1 6/2019 Xavier Da Silveira et al.
2019/0200883 A1 7/2019 Moon et al.
2019/0204865 A1 7/2019 von Badinski et al.
2019/0216322 A1 7/2019 Anikanov et al.
2019/0216340 A1 7/2019 Holz et al.
2019/0231237 A1 8/2019 Saddow et al.
2019/0236465 A1 8/2019 Vleugels
2019/0244541 A1 8/2019 Hadad et al.
2019/0244704 A1 8/2019 Kim et al.
2019/0246977 A1 8/2019 Miller et al.
2019/0252569 A1 8/2019 Jo et al.
2019/0290172 A1 9/2019 Hadad et al.
2019/0333634 A1 10/2019 Vleugels et al.
2019/0357800 A1 11/2019 Bosua
2019/0384354 A1 12/2019 von Badinski et al.
2019/0388000 A1 12/2019 Costantine et al.
2020/0054255 A1 2/2020 Conrad et al.
2020/0089272 A1 3/2020 von Badinski et al.
2020/0146584 A1 5/2020 Bosua
2020/0187812 A1 6/2020 Leabman
2020/0187813 A1 6/2020 Leabman
2020/0187817 A1 6/2020 Leabman
2020/0187820 A1 6/2020 Leabman
2020/0187836 A1 6/2020 Leabman
2020/0187867 A1 6/2020 Leabman
2020/0191932 A1 6/2020 Leabman
2020/0294645 A1 9/2020 Vleugels
2020/0381101 A1 12/2020 Vleugels
2020/0401183 A1 12/2020 von Badinski et al.
2021/0072833 A1 3/2021 Mutlu et al.
2021/0089126 A1 3/2021 Nickerson
2021/0186356 A1 6/2021 Bosua
2021/0186357 A1 6/2021 Bosua et al.
2021/0194531 A1 6/2021 Bosua
2021/0204815 A1 7/2021 Koskela et al.
2021/0244308 A1 8/2021 Bosua
2021/0289897 A1 9/2021 Hsu et al.
2021/0307686 A1 10/2021 Catani et al.
2021/0350920 A1 11/2021 Vleugels et al.
2022/0012467 A1 1/2022 Kuo et al.
2022/0039682 A1* 2/2022 Bteich .................. A61B 5/0507
2022/0057832 A1 2/2022 von Badinski et al.
2022/0071523 A1 3/2022 Bosua
2022/0074870 A1 3/2022 Bosua
2022/0074871 A1 3/2022 Bosua
2022/0085841 A1 3/2022 Gretarsson et al.
2022/0091683 A1 3/2022 Beyhs et al.
2022/0151553 A1 5/2022 Bosua
2022/0192494 A1 6/2022 Leabman
2022/0192511 A1 6/2022 Leabman
2022/0192531 A1 6/2022 Leabman
2022/0248984 A1 8/2022 Poeze et al.
2022/0287656 A1 9/2022 Leabman
2022/0296111 A1 9/2022 Leabman
2022/0296117 A1 9/2022 Laakkonen et al.
2022/0334639 A1 10/2022 Sanchez
2022/0383741 A1 12/2022 Sanchez
2022/0386885 A1 12/2022 Lee et al.
2022/0407550 A1 12/2022 Gretarsson et al.
2022/0409072 A1 12/2022 Kang et al.
2023/0000405 A1 1/2023 Lee et al.
2023/0007884 A1 1/2023 Kang et al.
2023/0008487 A1 1/2023 Caizzone et al.
2023/0021838 A1 1/2023 Tse et al.
2023/0034807 A1 2/2023 McDaniel et al.
2023/0043018 A1 2/2023 Wai et al.
2023/0053252 A1 2/2023 Jung
2023/0056434 A1 2/2023 Jang et al.
2023/0070636 A1 3/2023 Kang et al.
2023/0072436 A1 3/2023 Sanchez
2023/0079736 A1 3/2023 Makinen
2023/0081794 A1 3/2023 Makinen et al.
2023/0085555 A1 3/2023 Nomvar et al.
2023/0113714 A1 4/2023 Vallius et al.
2023/0118067 A1 4/2023 Chang et al.
2023/0143293 A1 5/2023 Sanchez
2023/0145527 A1 5/2023 Bosua et al.
2023/0153416 A1 5/2023 Sanchez
2023/0157562 A1 5/2023 Bosua
2023/0157645 A1 5/2023 Lee et al.
2023/0172476 A1 6/2023 Bosua et al.
2023/0174114 A1 6/2023 Sanchez
2023/0178213 A1 6/2023 Haertel et al.
2023/0190118 A1 6/2023 Park et al.
2023/0190197 A1 6/2023 Huttunen

(56) References Cited

U.S. PATENT DOCUMENTS

2023/0190201 A1 6/2023 Singleton et al.
2023/0200744 A1 6/2023 Choi et al.
2023/0205170 A1 6/2023 Sanchez
2023/0205325 A1 6/2023 Khan
2023/0213970 A1 7/2023 von Badinski et al.
2023/0218192 A1 7/2023 Eom et al.
2023/0225671 A1 7/2023 Kosman et al.
2023/0225676 A1 7/2023 Halpern et al.
2023/0233084 A1 7/2023 Moon et al.
2023/0236166 A1 7/2023 Bosua
2023/0297858 A1 9/2023 Vleugels et al.
2023/0301533 A1 9/2023 Leabman
2023/0301540 A1 9/2023 Jung et al.
2023/0309844 A1 10/2023 Jang et al.
2023/0324293 A1 10/2023 Lee
2023/0350492 A1 11/2023 Nickerson
2023/0350503 A1 11/2023 D'Amone et al.
2023/0359291 A1 11/2023 Beyhs et al.
2023/0361588 A1 11/2023 Sanchez
2023/0376071 A1 11/2023 von Badinski et al.
2023/0376072 A1 11/2023 von Badinski et al.
2023/0380692 A1 11/2023 Huttunen et al.
2023/0384827 A1 11/2023 von Badinski et al.
2023/0409080 A1 12/2023 von Badinski et al.
2024/0000328 A1 1/2024 Kangas et al.
2024/0000380 A1 1/2024 Fei et al.
2024/0000387 A1 1/2024 Leabman
2024/0008771 A1 1/2024 Bosua
2024/0011923 A1 1/2024 Bosua
2024/0012479 A1 1/2024 Qiu et al.
2024/0016405 A1 1/2024 Bosua
2024/0045473 A1 2/2024 Lee et al.
2024/0046505 A1 2/2024 Liu et al.
2024/0048675 A1 2/2024 Choi et al.
2024/0058686 A1 2/2024 Bhandarkar et al.
2024/0065631 A1 2/2024 Brooks
2024/0074681 A1 3/2024 Bosua
2024/0081663 A1 3/2024 Park et al.
2024/0112563 A1 4/2024 Norman et al.
2024/0115212 A1 4/2024 Jang et al.
2024/0122548 A1 4/2024 Kangas et al.
2024/0122550 A1 4/2024 Syrjala et al.
2024/0125915 A1 4/2024 Au et al.
2024/0126328 A1 4/2024 von Badinski et al.
2024/0126329 A1 4/2024 von Badinski et al.
2024/0126330 A1 4/2024 von Badinski et al.
2024/0126382 A1 4/2024 Yoo
2024/0134417 A1 4/2024 von Badinski et al.
2024/0138721 A1 5/2024 Eom et al.
2024/0143027 A1 5/2024 von Badinski et al.
2024/0143028 A1 5/2024 von Badinski et al.
2024/0144715 A1 5/2024 Bosua et al.
2024/0146350 A1 5/2024 Gretarsson et al.
2024/0167815 A1* 5/2024 Schossmann .......... G01B 15/06
2024/0168521 A1 5/2024 von Badinski et al.
2024/0172945 A1 5/2024 Park et al.
2024/0176425 A1 5/2024 Wang et al.
2024/0179550 A1 5/2024 Au et al.
2024/0188834 A1 6/2024 Kwon et al.
2024/0188881 A1 6/2024 Bonificio et al.
2024/0201736 A1 6/2024 von Badinski et al.
2024/0237904 A1 7/2024 Makinen et al.
2024/0241541 A1 7/2024 Makinen
2024/0285195 A1 8/2024 Lowe et al.
2024/0293084 A1 9/2024 Huttunen et al.
2024/0298966 A1 9/2024 Ariza-Zambrano et al.
2024/0310297 A1 9/2024 Cronin
2024/0310507 A1* 9/2024 Hammerschmidt .. G01S 13/751
2024/0315610 A1 9/2024 Lowe et al.
2024/0364420 A1 10/2024 Vallius et al.
2024/0374170 A1 11/2024 Cronin
2024/0396374 A1* 11/2024 Chiang ................... B60L 53/37
2026/0130604 A1* 5/2026 Chiao .................. A61B 5/0507

* cited by examiner 103
102
104
+
-
+
101

BIOMETRIC WEARABLE DEVICE (EG. SMART WATCH) WITH RADIOWAVE OR MICROWAVE ENERGY EMITTERS/TRANSMITTERS

CROSS-REFERENCE TO RELATED APPLICATIONS

This application is a continuation-in-part of U.S. patent application Ser. No. 18/977,825 filed on 2024 Dec. 11. This application is a continuation-in-part of U.S. patent application Ser. No. 18/977,824 filed on 2024 Dec. 11. This application is a continuation-in-part of U.S. patent application Ser. No. 18/929,026 filed on 2024 Oct. 28. This application is a continuation-in-part of U.S. patent application Ser. No. 18/885,728 filed on 2024 Sep. 15.

U.S. patent application Ser. No. 18/977,825 was a continuation-in-part of U.S. patent application Ser. No. 18/929,026 filed on 2024 Oct. 28. U.S. patent application Ser. No. 18/977,825 was a continuation-in-part of U.S. patent application Ser. No. 18/885,728 filed on 2024 Sep. 15. U.S. patent application Ser. No. 18/977,825 was a continuation-in-part of U.S. patent application Ser. No. 18/775,128 filed on 2024 Jul. 17. U.S. patent application Ser. No. 18/977,825 was a continuation-in-part of U.S. patent application Ser. No. 18/617,950 filed on 2024 Mar. 27. U.S. patent application Ser. No. 18/977,825 was a continuation-in-part of U.S. patent application Ser. No. 18/121.841 filed on 2023 Mar. 15.

U.S. patent application Ser. No. 18/929,026 was a continuation-in-part of U.S. patent application Ser. No. 18/885,728 filed on 2024 Sep. 15. U.S. patent application Ser. No. 18/929,026 was a continuation-in-part of U.S. patent application Ser. No. 18/775,128 filed on 2024 Jul. 17. U.S. patent application Ser. No. 18/929,026 was a continuation-in-part of U.S. patent application Ser. No. 18/121,841 filed on 2023 Mar. 15. U.S. patent application Ser. No. 18/885,728 was a continuation-in-part of U.S. patent application Ser. No. 18/775,128 filed on 2024 Jul. 17. U.S. patent application Ser. No. 18/885,728 was a continuation-in-part of U.S. patent application Ser. No. 18/617,950 filed on 2024 Mar. 27. U.S. patent application Ser. No. 18/885,728 claimed the priority benefit of U.S. provisional application 63/542,077 filed on 2023 Oct. 2. U.S. patent application Ser. No. 18/885,728 was a continuation-in-part of U.S. patent application Ser. No. 18/121,841 filed on 2023 Mar. 15.

U.S. patent application Ser. No. 18/775,128 was a continuation-in-part of U.S. patent application Ser. No. 18/617,950 filed on 2024 Mar. 27. U.S. patent application Ser. No. 18/775,128 was a continuation-in-part of U.S. patent application Ser. No. 18/121,841 filed on 2023 Mar. 15. U.S. patent application Ser. No. 18/617,950 claimed the priority benefit of U.S. provisional application 63/542,077 filed on 2023 Oct. 2. U.S. patent application Ser. No. 18/617,950 was a continuation-in-part of U.S. patent application Ser. No. 18/121,841 filed on 2023 Mar. 15. U.S. patent application Ser. No. 18/121,841 was a continuation-in-part of U.S. patent application Ser. No. 17/903,746 filed on 2022 Sep. 6. U.S. patent application Ser. No. 18/121,841 was a continuation-in-part of U.S. patent application Ser. No. 17/239,960 filed on 2021 Apr. 26. U.S. patent application Ser. No. 18/121,841 was a continuation-in-part of U.S. patent application Ser. No. 16/737,052 filed on 2020 Jan. 8.

U.S. patent application Ser. No. 17/903,746 was a continuation-in-part of U.S. patent application Ser. No. 16/568,580 filed on 2019 Sep. 12. U.S. patent application Ser. No. 17/903,746 was a continuation-in-part of U.S. patent application Ser. No. 16/737,052 filed on 2020 Jan. 8. U.S. patent application Ser. No. 17/903,746 was a continuation-in-part of U.S. patent application Ser. No. 17/239,960 filed on 2021 Apr. 26. U.S. patent application Ser. No. 17/903,746 claimed the priority benefit of U.S. provisional application 63/279,773 filed on 2021 Nov. 16. U.S. patent application Ser. No. 17/239,960 claimed the priority benefit of U.S. provisional application 63/171,838 filed on 2021 Apr. 7. U.S. patent application Ser. No. 17/239,960 was a continuation-in-part of U.S. patent application Ser. No. 16/737,052 filed on 2020 Jan. 8.

U.S. patent application Ser. No. 16/737,052 claimed the priority benefit of U.S. provisional application 62/930,013 filed on 2019 Nov. 4. U.S. patent application Ser. No. 16/737,052 claimed the priority benefit of U.S. provisional application 62/857,942 filed on 2019 Jun. 6. U.S. patent application Ser. No. 16/737,052 claimed the priority benefit of U.S. provisional application 62/814,713 filed on 2019 Mar. 6. U.S. patent application Ser. No. 16/737,052 claimed the priority benefit of U.S. provisional application 62/814,692 filed on 2019 Mar. 6. U.S. patent application Ser. No. 16/737,052 claimed the priority benefit of U.S. provisional application 62/800,478 filed on 2019 Feb. 2. U.S. patent application Ser. No. 16/737,052 was a continuation-in-part of U.S. patent application Ser. No. 16/568,580 filed on 2019 Sep. 12. U.S. patent application 16/737,052 was a continuation-in-part of U.S. patent application Ser. No. 15/963,061 filed on 2018 Apr. 25 which issued as U.S. Pat. No. 10,772,559 on 2020 Sep. 15. U.S. patent application Ser. No. 16/737,052 was a continuation-in-part of U.S. patent application Ser. No. 15/725,330 filed on 2017 Oct. 5 which issued as U.S. Pat. No. 10,607,507 on 2020 Mar. 31. U.S. patent application Ser. No. 16/737,052 was a continuation-in-part of U.S. patent application Ser. No. 15/431,769 filed on 2017 Feb. 14. U.S. patent application Ser. No. 16/737,052 was a continuation-in-part of U.S. patent application Ser. No. 15/294,746 filed on 2016 Oct. 16 which issued as U.S. Pat. No. 10,627,861 on 2020 Apr. 21.

U.S. patent application Ser. No. 16/568,580 claimed the priority benefit of U.S. provisional application 62/857,942 filed on 2019 Jun. 6. U.S. patent application Ser. No. 16/568,580 claimed the priority benefit of U.S. provisional application 62/814,713 filed on 2019 Mar. 6. U.S. patent application Ser. No. 16/568,580 claimed the priority benefit of U.S. provisional application 62/814,692 filed on 2019 Mar. 6. U.S. patent application Ser. No. 16/568,580 was a continuation-in-part of U.S. patent application Ser. No. 15/963,061 filed on 2018 Apr. 25 which issued as U.S. Pat. No. 10,772,559 on 2020 Sep. 15. U.S. patent application Ser. No. 16/568,580 was a continuation-in-part of U.S. patent application Ser. No. 15/725,330 filed on 2017 Oct. 5 which issued as U.S. Pat. No. 10,607,507 on 2020 Mar. 31. U.S. patent application Ser. No. 16/568,580 was a continuation-in-part of U.S. patent application Ser. No. 15/431,769 filed on 2017 Feb. 14. U.S. patent application Ser. No. 16/568,580 was a continuation-in-part of U.S. patent application Ser. No. 15/418,620 filed on 2017 Jan. 27. U.S. patent application Ser. No. 16/568,580 was a continuation-in-part of U.S. patent application Ser. No. 15/294,746 filed on 2016 Oct. 16 which issued as U.S. Pat. No. 10,627,861 on 2020 Apr. 21.

U.S. patent application Ser. No. 15/963,061 was a continuation-in-part of U.S. patent application Ser. No. 14/992,073 filed on 2016 Jan. 11. U.S. patent application Ser. No. 15/963,061 was a continuation-in-part of U.S. patent application Ser. No. 14/550,953 filed on 2014 Nov. 22. U.S. patent application Ser. No. 15/725,330 claimed the priority benefit of U.S. provisional application 62/549,587 filed on 2017 Aug. 24. U.S. patent application Ser. No. 15/725,330 claimed the priority benefit of U.S. provisional application 62/439,147 filed on 2016 Dec. 26. U.S. patent application Ser. No. 15/725,330 was a continuation-in-part of U.S. patent application Ser. No. 15/431,769 filed on 2017 Feb. 14. U.S. patent application Ser. No. 15/725,330 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/431,769 claimed the priority benefit of U.S. provisional application 62/439,147 filed on 2016 Dec. 26. U.S. patent application Ser. No. 15/431,769 claimed the priority benefit of U.S. provisional application 62/349,277 filed on 2016 Jun. 13. U.S. patent application Ser. No. 15/431,769 claimed the priority benefit of U.S. provisional application 62/311,462 filed on 2016 Mar. 22. U.S. patent application Ser. No. 15/431,769 was a continuation-in-part of U.S. patent application Ser. No. 15/294,746 filed on 2016 Oct. 16 which issued as U.S. Pat. No. 10,627,861 on 2020 Apr. 21. U.S. patent application Ser. No. 15/431,769 was a continuation-in-part of U.S. patent application Ser. No. 15/206,215 filed on 2016 Jul. 8. U.S. patent application Ser. No. 15/431,769 was a continuation-in-part of U.S. patent application Ser. No. 14/992,073 filed on 2016 Jan. 11. U.S. patent application Ser. No. 15/431,769 was a continuation-in-part of U.S. patent application Ser. No. 14/330,649 filed on 2014 Jul. 14.

U.S. patent application Ser. No. 15/418,620 claimed the priority benefit of U.S. provisional application 62/297,827 filed on 2016 Feb. 20. U.S. patent application Ser. No. 15/418,620 was a continuation-in-part of U.S. patent application Ser. No. 14/951,475 filed on 2015 Nov. 24 which issued as U.S. Pat. No. 10,314,492 on 2019 Jun. 11. U.S. patent application Ser. No. 15/294,746 claimed the priority benefit of U.S. provisional application 62/349,277 filed on 2016 Jun. 13. U.S. patent application Ser. No. 15/294,746 claimed the priority benefit of U.S. provisional application 62/245,311 filed on 2015 Oct. 23. U.S. patent application Ser. No. 15/294,746 was a continuation-in-part of U.S. patent application Ser. No. 14/951,475 filed on 2015 Nov. 24 which issued as U.S. Pat. No. 10,314,492 on 2019 Jun. 11.

U.S. patent application Ser. No. 15/206,215 claimed the priority benefit of U.S. provisional application 62/349,277 filed on 2016 Jun. 13. U.S. patent application Ser. No. 15/206,215 was a continuation-in-part of U.S. patent application Ser. No. 14/951,475 filed on 2015 Nov. 24 which issued as U.S. Pat. No. 10,314,492 on 2019 Jun. 11. U.S. patent application Ser. No. 15/206,215 was a continuation-in-part of U.S. patent application Ser. No. 14/948,308 filed on 2015 Nov. 21. U.S. patent application Ser. No. 14/992,073 was a continuation-in-part of U.S. patent application Ser. No. 14/562,719 filed on 2014 Dec. 7 which issued as U.S. Pat. No. 10,130,277 on 2018 Nov. 20. U.S. patent application Ser. No. 14/992,073 was a continuation-in-part of U.S. patent application Ser. No. 13/616,238 filed on 2012 Sep. 14.

U.S. patent application Ser. No. 14/951,475 was a continuation-in-part of U.S. patent application Ser. No. 14/071,112 filed on 2013 Nov. 4. U.S. patent application Ser. No. 14/951,475 was a continuation-in-part of U.S. patent application Ser. No. 13/901,131 filed on 2013 May 23 which issued as U.S. Pat. No. 9,536,449 on 2017 Jan. 3. U.S. patent application Ser. No. 14/948,308 was a continuation-in-part of U.S. patent application Ser. No. 14/550,953 filed on 2014 Nov. 22. U.S. patent application Ser. No. 14/948,308 was a continuation-in-part of U.S. patent application Ser. No. 14/449.387 filed on 2014 Aug. 1. U.S. patent application Ser. No. 14/948,308 was a continuation-in-part of U.S. patent application Ser. No. 14/132,292 filed on 2013 Dec. 18 which issued as U.S. Pat. No. 9,442,100 on 2016 Sep. 13. U.S. patent application Ser. No. 14/948,308 was a continuation-in-part of U.S. patent application Ser. No. 13/901,099 filed on 2013 May 23 which issued as U.S. Pat. No. 9,254,099 on 2016 Feb. 9. U.S. patent application Ser. No. 14/562,719 claimed the priority benefit of U.S. provisional application 61/932,517 filed on 2014 Jan. 28. U.S. patent application Ser. No. 14/330,649 was a continuation-in-part of U.S. patent application Ser. No. 13/523,739 filed on 2012 Jun. 14 which issued as U.S. Pat. No. 9,042,596 on 2015 May 26.

The entire contents of these applications are incorporated herein by reference.

FEDERALLY SPONSORED RESEARCH

Not Applicable

SEQUENCE LISTING OR PROGRAM

Not Applicable

BACKGROUND—FIELD OF INVENTION

This invention relates to wearable devices for measuring biometric parameters.

INTRODUCTION

Biometric wearable devices such as smart finger rings and smart watches have advantages over mobile handheld devices (such as cellphones) and non-mobile devices (such as stationary medical equipment) for monitoring a person's biometric parameters: to diagnosis adverse health conditions; to provide an alert in case of an adverse health event; to provide a feedback and/or control loop for the operation of implanted medical devices; and to help people maintain their health and prevent illness. Due to their consistent proximity to a person's body and their easily transportable nature, these devices can monitor biometric parameters more broadly and consistently than handheld devices. There are challenges in the development of biometric wearable devices. For example, they are relatively small, which can make it difficult for them to house complex components. It can also be challenging to scan different tissue regions and depths. However, these challenges can be addressed by some of the sensor designs using radiowave or microwave energy scanning which are disclosed herein.

REVIEW OF THE RELEVANT ART

U.S. patent application 20190142313 (Abou Ismail et al., May 16, 2019, "System and Method for Non-Invasive Continuous Real-Time Blood Glucose Monitoring") discloses using an impedance sensor and permittivity to measure blood glucose. U.S. patent application 20160146726 (Aggarwal, May 26, 2016, "Wearable Device for Detection of Contaminants and Method Thereof") discloses a wearable spectrometer for analyzing the chemical composition of substances. U.S. patent application 20190159703 (Aggarwal et al., May 30, 2019, "System and Method for Obtaining Blood Glucose Concentration Using Temporal Independent Component Analysis (ICA)") discloses using near infrared spectroscopy (NIR) to measure blood glucose.

U.S. patent application 20190154584 (Ahn et al., May 23, 2019, "Spectroscopy Apparatus, Spectroscopy Method, and Bio-Signal Measuring Apparatus") discloses a spectroscopy apparatus with a dispersive element which divides an incident light into a plurality of lights having different output angles. U.S. patent application 20190117140 (Al-Ali et al., Apr. 25, 2019, "Advanced Pulse Oximetry Sensor") discloses a pulse oximetry sensor with a light diffuser and light concentrator. U.S. patent application 20190216322 (Anikanov et al., Jul. 18, 2019, "Compact Spectrometer System for Non-Invasive Measurement of Absorption and Transmission Spectra in Biological Tissue Samples") discloses a spectrometer for analyzing an inhomogeneous scattering medium. U.S. patent application 20240298966 (Ariza-Zambrano et al., Sep. 12, 2024, "Method and System for Detecting Food Intake Events from Wearable Devices and Non-Transitory Computer-Readable Storage Medium") discloses a system and method for detecting food intake using wearable devices.

U.S. patent application 20240125915 (Au et al., Apr. 18, 2024, "Method, Apparatus, and System for Wireless Sensing Measurement and Reporting") and U.S. patent application 20240179550 (Au et al., May 30, 2024, "Method, Apparatus, and System for Wireless Sensing Measurement and Reporting") disclose methods, devices, and systems for wireless sensing including transmitting a time series of at least one wireless sounding signal (WSS). U.S. patent application 20220091683 (Beyhs et al., Mar. 24, 2022, "Ring Input Device with Pressure-Sensitive Input") and U.S. Pat. No. 11,733,790 (Beyhs et al., Aug. 22, 2023, "Ring Input Device with Pressure-Sensitive Input") disclose a ring with a pressure-sensitive input mechanism. U.S. patent application 20230359291 (Beyhs et al., Nov. 9, 2023, "Ring Input Device with Variable Rotational Resistance") discloses a ring input device with variable rotational resistance mechanisms which change the rotational friction of a rotating outer band.

U.S. patent application 20180143150 (Bezemer et al., May 24, 2018, "Apparatus and Methods That Use Magnetic Induction Spectroscopy to Monitor Tissue Fluid Content") discloses using magnetic induction spectroscopy to measure tissue fluid. U.S. patent application 20240058686 (Bhandarkar et al., Feb. 22, 2024, "Smart Wearable Device") discloses a smart ring with an electronics unit that is selectively attachable to a coupling mount. U.S. patent application 20170231536 (Bharj, Aug. 17, 2017, "Non-Invasive System and Method for Measuring Blood Glucose in the Human Body Utilizing a Modified Ceramic Coaxial Resonator") and U.S. Pat. No. 10,092,225 (Bharj, Oct. 9, 2018, "Non-Invasive System and Method for Measuring Blood Glucose in the Human Body Utilizing a Modified Ceramic Coaxial Resonator") disclose a system and method for measuring glucose levels using a modified ceramic coaxial resonator.

U.S. patent application 20120074313 (Blick et al., Mar. 29, 2012, "Microwave Cavity Detector for Mass Spectrometry") discloses a detector for time of flight mass spectroscopy using a microwave resonant cavity excited into resonance by the passage of charged particles as an ion detector. U.S. patent application 20240188881 (Bonificio et al., Jun. 13, 2024, "Wearable Ring Device and Method of Monitoring Sleep Apnea Events") discloses a finger-worn band with a pulse oximetry sensor on an inner surface of the band.

U.S. patent application 20190357800 (Bosua, Nov. 28, 2019, "Health Related Diagnostics Employing Spectroscopy in Radio/Microwave Frequency Band") and U.S. Pat. No. 10,548,503 (Bosua, Feb. 4, 2020, "Health Related Diagnostics Employing Spectroscopy in Radio/Microwave Frequency Band") disclose an automated medical diagnostic system which transmits signals into body tissue at each of a plurality of discrete frequencies (e.g., steps of 1 MHz from 300 MHz to 2500 MHz) or unequal steps. U.S. patent applications 20200146584 (Bosua, May 14, 2020, "Non-Invasive Spectroscopy in Radio/Microwave Frequency Band") and 20230157562 (Bosua, May 25, 2023, "Non-Invasive Spectroscopy in Radio/Microwave Frequency Band") disclose a medical diagnostic system which transmits signals into bodily tissue at each of a plurality of discrete frequencies (e.g., steps of 1 MHz from 300 MHz to 2500 MHz) or unequal steps.

U.S. Pat. No. 11,033,208 (Bosua, Jun. 15, 2021, "Fixed Operation Time Frequency Sweeps for an Analyte Sensor") discloses sensors that detect an analyte via spectroscopic techniques using non-optical frequencies such as in the radio or microwave frequency range of the electromagnetic spectrum. U.S. patent application 20210186357 (Bosua et al., Jun. 24, 2021, "Non-Invasive Analyte Sensor Device") and U.S. Pat. No. 11,903,689 (Bosua et al., Feb. 20, 2024, "Non-Invasive Analyte Sensor Device") disclose a non-invasive analyte sensor device that includes a sensor housing, and a decoupled antenna/detector array having at least one transmit antenna/element and at least one receive antenna/element.

U.S. patent application 20210194531 (Bosua, Jun. 24, 2021, "Non-Invasive Analyte Sensor and System with Decoupled and Inefficient Transmit and Receive Antennas") and U.S. Pat. No. 11,031,970 (Bosua, Jun. 8, 2021, "Non-Invasive Analyte Sensor and System with Decoupled and Inefficient Transmit and Receive Antennas") and U.S. Pat. No. 11,223,383 (Bosua, Jan. 11, 2022, "Non-Invasive Analyte Sensor and System with Decoupled and Inefficient Transmit and Receive Antennas") disclose a non-invasive analyte sensor system with a transmit antenna/element and a receive antenna/element, wherein the transmit antenna/element and the receive antenna/element are less than 95% (or 90% or 85% or 75%) coupled to one another. U.S. patent application 20210186356 (Bosua, Jun. 24, 2021, "Non-Invasive Detection of an Analyte Using Decoupled and Inefficient Transmit and Receive Antennas") and U.S. Pat. No. 11,058,317 (Bosua, Jul. 13, 2021, "Non-Invasive Detection of an Analyte Using Decoupled and Inefficient Transmit and Receive Antennas") disclose at least one transmit antenna/element and at least one receive antenna/element which are less than 95% coupled to one another, or less than 90% coupled to one another, or less than 85% coupled to one another, or less than 75% coupled to one another.

U.S. Pat. No. 11,058,331 (Bosua, Jul. 13, 2021, "Analyte Sensor and System with Multiple Detector Elements That Can Transmit or Receive") discloses a detector array having at least two detector elements, such as antennas or light emitting diodes, that transmit electromagnetic energy. U.S. Pat. No. 11,063,373 (Bosua, Jul. 13, 2021, "Non-Invasive Analyte Sensor and System with Decoupled Transmit and Receive Antennas") discloses transmit and receive antennas/elements which are decoupled from one another. U.S. patent application 20210244308 (Bosua, Aug. 12, 2021, "Detection of an Analyte Using Different Combinations of Detector Elements that Can Transmit or Receive") and U.S. Pat. No. 11,330,997 (Bosua, May 17, 2022, "Detection of an Analyte Using Different Combinations of Detector Elements That Can Transmit or Receive") disclose a method of analyte detection via a scan routine using a detector array that is electrically connected to a transmit circuit and electrically connected to a receive circuit, wherein the detector array has at least three detector elements.

U.S. Pat. No. 11,193,923 (Bosua, Dec. 7, 2021, "Detection of an Analyte Using Multiple Elements That Can Transmit or Receive") discloses a detector array having at least two detector elements that can emit electromagnetic waves, including selectively connecting a transmit circuit to any one or more of the at least two detector elements of the detector array. U.S. Pat. No. 11,234,619 (Bosua, Feb. 1, 2022, "Non-Invasive Detection of an Analyte Using Decoupled Transmit and Receive Antennas") discloses a transmit antenna/element having a first geometry and a receive antenna/element can having a second geometry that is geometrically different from the first geometry. U.S. patent application 20220071523 (Bosua, Mar. 10, 2022, "Non-Invasive Analyte Sensor and Automated Response System") and U.S. Pat. No. 11,510,597 (Bosua, Nov. 29, 2022, "Non-Invasive Analyte Sensor and Automated Response System") disclose the use of decoupled transmit and receive elements or antennas to transmit a signal into the medium and receive a response to the transmitted signal.

U.S. patent applications 20220074870 (Bosua, Mar. 10, 2022, "In Vitro Sensor for Analyzing In Vitro Flowing Fluids") and U.S. patent application 20220074871 (Bosua, Mar. 10, 2022, "In Vitro Sensing Methods for Analyzing In Vitro Flowing Fluids"), and also U.S. Pat. No. 12,007,338 (Bosua, Jun. 11, 2024, "In Vitro Sensor for Analyzing In Vitro Flowing Fluids") and U.S. Pat. No. 12,019,034 (Bosua, Jun. 25, 2024, "In Vitro Sensing Methods for Analyzing In Vitro Flowing Fluids") disclose apparati, systems and methods of analyzing an in vitro flowing fluid using non-optical frequencies such as in the radio or microwave frequency bands of the electromagnetic spectrum. U.S. patent application 20220151553 (Bosua, May 19, 2022, "Smartwatch with Non-Invasive Analyte Sensor") discloses a smartwatch with a non-invasive analyte sensor which uses non-optical frequencies such as in the radio or microwave frequency bands of the electromagnetic spectrum.

U.S. Pat. No. 11,529,077 (Bosua, Dec. 20, 2022, "High Performance Glucose Sensor") discloses radio or microwave frequency glucose sensor with at least two antennas, wherein at least one operates as a transmit antenna to transmit one or more of the sensing signals and one operates as a receive antenna. U.S. patent application 20230145527 (Bosua et al., May 11, 2023, "Non-Invasive Analyte Sensor with Temperature Compensation") and U.S. Pat. No. 12,146,841 (Bosua et al., Nov. 19, 2024, "Non-Invasive Analyte Sensor with Temperature Compensation") disclose a non-invasive analyte sensor with a temperature sensor. U.S. patent application 20230172476 (Bosua et al., Jun. 8, 2023, "Electromagnetic Shielding in Non-Invasive Analyte Sensors") discloses a non-invasive analyte sensor that includes an electromagnetic shield which electromagnetically isolates an electrical component of the non-invasive analyte sensor from radio frequency interference and/or microwave frequency interference.

U.S. Pat. No. 11,696,698 (Bosua, Jul. 11, 2023, "Analyte Sensors with Position Adjustable Transmit and/or Receive Components") discloses an analyte sensor that detects an analyte using frequencies in the radio or microwave frequency range, including changing an angle of a transmit component and/or receiving component. U.S. patent application 20230236166 (Bosua, Jul. 27, 2023, "Non-Invasive Analyte Sensor with Multiple Sensor Assemblies") discloses a non-invasive analyte sensor that includes first and second non-invasive analyte sensor assemblies each of which can emit transmit signals that are in a radio or microwave frequency range into a target and can detect responses resulting from emission of the transmit signals into the target.

U.S. Pat. No. 11,764,488 (Bosua et al., Sep. 19, 2023, "Methods for Determining Variability of a State of a Medium") and U.S. Pat. No. 12,051,858 (Bosua et al., Jul. 30, 2024, "Methods for Determining Variability of a State of a Medium") disclose methods for determining variability in a state of a medium, include monitoring the medium and determining the variability in the state of the medium based on the processing of a response over time. U.S. Pat. No. 11,802,843 (Bosua, Oct. 31, 2023, "Systems and Methods for Analyte Sensing with Reduced Signal Inaccuracy") discloses a system for detecting one or more analytes by generating an analyte scan that includes one or more frequencies in a radio or microwave range of the electromagnetic spectrum. U.S. Pat. No. 11,832,926 (Bosua, Dec. 5, 2023, "Non-Invasive Detection of an Analyte and Notification of Results") discloses a method for providing notification regarding one or more analytes.

U.S. patent application 20240008771 (Bosua, Jan. 11, 2024, "Systems and Methods for Analyte Sensing at Varying Body Positions") discloses analytes detected at different locations on the body by generating a transmit signal in a radio or microwave frequency. U.S. patent application 20240011923 (Bosua, Jan. 11, 2024, "Systems and Methods for Analyte Sensing of Multiple Analytes") discloses a non-invasive sensor having a plurality of antennae to detect analytes in a target, including determining a first detection frequency sweep and determining a second detection frequency sweep. U.S. patent application 20240016405 (Bosua, Jan. 18, 2024, "Detecting and Collecting Analyte Data") discloses establishing and using a analyte database from data from one or more non-invasive analyte sensors. U.S. patent application 20240074681 (Bosua, Mar. 7, 2024, "Antenna Arrays for Analyte Sensors") discloses a non-invasive analyte sensor with a first antenna with an upper surface that faces in a first direction and a third antenna with an upper surface that faces in a second direction, wherein the first direction diverges away from the second direction.

U.S. patent application 20240144715 (Bosua et al., May 2, 2024, "System and Method for Identity-Based Analyte Detection and Analysis") discloses a sensor to non-invasively detect one or more analytes in a subject based on the biological identity or a status of the subject. U.S. Pat. No. 12,023,151 (Bosua, Jul. 2, 2024, "Non-Invasive Analyte Sensing and Notification System with Decoupled Transmit and Receive Antennas") and U.S. Pat. No. 12,089,927 (Bosua, Sep. 17, 2024, "Non-Invasive Analyte Sensing and Notification System with Decoupled and Inefficient Transmit and Receive Antennas") disclose a method for providing notification regarding one or more analytes, including detecting an amount of each of the one or more analytes using a non-invasive sensor. U.S. Pat. No. 12,092,589 (Bosua, Sep. 17, 2024, "In Vitro Analyte Sensor Using One or More Detector Arrays that Operate in Radio/Microwave Frequency Bands") discloses an analyte sensor with a transmit antenna which transmits a signal in the radio or microwave frequency range and a receive antenna which detects a response resulting from transmission of the signal.

U.S. patent application 20240065631 (Brooks, Feb. 29, 2024, "Pressure Adjustment for Biometric Measurement") discloses a user device with a pressure sensor to determine whether the pressure between a user's body and the device is within a proper range. U.S. patent application 20180271448 (Bynam et al., Sep. 27, 2018, "Method of Enabling Feature Extraction for Glucose Monitoring Using Near-Infrared (NIR) Spectroscopy") discloses using near-infrared (NIR) spectroscopy to measure blood glucose. U.S. patent application 20230008487 (Caizzone et al., Jan. 12, 2023, "System and Method for Smart Rings Employing Sensor Spatial Diversity") discloses a ring for photoplethysmographic sensing which uses sensor spatial diversity to enhance the quality and the reliability of measurements. U.S. Pat. No. 10,401,800 (Cardinali et al., Sep. 3, 2019, "Indicators for Wearable Electronic Devices") discloses a wearable device with a biometric sensor and illuminated biometric status indicator.

U.S. patent application 20210307686 (Catani et al., Oct. 7, 2021, "Methods and Systems to Detect Eating") discloses methods and systems for automated eating detection comprising a continuous glucose monitor (CGM) and an accelerometer. U.S. Pat. No. 10,478,101 (Cespedes et al., Nov. 19, 2019, "Continuous Glucose Monitoring Based on Remote Sensing of Variations of Parameters of a SiC Implanted Antenna") discloses a passive antenna formed of biocompatible silicon carbide (SiC) which is permanently implanted subcutaneously. U.S. patent application 20230118067 (Chang et al., Apr. 20, 2023, "Electronic Device and Method to Measure Bioelectrical Impedance") discloses an electronic device with a plurality of electrodes, a sensor connected to the electrodes, a memory, and a processor which obtains contact impedances through the sensor. U.S. patent application 20190069843 (Chatterjee et al., Mar. 7, 2019, "Wearable Personal Information System") discloses a wearable optical device with a shield to block ambient light. U.S. patent application 20140058226 (Chernobro et al., Feb. 27, 2014, "Method and Apparatus for In Vivo Optical Measurement of Blood Glucose Concentration") discloses using differential scattering spectroscopy and Doppler microscopy to measure blood glucose.

U.S. patent application 20190049296 (Cho et al., Feb. 14, 2019, "Light Filter and Spectrometer Including the Light Filter") discloses a spectrometer with different spectrum modulation portions. U.S. patent application 20190167190 (Choi et al., Jun. 6, 2019, "Healthcare Apparatus and Operating Method Thereof") discloses a healthcare apparatus with a plurality of light sources which emit light of different wavelengths, a light detector, and a processor configured to obtain a blood glucose level. U.S. patent application 20230200744 (Choi et al., Jun. 29, 2023, "Apparatus and Method for Estimating Target Component") discloses an apparatus for estimating a target component via a spectrometer. U.S. patent application 20240048675 (Choi et al., Feb. 8, 2024, "Electronic Device and Operation Method Thereof") discloses a device with processors which obtain a rotation angle of the device and determine whether the rotation angle is greater than or equal to a reference rotation angle.

U.S. patent application 20190013368 (Chung et al., Jan. 10, 2019, "Near-Infrared Light Organic Sensors, Embedded Organic Light Emitting Diode Panels, and Display Devices Including the Same") discloses an OLED panel which is embedded with a near-infrared organic photosensor, wherein this structure enables biometric recognition. U.S. patent application 20200054255 (Conrad et al., Feb. 20, 2020, "Physiological Measurement Using Wearable Device") discloses a method for real-time, high-density physiological data collection by measuring physiological parameters during each of a plurality of measurement periods.

U.S. patent application 20190104939 (Costantine et al., Apr. 11, 2019, "Novel Non-Invasive Biological, Chemical Markers and Tracers Monitoring Device in Blood Including Glucose Monitoring Using Adaptive RF Circuits and Antenna Design") discloses a non-invasive method for measuring glucose using adaptive radio frequencies and antenna circuits. U.S. patent application 20190388000 (Costantine et al., Dec. 26, 2019, "Antenna Design for Biomarker Monitoring and Methods of Use") discloses an antenna to non-invasively detect the concentration of biomarkers comprising a first slotted arch and a second slotted arch disposed on a substrate. U.S. Pat. No. 11,197,612 (Costantine et al., Dec. 14, 2021, "Non-Invasive Biological, Chemical Markers and Tracers Monitoring Device in Blood Including Glucose Monitoring Using Adaptive RF Circuits and Antenna Design") discloses a non-invasive method for measuring glucose using adaptive RF circuits and antenna designs.

U.S. patent application 20110263961 (Craddock et al., Oct. 27, 2011, "Antenna for Investigating Structure of Human or Animal") discloses one or more antennas for transmitting and/or receiving electromagnetic energy into or from the body, each antenna comprising a slot formed in a conductive element. U.S. patent application 20240310297 (Cronin, Sep. 19, 2024, "Method to Enhance a Non-Invasive RF Analyte Detection Device") discloses a noninvasive RF analyte detection device in which an enhancement database, an integration module, a transmission module, a sending enhancement module, and a receiving enhancement module are provided. U.S. patent application 20240374170 (Cronin, Nov. 14, 2024, "System and Method for RF Analyte Measurement Guided Insulin Administration") discloses a system for measuring one or more analytes using a real-time, non-invasive radio frequency analyte detection device.

U.S. patent application 20230350503 (D'Amone et al., Nov. 2, 2023, "Ring Input Devices") and U.S. Pat. No. 11,714,494 (D'Amone et al., Aug. 1, 2023, "Ring Input Devices") disclose how a head-mountable device can be operated with a ring input device worn on a finger of a user. U.S. patent application 20180103883 (Darty et al., Apr. 19, 2018, "Systems and Methods for Measuring Tissue Oxygenation") discloses using images with different spectral bands to measure tissue oxygenation. U.S. patent application 20170181658 (Dettmann et al., Jun. 29, 2017, "300 Mhz to 3 Thz Electromagnetic Wave Sensor for Determining an Interstitial Fluid Parameter In Vivo") discloses an electromagnetic wave sensor for determining an interstitial fluid parameter using a frequency range between 300 MHz and 3 THz. U.S. patent application 20170249445 (Devries et al., Aug. 31, 2017, "Portable Devices and Methods for Measuring Nutritional Intake") discloses a nutritional intake monitoring system with biosensors.

U.S. patent application 20180214077 (Dunki-Jacobs, Aug. 2, 2018, "Meal Detection Devices and Methods") and U.S. Pat. No. 10,791,988 (Dunki-Jacobs, Aug. 2, 2018, "Meal Detection Devices and Methods") disclose using biometric sensors to detect meal intake and control a therapeutic device. U.S. Pat. No. 8,868,149 (Eisen et al., Oct. 21, 2014, "Photoplethysmography Device and Method") and U.S. Pat. No. 9,149,216 (Eisen et al., Oct. 6, 2015, "Photoplethysmography Device and Method") and U.S. patent applications 20110082355 (Eisen et al., Apr. 7, 2011, "Photoplethysmography Device and Method"), 20130131475 (Eisen et al., May 23, 2013, "Photoplethysmography Device and Method"), and 20150105638 (Eisen et al., Apr. 16, 2015, "Photoplethysmography Device and Method") disclose using photoplethysmography and dynamic light scattering for biometric measurement. U.S. Pat. No. 9,314,197 (Eisen et al., Apr. 19, 2016, "Wearable Pulse Oximetry Device") and U.S. patent application 20140200423 (Eisen et al., Jul. 17, 2014, "Wearable Pulse Oximetry Device") disclose a wrist-worn pulse oximetry device which is worn over the ulna.

U.S. Pat. No. 9,730,622 (Eisen et al., Aug. 15, 2017, "Wearable Pulse Oximetry Device") and U.S. patent application 20160278676 (Eisen et al., Sep. 29, 2016, "Wearable Pulse Oximetry Device") disclose a wearable pulse oximetry device with two light emitters with two different wavelengths. U.S. patent application 20230218192 (Eom et al., Jul. 13, 2023, "Wrist-Type Body Component Measuring Apparatus and Body Component Measuring Method Using the Same") discloses a wrist-worn band with: a first input electrode and a first output electrode disposed on an inside surface of the band; and a second input electrode and a second output electrode disposed on an outside surface of the band. U.S. patent application 20240138721 (Eom et al., May 2, 2024, "Apparatus and Method for Estimating Concentration of Analyte Component") discloses an apparatus for estimating a component level using a plurality of light sources with different central wavelengths and at least one light detector.

U.S. Pat. No. 11,829,831 (Ershov et al., Nov. 28, 2023, "Electronic System with Ring Device") discloses a wearable electronic device with a coil which is formed from metal traces. U.S. patent application 20240000380 (Fei et al., Jan. 4, 2024, "Wearable Device") discloses an annular case with an energy storage unit, an information transmission unit, and an optical identification assembly.

U.S. patent application 20180333107 (Garcia Sada et al., Nov. 22, 2018, "Non-Invasive Wearable Device, Process and Systems with Adjustable Operation") discloses a wearable device with a flexible housing and an array of sensors. U.S. patent application 20050203387 (Godshalk et al., Sep. 15, 2005, "Non-Invasive Microwave Analysis Systems") discloses a transmitter antenna situated within a coupling liquid separated from a container by a flexible membrane which transmits microwaves that scatter from the container and the liquid in the container.

U.S. Pat. No. 11,660,228 (Goff et al., May 30, 2023, "Positional Obstructive Sleep Apnea Detection System") discloses an obstructive sleep apnea detection device which uses an optical engagement surface adapted to engage a user's skin. U.S. patent application 20180136042 (Goldring et al., May 17, 2018, "Spectrometry System with Visible Aiming Beam") discloses a handheld spectrometer with a visible aiming beam. U.S. patent application 20180252580 (Goldring et al., Sep. 6, 2018, "Low-Cost Spectrometry System for End-User Food Analysis") discloses a compact spectrometer that can be used in mobile devices such as smart phones. U.S. patent application 20190033130 (Goldring et al., Jan. 31, 2019, "Spectrometry Systems, Methods, and Applications") discloses a hand held spectrometer with wavelength multiplexing. U.S. patent application 20190033132 (Goldring et al., Jan. 31, 2019, "Spectrometry System with Decreased Light Path") discloses a spectrometer with a plurality of isolated optical channels.

U.S. Pat. No. 12,156,716 (Grajewski et al., Dec. 3, 2024, "Radio Frequency Biosensor with Integrated Compensation") discloses measuring the concentration of one or more types of molecules present within a human body using an antenna mounted to a wearable device. U.S. patent applications 20220085841 (Gretarsson et al., Mar. 17, 2022, "Smart Ring") and 20220407550 (Gretarsson et al., Dec. 22, 2022, "Smart Ring") disclose a wearable device which detects inputs, gestures, and/or biometric parameters. U.S. patent application 20240146350 (Gretarsson et al., May 2, 2024, "Smart Ring") discloses a ring, band, or necklace with a pressure-sensitive mechanism that receives user input in the form of applied pressure. U.S. patent application 20180325431 (Guarin et al., Nov. 15, 2018, "Electromagnetic Wave Sensor for Determining a Hydration Status of a Body Tissue In Vivo") discloses using an electromagnetic wave sensor to measure body tissue hydration.

U.S. patent applications 20190244541 (Hadad et al., Aug. 8, 2019, "Systems and Methods for Generating Personalized Nutritional Recommendations"), 20140255882 (Hadad et al., Sep. 11, 2014, "Interactive Engine to Provide Personal Recommendations for Nutrition, to Help the General Public to Live a Balanced Healthier Lifestyle"), and 20190290172 (Hadad et al., Sep. 26, 2019, "Systems and Methods for Food Analysis, Personalized Recommendations, and Health Management") disclose methods to provide nutrition recommendations based on a person's preferences, habits, medical and activity. U.S. patent application 20230178213 (Haertel et al., Jun. 8, 2023, "Automatic Tracking of Probable Consumed Food Items") discloses a method for detecting information associated with consumed food. U.S. patent application 20230225676 (Halpern et al., Jul. 20, 2023, "Wearable Devices") discloses an wearable annular member with deformable features.

U.S. Pat. No. 10,317,200 (Han et al., Jun. 11, 2019, "Multi-Mode Sensor for Surface Orientation") discloses a wearable device with an orientation sensor and multiple pairings between light emitters and light detectors. U.S. patent application 20080319285 (Hancock, Dec. 25, 2008, "Apparatus and Method for Measuring Constituent Concentrations within a Biological Tissue Structure") discloses a first antenna coupled to a microwave energy source and arranged to transmit at least a portion of the microwave energy into the tissue structure and a second antenna arranged to receive at least a portion of the microwave energy transmitted through the tissue structure.

U.S. Pat. No. 9,861,314 (Haverinen et al., Jan. 9, 2018, "Wearable Electronic Device and Method for Manufacturing Thereof") discloses a wearable electronic device including a molded body part made of a moldable ceramic material. U.S. patent application 20180103902 (Haverinen et al., Apr. 19, 2018, "Wearable Electronic Device and Method for Manufacturing Thereof") and U.S. Pat. No. 10,893,833 (Haverinen et al., Jan. 19, 2021, "Wearable Electronic Device and Method for Manufacturing Thereof") disclose a wearable electronic device made from non-ceramic material. U.S. patent application 20190216340 (Holz et al., Jul. 18, 2019, "Sensor Device") discloses a multi-dimensional optical sensor for biometric measurements. U.S. patent application 20210289897 (Hsu et al., Sep. 23, 2021, "Smart Ring") discloses a smart ring with an antenna chip and a metal ring which functions as an antenna.

U.S. patent application 20230190197 (Huttunen, Jun. 22, 2023, "Adjustable Sensor in Wearable Device") discloses a wearable device with an adjustment mechanism which moves a sensor component. U.S. patent application 20230380692 (Huttunen et al., Nov. 30, 2023, "Optimized Structures for Optical Measurement") discloses a wearable device with components which block stray light from an optical sensing path. U.S. Pat. No. 11,911,181 (Huttunen et al., Feb. 27, 2024, "Flexible Wearable Ring Device") discloses a wearable device made from flexible materials. U.S. patent application 20240293084 (Huttunen et al., Sep. 5, 2024, "Flexible Wearable Ring Device") discloses a flexible wearable device that is elastically deformable.

U.S. Pat. No. 8,725,226 (Isaacson, May 13, 2014, "Optical Sensor Path Selection") discloses a device with multiple possible pairings of light emitters and detectors to scan different tissue depths for biometric measurement. U.S. Pat. No. 9,498,158 (Isaacson, Nov. 22, 2016, "Optical Sensor Path Selection") discloses a device with multiple light emitters to scan different tissue depths for biometric measurement. U.S. patent application 20170196493 (Isaacson, Jul. 13, 2017, "Optical Sensor Path Selection") discloses a device with multiple optical elements and detectors to measure a biometric parameter. U.S. patent applications 20230056434 (Jang et al., Feb. 23, 2023, "Apparatus and Method for Estimating Blood Pressure") and 20230070636 (Kang et al., Mar. 9, 2023, "Apparatus and Method for Estimating Blood Pressure") disclose an apparatus for estimating blood pressure using a pulse wave sensor.

U.S. patent applications 20230309844 (Jang et al., Oct. 5, 2023, "Apparatus and Method for Estimating Blood Pressure") and 20240172945 (Park et al., May 30, 2024, "Apparatus and Method for Estimating Blood Pressure") disclose an apparatus and method for estimating blood pressure using a photoplethysmogram (PPG) sensor. U.S. patent application 20240115212 (Jang et al., Apr. 11, 2024, "Apparatus and Method for Estimating Physiological Variables") discloses an apparatus for estimating physiological variables using sensors and a neural-network-based physiological variable estimation model. U.S. patent application 20120310055 (Jean, Dec. 6, 2012, "Ultra-Wide Band Non-Invasive Biological Sensor and Method") discloses an electromagnetic (EM) sensor system and method that permits rapid and non-invasive measurement of blood glucose or other biological characteristics that exhibits a unique spectral signature, such as its complex electrical permittivity within the frequency range from near DC to microwave frequencies.

U.S. patent application 20190252569 (Jo et al., Aug. 15, 2019, "Near-Infrared Light Sensors Including 2-Dimensional Insulator") discloses a near infrared light sensor with a 2D material semiconductor layer on a substrate. U.S. patent application 20180140238 (Johnson et al., May 24, 2018, "Regional Oximetry Sleeve for Mobile Device") discloses a mobile computing device with a sleeve. U.S. patent application 20230053252 (Jung, Feb. 16, 2023, "Electronic Device Adjusting Oxygen Saturation and Method for Controlling the Same") discloses a device with a first sensor which detects movement and a second sensor which measures oxygen saturation. U.S. patent application 20230301540 (Jung et al., Sep. 28, 2023, "Apparatus and Method of Measuring Bio Signal") discloses a method of measuring a biosignal by positioning electrodes and switching an impedance measurer.

U.S. patent application 20190133469 (Just et al., May 9, 2019, "Physiological Monitoring Devices Having Sensing Elements Decoupled from Body Motion") discloses a biometric measuring device with multiple bands to reduce motion artifacts. U.S. patent application 20220409072 (Kang et al., Dec. 29, 2022, "Apparatus and Method for Estimating Bio-Information") discloses an apparatus to estimate biometric parameters using a pulse wave sensor with channels in an isotropic shape. U.S. patent application 20230007884 (Kang et al., Jan. 12, 2023, "Apparatus and Method for Estimating Bio-Information") discloses an apparatus to estimate biometric parameters which measures pulse wave signals from an object. U.S. Pat. No. 11,864,871 (Kang et al., Jan. 9, 2024, "Wearable Device and Method of Measuring Bio-Signal") discloses an external light collector, an auxiliary light source, and a light receiver.

U.S. patent application 20240000328 (Kangas et al., Jan. 4, 2024, "Asymmetric Sensors for Ring Wearable") discloses a wearable device with a first light-emitting component at a first radial position and a second light-emitting component at a second radial position. U.S. patent application 20240122548 (Kangas et al., Apr. 18, 2024, "Techniques for Adaptive Sensors of a Wearable Device") discloses selecting one or more optical channels in a wearable device based on a comparison of measurement quality and power consumption metrics. U.S. Pat. No. 12,029,557 (Kenny et al., Jul. 9, 2024, "Radio Frequency Antenna for Wearable Device") discloses measuring the concentration of one or more types of molecules present within a human body using radio frequency signals. U.S. patent application 20230205325 (Khan, Jun. 29, 2023, "Wearable Apparatus and Control Method Thereof") discloses a wearable apparatus with a display, a strap, at least one sensor configured to acquire posture information, and at least one processor.

U.S. Pat. No. 7,371,217 (Kim et al., May 13, 2008, "Device for the Non-Invasive Measurement of Blood Glucose Concentration by Millimeter Waves and Method Thereof") discloses a device and method for the non-invasive measurement of blood glucose concentrations by millimeter waves. U.S. patent application 20080200790 (Kim et al., Aug. 21, 2008, "Apparatus for Measuring Blood Sugar and Apparatus for Monitoring Blood Sugar Comprising the Same") discloses an apparatus for measuring blood sugar with a probe for irradiating and receiving a microwave. U.S. patent application 20190033217 (Kim, Jan. 31, 2019, "Spectrum Measurement Apparatus and Spectrum Measurement Method") discloses a spectrum measurement apparatus with a plurality of light sources which emit light at different wavelengths, a light detector, and a processor. U.S. patent application 20190150746 (Kim, May 23, 2019, "Bio-Information Measuring Apparatus and Bio-Information Measuring Method") discloses a biometric spectroscopy device with a pressure sensor. U.S. patent application 20190244704 (Kim et al., Aug. 8, 2019, "Dietary Habit Management Apparatus and Method") discloses a dietary habit management apparatus using biometric measurements.

U.S. Pat. No. 10,842,429 (Kinnunen et al., Nov. 24, 2020, "Method and System for Assessing a Readiness Score of a User") discloses a method and a system for assessing the readiness of a user based on their movements. U.S. patent application 20170231566 (Klimek et al., Aug. 17, 2017, "Tissue Interface") discloses a garment with a sensor module for biometric measurement. U.S. patent application 20180055449 (Ko et al., Mar. 1, 2018, "Wearable Measurement Apparatus") discloses a wearable biometric device with elastic portions. U.S. patent application 20210204815 (Koskela et al., Jul. 8, 2021, "An Optical Sensor System of a Wearable Device, A Method for Controlling Operation of an Optical Sensor System and Corresponding Computer Program Product") discloses a wearable optical sensor system including at least two photo transmitters, a photoreceiver, receiving electronics, and a microcontroller. U.S. Pat. No. 11,980,439 (Koskela et al., May 14, 2024, "Optical Sensor System of a Wearable Device, A Method for Controlling Operation of an Optical Sensor System and Corresponding Computer Program Product") discloses a system comprising at least two photo transmitters, a photoreceiver, receiving electronics, and a microcontroller.

U.S. patent application 20230225671 (Kosman et al., Jul. 20, 2023, "Wearable Health Apparatus for the Collection of Wellness Data and Providing Feedback Therefrom to the Wearer") discloses a ring with replaceable outer shells, as well as hardware and software that allow the user to communicate with a cell phone, cloud provider, table, personal computer or AI assistant. U.S. patent application 20140100823 (Kosturko, Apr. 10, 2014, "Systems and Methods for Spectroscopic Measurement of a Characteristic of Biological Tissue") discloses a method and system for spectroscopic measurement of a characteristic of a biological tissue using at least one light source. U.S. patent application 20180317786 (Kulach et al., Nov. 8, 2018, "Pulse Spectroscopy") discloses a wearable photoplethysmogram (PPG) sensor.

U.S. patent application 20220012467 (Kuo et al., Jan. 13, 2022, "Multi-Sensor Analysis of Food") discloses a method for estimating food composition by 3D imaging and millimeter-wave radar. U.S. patent application 20160206251 (Kwon et al., Jul. 21, 2016, "Apparatus for Detecting Bio-Information") and U.S. Pat. No. 10,349,847 (Kwon et al., Jul. 6, 2019, "Apparatus for Detecting Bio-Information") disclose an apparatus with a light-emitting diode (LED), a laser diode (LD), and an optical detector. U.S. Pat. No. 10,349,847 (Kwon et al., Jul. 6, 2019, "Apparatus for Detecting Bio-Information") and U.S. patent application 20160206251 (Kwon et al., Jul. 21, 2016, "Apparatus for Detecting Bio-Information") disclose using a two-dimensional optical array to measure biometric parameters. U.S. patent application 20240188834 (Kwon et al., Jun. 13, 2024, "Apparatus and Method for Measuring Blood Pressure") discloses an apparatus for estimating blood pressure using a pulse wave sensor.

U.S. patent application 20220296117 (Laakkonen et al., Sep. 22, 2022, "Apparatus and Method for Measuring Photoplethysmogram") and U.S. Pat. No. 11,291,378 (Laakkonen et al., Apr. 5, 2022, "Apparatus and Method for Measuring Photoplethysmogram") and U.S. Pat. No. 12,042,258 (Laakkonen et al., Jul. 23, 2024, "Apparatus and Method for Measuring Photoplethysmogram") disclose a wearable smart for photoplethysmogram measurement.

U.S. patent application 20200187836 (Leabman, Jun. 18, 2020, "Methods for Monitoring a Blood Glucose Level in a Person Using Radio Waves") discloses a method for monitoring a person's blood glucose level by transmitting millimeter range radio waves over a three-dimensional (3D) space below the person's skin surface. U.S. patent application 20200187867 (Leabman, Jun. 18, 2020, "Methods for Radio Wave Based Health Monitoring that Involve Determining an Alignment") discloses a two-dimensional array of receive antennas. U.S. patent application 20200187817 (Leabman, Jun. 18, 2020, "Removable Smartphone Case for Radio Wave Based Health Monitoring that Includes an Alignment Feature") discloses a removable smartphone case including a radio frequency (RF) front-end and an antenna array.

U.S. patent application 20200191932 (Leabman, Jun. 18, 2020, "Stepped Frequency Radar Systems with Multiple RF Units") discloses a stepped frequency radar system with a two-dimensional array of radio frequency (RF) units, wherein each RF unit is configured to implement stepped frequency scanning. U.S. patent application 20200187820 (Leabman, Jun. 18, 2020, "Systems and Methods for Radio Wave Based Health Monitoring that Involve a Strap to be Worn by a Person") discloses a wearable strap with a radio frequency (RF) front-end, a transmit antenna configured to transmit radio waves below the skin surface of a person, and a two-dimensional array of receive antennas.

U.S. patent applications 20200187812 (Leabman, Jun. 18, 2020, "Systems for Health Monitoring Using Radio Waves that Include Mixing Signals at Different Frequencies") and 20200187813 (Leabman, Jun. 18, 2020, "Systems for Health Monitoring Using Radio Waves that Include Signal Isolation") disclose a device for monitoring a health parameter including a semiconductor substrate, at least one transmit antenna configured to transmit millimeter range radio waves over a 3D space below the skin surface of a person, and multiple receive antennas configured to receive radio waves. U.S. Pat. No. 10,874,314 (Leabman, Dec. 29, 2020, "Methods for Multi-Band Radar Based Sensing") discloses devices, systems, and methods for multi-band radar sensing. U.S. Pat. No. 11,209,534 (Leabman, Dec. 28, 2021, "Methods for Operating Stepped Frequency Radar Systems with Spectral Agility") discloses a method for operating a stepped frequency radar system.

U.S. patent applications 20220192494 (Leabman, Jun. 23, 2022, "Method for Generating Training Data for Use in Monitoring the Blood Glucose Level of a Person That Utilizes a Pulse Wave Signal Generated from Radio Frequency Scanning") and U.S. patent application 20220192531 (Leabman, Jun. 23, 2022, "Method for Monitoring a Health Parameter of a Person That Utilizes Machine Learning and a Pulse Wave Signal Generated from Radio Frequency Scanning") disclose a method of receiving a pulse wave signal from radio frequency scanning data that corresponds to radio waves that have reflected from below the skin surface of a person. U.S. patent application 20220192511 (Leabman, Jun. 23, 2022, "System for Monitoring a Health Parameter of a Person That Involves Producing a Pulse Wave Signal from a Radio Frequency Front-End") discloses a radar system for a wearable health monitoring device with a radio frequency (RF) front-end including at least one transmit antenna and a two-dimensional array of receive antennas.

U.S. patent application 20220287656 (Leabman, Sep. 15, 2022, "Wearable Device That Includes an Optical Sensor System and an RF Sensor System") discloses an optical sensor system configured to generate blood pressure data, a backside RF sensor system having an RF front-end including at least one transmit antenna and a two-dimensional array of receive antennas. U.S. Pat. No. 11,445,929 (Leabman, Sep. 20, 2022, "Systems for Radio Wave Based Health Monitoring That Utilize Amplitude and Phase Data") discloses a system for monitoring a health parameter with a frequency synthesizer configured to generate radio waves across a range of stepped frequencies. U.S. patent application 20220296111 (Leabman, Sep. 22, 2022, "Method for Operating a Wearable Device That Includes an Optical Sensor System and an RF Sensor System") discloses a method involving generating blood pressure data from an optical sensor system of a wearable device and a pulse wave signal from an RF sensor system of the wearable device.

U.S. patent application 20230301533 (Leabman, Sep. 28, 2023, "Systems for Health Monitoring Using Radio Waves That Include Collocated RF Components") discloses a device for monitoring a health parameter with a semiconductor substrate including at least one transmit component and multiple receive components. U.S. Pat. No. 11,786,133 (Leabman, Oct. 17, 2023, "System for Monitoring a Health Parameter of a Person Utilizing a Pulse Wave Signal") discloses a system for monitoring a health parameter via radio waves that have reflected from below the skin surface of a person. U.S. patent application 20240000387 (Leabman, Jan. 4, 2024, "Finger Wearable Health Monitoring Device") discloses a finger wearable health monitoring device with a circular metal shell comprising a strip of metal that includes an outer surface and an inner surface and two opposing ends. U.S. Pat. No. 12,121,336 (Leabman, Oct. 22, 2024, "Method for Monitoring a Physiological Parameter in a Person That Involves Coherently Combining Data Generated from an RF-Based Sensor System") discloses a method of transmitting radio waves below the skin surface of a person and across a range of radio frequencies.

U.S. patent application 20180220906 (LeBoeuf et al., Aug. 9, 2018, "Physiological Monitoring Apparatus and Networks") discloses ear-worn devices for biometric and environmental monitoring. U.S. patent application 20190025120 (Lee et al., Jan. 24, 2019, "Spectrometer and Spectrum Measurement Method Utilizing Same") discloses a spectrometer with a first unit spectral filter which absorbs or reflects light in a part of a wavelength band of a light spectrum of an incident target, a second unit spectral filter which absorbs or reflects light in a wavelength band different from the part of the wavelength band, a first light detector configured to detect a first light spectrum passing through the first unit spectral filter, a second light detector configured to detect a second light spectrum passing through the second unit spectral filter, and a processing unit.

U.S. patent application 20190113387 (Lee et al., Apr. 18, 2019, "Spectrometric Sensor Control Method and Electronic Device for Supporting Same") discloses spectroscopic sensor with multiple wavelength bands. U.S. patent application 20220386885 (Lee et al., Dec. 8, 2022, "Wearable Electronic Device Measuring Blood Pressure and Method for Operating The Same") discloses a wearable electronic device with a memory, a first sensor, a second sensor, and a processor. U.S. patent application 20230000405 (Lee et al., Jan. 5, 2023, "Apparatus and Method for Estimating Bio-Information Based on Bio-Impedance") discloses an apparatus to estimate biometric parameters using an impedance sensor, including a pair of input electrodes and a pair of receiving electrodes.

U.S. patent application 20230157645 (Lee et al., May 25, 2023, "Apparatus and Method for Estimating Bio-Information") discloses an apparatus to estimate biometric parameters using a spectrometer. U.S. patent application 20230324293 (Lee, Oct. 12, 2023, "Apparatus and Method for Estimating Body Water Status") discloses an apparatus for estimating body hydration level with a near-infrared light spectrometer. U.S. patent application 20240045473 (Lee et al., Feb. 8, 2024, "Electronic Device and Method for Operating Electronic Device") discloses an electronic device with movable housings, at least one sensor, and one or more electromagnets. U.S. patent application 20190120689 (Leem et al., Apr. 25, 2019, "Combination Sensors and Electronic Devices") discloses a biometric device with stacked infrared sensors.

U.S. Pat. No. 12,007,727 (Leith et al., Jun. 11, 2024, "Watch Band with Fit Detection") discloses a watch band with an adjustable capacitor whose capacitance changes when the watch band configuration changes. U.S. patent application 20170156634 (Li et al., Jun. 8, 2017, "Wearable Device and Method for Monitoring Eating") and U.S. Pat. No. 10,499,833 (Li et al., Dec. 10, 2019, "Wearable Device and Method for Monitoring Eating") disclose a wearable device with an acceleration sensor to monitor eating. U.S. patent application 20190155385 (Lim et al., May 23, 2019, "Smart Ring Providing Multi-Mode Control in a Personal Area Network") discloses a smart ring which provides multi-mode control in a personal area network.

U.S. Pat. No. 11,188,160 (Liu, Nov. 30, 2021, "Wireless Controlling System Implemented with Smart Ring and Wireless Controlling Method Thereof") a wireless controlling system including a smart ring and an identification program installed in a mobile device. U.S. patent application 20240046505 (Liu et al., Feb. 8, 2024, "Electronic Device and Method with Pose Prediction") discloses an electronic device for predicting a pose and a method for operating the electronic device. U.S. patent application 20170224263 (Lobbestael et al., Aug. 10, 2017, "Tissue Site Detection") discloses an optical biometric sensor which identifies a particular tissue site. U.S. patent application 20240285195 (Lowe et al., Aug. 29, 2024, "Non-Invasive Analyte Sensor with Motion and/or Temperature Sensor") discloses a non-invasive analyte sensor with motion sensors and/or temperature sensors. U.S. patent application 20240315610 (Lowe et al., Sep. 26, 2024, "High Performance Non-Invasive Analyte Sensor") discloses a highly accurate and safe analyte sensor that detects an analyte by transmitting and receiving sensing signals in a radio or microwave frequency range of the electromagnetic spectrum.

U.S. patent applications 20230079736 (Makinen, Mar. 16, 2023, "Wearing Detection Techniques for Wearable Devices") and 20230081794 (Makinen et al., Mar. 16, 2023, "Wearing Detection Techniques for Wearable Devices") disclose a method of directing light from a light source to a light detector using an optical light guide of an wearable device. U.S. patent application 20240237904 (Makinen et al., Jul. 18, 2024, "Techniques for Measurement Path Multiplexing for a Wearable Device") discloses methods, systems, and devices for measurement multiplexing for a wearable device including selecting a transmission angle from a set of transmission angles and a reception angle from a set of reception angles based on signal quality comparison. U.S. patent application 20240241541 (Makinen, Jul. 18, 2024, "Optical Components and Assembly Techniques") discloses a manufacturing system for assembling optical components onto an inner circumference of a wearable ring.

U.S. patent application 20160350581 (Manuel et al., Dec. 1, 2016, "Smart Ring with Biometric Sensor") discloses a ring comprising a ring body and a biometric sensor. U.S. Pat. No. 11,850,069 (Mars et al., Dec. 26, 2023, "Wearable Device and Methods of Manufacturing") discloses a smart ring with a battery, a PCB, a fingerprint sensor, a temperature sensor, a memory, and a processing unit. U.S. Pat. No. 11,902,791 (Mars et al., Feb. 13, 2024, "Reader Device with Sensor Streaming Data and Methods") discloses an access control system with a controller having an antenna interface to broadcast identifying data. U.S. Pat. No. 11,916,900 (Mars et al., Feb. 27, 2024, "Authorized Remote Control Device Gesture Control Methods and Apparatus") discloses a method for controlling a remote control device which includes capturing biometric data.

U.S. patent application 20230034807 (McDaniel et al., Feb. 2, 2023, "Systems and Methods Including a Device for Personalized Activity Monitoring Involving the Hands") discloses a wearable device for activity monitoring involving the use of hands. U.S. Pat. No. 6,448,788 (Meaney et al., Sep. 10, 2002, "Fixed Array Microwave Imaging Apparatus and Method") discloses a method and apparatus for microwave imaging of an inhomogeneous target, in particular of biological tissue, which compensates for the interactions between active antennae and nonactive antennae. U.S. patent application 20190246977 (Miller et al., Aug. 15, 2019, "Optical Sensor for Wearable Devices") discloses methods, systems, apparatuses, and/or devices which emit light into a body, receive light from a depth below a surface of the body, and determine a physiological condition of the body. U.S. patent application 20190200883 (Moon et al., Jul. 4, 2019, "Bio-Signal Measuring Apparatus and Operating Method Thereof") discloses a bio-signal measuring apparatus with a photodetector and an array of light sources around the photodetector.

U.S. patent application 20230233084 (Moon et al., Jul. 27, 2023, "Method and Apparatus for Correcting Error of Optical Sensor, and Apparatus for Estimating Biometric Information") discloses a method of correcting an optical sensor error by adjusting the brightness of a light source. U.S. Pat. No. 10,952,670 (Mori et al., Mar. 23, 2021, "Meal Detection Method, Meal Detection System, and Storage Medium") discloses meal detection by analyzing arm motion data and heart rate data. U.S. patent application 20210072833 (Mutlu et al., Mar. 11, 2021, "Self-Mixing Interferometry-Based Gesture Input System Including a Wearable or Handheld Device") discloses a device with one or more SMI sensors which emit beams of electromagnetic radiation, wherein each beam is emitted in a different direction.

U.S. Pat. No. 9,642,578 (Newberry, May 9, 2017, "System and Method for Health Monitoring Using a Non-Invasive, Multi-Band Biosensor") and U.S. Pat. No. 9,980,676 (Newberry, May 29, 2018, "System and Method for Health Monitoring Using a Non-Invasive, Multi-Band Biosensor") disclose a PPG sensor which uses multiple wavelengths. U.S. Pat. No. 10,321,860 (Newberry, Jun. 18, 2019, "System and Method for Glucose Monitoring") discloses a glucose biosensor with optical fibers. U.S. patent application 20210089126 (Nickerson, Mar. 25, 2021, "Smart Ring") discloses a smart ring with a capacitive touch sensor. U.S. patent application 20230350492 (Nickerson, Nov. 2, 2023, "Smart Ring") discloses a smart ring worn which is controlled based on its position.

U.S. patent application 20230085555 (Nomvar et al., Mar. 16, 2023, "A Non-Invasive Continuous Blood Glucose Monitor") discloses a non-invasive device for measuring glucose levels. U.S. patent application 20240112563 (Norman et al., Apr. 4, 2024, "Bluetooth Enabled Smart Ring") discloses a smart ring device with wireless communication with a computing device that transitions between one or more states based on user and/or device inputs. U.S. patent application 20160292563 (Park, Oct. 6, 2016, "Smart Ring") discloses systems and methods for pairing a smart ring with a primary device. U.S. patent application 20230190118 (Park et al., Jun. 22, 2023, "Apparatus and Method for Estimating Blood Pressure") discloses an apparatus for estimating blood pressure which extracts a cardiac output feature, a first candidate total peripheral resistance feature, and a second candidate peripheral resistance feature.

U.S. patent application 20240081663 (Park et al., Mar. 14, 2024, "Apparatus for Estimating Bio-Information and Method of Detecting Abnormal Bio-Signal") discloses an apparatus with a photoplethysmogram (PPG) sensor. U.S. patent application 20190104942 (Peru et al., Apr. 11, 2019, "Spectroscopic System and Method Therefor") discloses probe which analyzes saliva for biometric measurement. U.S. Pat. No. 11,666,230 (Piccinini et al., Jun. 6, 2023, "Electronic Device and Method for Noninvasive, Continuous Blood Pressure Monitoring") discloses an electronic device and method for continuous noninvasive blood pressure monitoring.

U.S. patent application 20160051171 (Pikov et al., Feb. 25, 2016, "Methods and Systems for Non-Invasive Measurement of Blood Glucose Concentration by Transmission of Millimeter Waves Through Human Skin") and U.S. Pat. No. 11,229,383 (Pikov et al., Jan. 25, 2022, "Methods and Systems for Non-Invasive Measurement of Blood Glucose Concentration by Transmission of Millimeter Waves Through Human Skin") disclose a device for interrogating human skin using tight coupling between the transmitter and receiver of the millimeter waves (MMWs). U.S. Pat. No. 10,912,500 (Poeze et al., Feb. 9, 2021, "Multi-Stream Data Collection System for Noninvasive Measurement of Blood Constituents") discloses noninvasive methods, devices, and systems for measuring various blood constituents or analytes, such as glucose.

U.S. patent application 20220248984 (Poeze et al., Aug. 11, 2022, "User-Worn Device for Noninvasively Measuring a Physiological Parameter of a User") discloses noninvasive methods, devices, and systems for measuring various blood constituents or analytes via LEDs and super-luminescent LEDs. U.S. patent application 20130225960 (Porch et al., Aug. 29, 2013, "In-Vivo Monitoring with Microwaves") discloses a microwave resonator having a resonant response to input microwaves, wherein this response is affected by a living body in proximity or contact with the resonator. U.S. patent application 20170325742 (Prior et al., Nov. 16, 2017, "Universal Fingertip Sensor") discloses a finger-tip-worn optical biometric sensor device. U.S. Pat. No. 11,895,383 (Prushinskiy et al., Feb. 6, 2024, "Electronic Device Including Optical Sensor") discloses an electronic device with a housing which is rotatably arranged and an optical sensor assembly.

U.S. patent application 20240012479 (Qiu et al., Jan. 11, 2024, "Ring Enabling Its Wearer to Enter Control Commands") discloses systems and methods, including a smart ring, which enable a user to control electronic devices in a local network. U.S. patent application 20180140237 (Rajan et al., May 24, 2018, "Device and Method for Determining Biological Indicator Levels in Tissue") discloses using at least two light emitters to measure a biological parameter. U.S. Pat. No. 11,925,441 (Rantanen et al., Mar. 12, 2024, "Techniques for Determining Blood Pressure Based on Morphological Features of Pulses Preliminary Class") discloses a wearable device with one or more light emitting components, one or more photodetectors, and a controller that couples the light emitting components to the photodetectors.

U.S. patent application 20170311823 (Rausch et al., Nov. 2, 2017, "Optical Trigger for Measurement") discloses detecting and using feature in a photoplethysmogram signal for biometric measurement. U.S. patent application 20240000387 (Realubit et al., Jan. 4, 2024, "Finger Wearable Health Monitoring Device") discloses a finger-worn health monitoring device comprising a circular metal shell. U.S. Pat. No. 10,423,045 (Roberts et al., Sep. 24, 2019, "Electro-Optical Diffractive Waveplate Beam Shaping System") discloses optical beam shaping systems with a diffractive waveplate diffuser. U.S. patent application 20190041265 (Rosen et al., Feb. 7, 2019, "Spatially Variable Filter Systems and Methods") discloses a compact spectrometer system with a spatially variable filter. U.S. patent application 20190231237 (Saddow et al., Aug. 1, 2019, "System and Method for Non-Invasive Blood Glucose Monitoring") and U.S. Pat. No. 11,185,261 (Saddow et al., Nov. 30, 2021, "System and Method for Non-Invasive Blood Glucose Monitoring") disclose a system and method for continuous glucose monitoring (CGM) using a non-invasive sensor composed of a patch antenna operating in the Industrial, Scientific and Medical (ISM) Radio band (5.725 GHz-5.875 GHz).

U.S. patent applications 20220334639 (Sanchez, Oct. 20, 2022, "Projection System for Smart Ring Visual Output") and U.S. patent application 20220383741 (Sanchez, Dec. 1, 2022, "Non-Visual Outputs for a Smart Ring"), and U.S. Pat. No. 11,462,107 (Sanchez, Oct. 4, 2022, "Light Emitting Diodes and Diode Arrays for Smart Ring Visual Output"), disclose a smart ring system for displaying information concerning driving conditions. U.S. Pat. No. 11,479,258 (Sanchez, Oct. 25, 2022, "Smart Ring System for Monitoring UVB Exposure Levels and Using Machine Learning Technique to Predict High Risk Driving Behavior") discloses systems and methods determine a driver's fitness to safely operate a moving vehicle based on UVB exposure. U.S. patent application 20230072436 (Sanchez, Mar. 9, 2023, "Harvesting Energy for a Smart Ring Via Piezoelectric Charging") discloses a smart ring which harvests mechanical energy using piezoelectricity.

U.S. patent applications 20230143293 (Sanchez, May 11, 2023, "Biometric Authentication Using a Smart Ring") and U.S. patent application 20230153416 (Sanchez, May 18, 2023, "Proximity Authentication Using a Smart Ring") discloses systems and methods for performing biometric authentication using a smart ring. U.S. patent application 20230174114 (Sanchez, Jun. 8, 2023, "Smart Ring System for Measuring Stress Levels and Using Machine Learning Techniques to Predict High Risk Driving Behavior") discloses systems and methods determine a driver's fitness to safely operate a moving vehicle based on their stress level. U.S. patent application 20230205170 (Sanchez, Jun. 29, 2023, "Soft Smart Ring and Method of Manufacture") discloses a smart ring with a body made from flexible material, a first part, a second part removably connected to the first part, and at least one pair of break-away portions disposed within the body. U.S. patent application 20230361588 (Sanchez, Nov. 9, 2023, "Smart Ring Power and Charging") discloses a smart ring with a both a removable power source and an internal power source.

U.S. Pat. No. 11,949,673 (Sanchez, Apr. 2, 2024, "Gesture Authentication Using a Smart Ring") discloses systems and methods for multi-factor authentication using a smart ring. U.S. patent application 20170079563 (Seo et al., Mar. 23, 2017, "Method for Sensitively and Selectively Sensing Sugars Using Terahertz Electromagnetic Waves and Device Used Therefor") discloses a method and a device for sensing sugars using terahertz electromagnetic waves. U.S. Pat. No. 11,862,037 (Seymore et al., Jan. 2, 2024, "Methods and Devices for Detection of Eating Behavior") discloses systems, devices, and methods using audio data to detect and correct eating behavior. U.S. patent application 20230190201 (Singleton et al., Jun. 22, 2023, "Techniques for Multiple Wearable Devices") discloses a method of receiving first physiological data from a first wearable device worn at a first position on the user and second physiological data from a second wearable device worn at a second position on the user.

U.S. Pat. No. 11,937,905 (Singleton et al., Mar. 26, 2024, "Techniques for Leveraging Data Collected by Wearable Devices and Additional Devices") discloses a method comprising receiving physiological data from a wearable device and environmental data from an external device. U.S. patent application 20160262673 (Skorich et al., Sep. 15, 2016, "Segmented Sensor") discloses an optical biometric sensor with a planar substrate. U.S. patent application 20180070850 (Stafford et al., Mar. 15, 2018, "Apparatus and Method for Detecting Body Composition and Correlating It With Cognitive Efficiency") discloses a biometric device to measure body hydration and correlate it with cognitive efficiency. U.S. patent application 20130289370 (Sun et al., Oct. 31, 2013, "Method and Device for Detecting a Blood Glucose Level Using an Electromagnetic Wave") discloses a method for detecting a person's blood glucose level using an electromagnetic wave.

U.S. patent application 20240122550 (Syrjala et al., Apr. 18, 2024, "Techniques for Optimal Parameter Tuning for a Wearable Device") discloses comparing measurement quality metrics, respective power consumption metrics, or both, and selecting a measurement profile to be used to acquire additional physiological data. U.S. Pat. No. 11,275,453 (Tham et al., Mar. 15, 2022, "Smart Ring for Manipulating Virtual Objects Displayed By a Wearable Device") discloses systems, devices, media, and methods for using a ring to manipulate a virtual object displayed by smart eyewear. U.S. Pat. No. 11,580,300 (Tham et al., Feb. 14, 2023, "Ring Motion Capture and Message Composition System") discloses systems, devices, media, and methods for composing and sharing a message based on the motion of a ring.

U.S. patent application 20230021838 (Tse et al., Jan. 26, 2023, "Wearable Electronic Device") discloses a wearable electronic device with conductive areas on both inner and outer surfaces. U.S. patent application 20230113714 (Vallius et al., Apr. 13, 2023, "Configurable Photoplethysmogram System"), U.S. Pat. No. 12,074,637 (Vallius et al., Aug. 27, 2024, "Configurable Photoplethysmogram System"), and U.S. patent application 20240364420 (Vallius et al., Oct. 31, 2024, "Configurable Photoplethysmogram System") disclose a wearable electronic device with optical sensors (including transmitter sensors and/or receiver sensors) and protrusions on an inner surface of the wearable electronic device. U.S. patent application 20190167170 (Varsavsky et al., Jun. 6, 2019, "Methods and Systems for Improving the Reliability of Orthogonally Redundant Sensors") discloses using orthogonally redundant sensors to measure glucose level. U.S. Pat. No. 12,076,142 (Venugopal et al., Sep. 3, 2024, "Physiological Monitoring System for Measuring Oxygen Saturation") discloses a wearable device with a housing having a plurality of windows through which light emitters emit light and through which light detectors receive light. U.S. Pat. No. 10,444,834 (Vescovi, Oct. 15, 2019, "Devices, Methods, and User Interfaces for a Wearable Electronic Ring Computing Device") discloses an electronic device with a finger-ring-mounted touchscreen.

U.S. patent application 20190236465 (Vleugels, Aug. 1, 2019, "Activation of Ancillary Sensor Systems Based on Triggers from a Wearable Gesture Sensing Device") discloses an eating monitor with gesture recognition. U.S. patent application 20190333634 (Vleugels et al., Oct. 31, 2019, "Method and Apparatus for Tracking of Food Intake and Other Behaviors and Providing Relevant Feedback"), 20170220772 (Vleugels et al., Aug. 3, 2017, "Method and Apparatus for Tracking of Food Intake and Other Behaviors and Providing Relevant Feedback"), and 20180300458 (Vleugels et al., Oct. 18, 2018, "Method and Apparatus for Tracking of Food Intake and Other Behaviors and Providing Relevant Feedback"), as well as U.S. Pat. No. 10,102,342 (Vleugels et al., Oct. 16, 2018, "Method and Apparatus for Tracking of Food Intake and Other Behaviors and Providing Relevant Feedback") and U.S. Pat. No. 10,373,716 (Vleugels et al., Aug. 6, 2019, "Method and Apparatus for Tracking of Food Intake and Other Behaviors and Providing Relevant Feedback"), disclose a method for detecting, identifying, analyzing, quantifying, tracking, processing and/or influencing food consumption.

U.S. patent application 20200294645 (Vleugels, Sep. 17, 2020, "Gesture-Based Detection of a Physical Behavior Event Based on Gesture Sensor Data and Supplemental Information from at Least One External Source") discloses an automated medication dispensing system which recognizes gestures. U.S. Pat. No. 10,790,054 (Vleugels et al., Sep. 29, 2020, "Method and Apparatus for Tracking of Food Intake and Other Behaviors and Providing Relevant Feedback") discloses a computer-based method of detecting gestures.

U.S. patent applications 20200381101 (Vleugels, Dec. 3, 2020, "Method and Apparatus for Tracking of Food Intake and Other Behaviors and Providing Relevant Feedback") and 20210350920 (Vleugels et al., Nov. 11, 2021, "Method and Apparatus for Tracking of Food Intake and Other Behaviors and Providing Relevant Feedback") disclose methods for detecting, identifying, analyzing, quantifying, tracking, processing and/or influencing the intake of food, eating habits, eating patterns, and/or triggers for food intake events, eating habits, or eating patterns. U.S. patent application 20230297858 (Vleugels et al., Sep. 21, 2023, "Nutritional Content Determination Based on Gesture Detection Data") discloses techniques for nutritional content determination based on gestures.

U.S. patent application 20150220109 (von Badinski et al., Aug. 6, 2015, "Wearable Computing Device") and U.S. Pat. No. 9,582,034 (von Badinski et al., Feb. 28, 2017, "Wearable Computing Device") disclose a finger ring comprising an interior wall, an exterior wall, a flexible circuit board, and a window that facilitates data transmission, battery recharge, and/or status indication. U.S. patent application 20160246326 (von Badinski et al., Aug. 25, 2016, "Wearable Computing Device") discloses a device charger which directs artificial light toward a device. U.S. patent application 20170235332 (von Badinski et al., Aug. 17, 2017, "Wearable Computing Device") discloses a wearable computing device with a photovoltaic element and a base assembly with a concentrated light source directed at the photovoltaic element.

U.S. patent application 20170235933 (von Badinski et al., Aug. 17, 2017, "Wearable Computing Device") and U.S. Pat. No. 10,156,867 (von Badinski et al., Dec. 18, 2018, "Wearable Computing Device") disclose a method for using a finger ring to identify an authorized user by illuminating a portion of the user's skin, imaging the portion, and then generating a capillary map. U.S. Pat. No. 10,139,859 (von Badinski et al., Nov. 27, 2018, "Wearable Computing Device") discloses a wearable ring computing device with a curved battery, a photovoltaic element, and a charging assembly with a concentrated light source. U.S. Pat. No. 10,331,168 (von Badinski et al., Jun. 25, 2019, "Wearable Computing Device") discloses a timepiece computing system which sends command media player instructions to a second computing device.

U.S. patent application 20190204865 (von Badinski et al., Jul. 4, 2019, "Wearable Computing Device") discloses a wearable smart ring with a curved rechargeable battery, an accelerometer, a gyroscope, a heart rate sensor, an internal measurement unit, and an electrocardiogram sensor. U.S. Pat. No. 10,496,131 (von Badinski et al., Dec. 3, 2019, "Wearing Computing Device") discloses a charger for an wearable ring. U.S. patent application 20190384354 (von Badinski et al., Dec. 19, 2019, "Wearable Computing Device") discloses a wearable smart ring which unlocks a person's computing device. U.S. patent application 20200089272 (von Badinski et al., Mar. 19, 2020, "Wearable Computing Device") and U.S. Pat. No. 10,901,460 (von Badinski et al., Jan. 26, 2021, "Wearable Computing Device") disclose a wearable smart ring which identifies an authorized user by scanning the person's blood vessels.

U.S. Pat. No. 10,768,666 (von Badinski et al., Sep. 8, 2020, "Wearable Computing Device") discloses a smart ring which unlocks a client computing device, wherein the ring includes an accelerometer, a gyroscope, and/or other motion sensor. U.S. patent application 20200401183 (von Badinski et al., Dec. 24, 2020, "Wearable Computing Device"), U.S. Pat. No. 11,188,124 (von Badinski et al., Nov. 30, 2021, "Wearable Computing Device"), and U.S. patent application 20220057832 (von Badinski et al., Feb. 24, 2022, "Wearable Computing Device") disclose a smart ring with a curved housing having a U-shape interior, a motion sensor, a memory, a transceiver, a temperature sensor, and a processor. U.S. Pat. No. 10,884,455 (von Badinski et al., Jan. 5, 2021, "Wearable Device and Data Transmission Method") discloses wearable computing device which activates a transceiver based on (EKG) sensor data.

U.S. Pat. No. 11,599,147 (von Badinski et al., Mar. 7, 2023, "Wearable Computing Device") discloses a smart ring with a curved housing having a U-shape interior, a semi-flexible PCB, a motion sensor, a memory, a transceiver, a temperature sensor, and a processor. U.S. patent application 20230213970 (von Badinski et al., Jul. 6, 2023, "Wearable Computing Device") discloses a smart ring with a body having an inner surface and an outer surface, wherein a cavity is formed on the inner surface of the body part and an electronic part is arranged in the cavity. U.S. patent application 20230376071 (von Badinski et al., Nov. 23, 2023, "Wearable Computing Device") discloses a smart ring comprising an external housing component with an outer circumferential surface and an inner circumferential surface, wherein a portion of the inner circumferential surface contacts a person's finger.

U.S. patent applications 20230376072 (von Badinski et al., Nov. 23, 2023, "Wearable Computing Device") and 20230384827 (von Badinski et al., Nov. 30, 2023, "Wearable Computing Device") disclose a smart ring with a curved housing having a U-shape interior, a curved battery, a semi-flexible PCB, a motion sensor, a memory, a transceiver, a temperature sensor, and a processor. U.S. patent application 20230409080 (von Badinski et al., Dec. 21, 2023, "Wearable Computing Device") discloses a smart ring with a curved housing with a substantially transparent portion, a curved battery, a semi-flexible PCB, a motion sensor, a memory, a transceiver, a temperature sensor, and a processor.

U.S. Pat. No. 11,868,178 (von Badinski et al., Jan. 9, 2024, "Wearable Computing Device") discloses a smart ring with a curved housing having a U-shape interior, a battery, a semi-flexible PCB, a motion sensor, a memory, a transceiver, a temperature sensor, and a processor. U.S. Pat. No. 11,868,179 (von Badinski et al., Jan. 9, 2024, "Wearable Computing Device") discloses a smart ring with a curved housing having a U-shape interior, a battery, a semi-flexible PCB, a motion sensor, a memory, a transceiver, a temperature sensor, a processor, an infrared light emitter, and a visible light emitter. U.S. Pat. No. 11,874,701 (von Badinski et al., Jan. 16, 2024, "Wearable Computing Device") discloses a smart ring with a curved housing having a U-shape interior, a battery, a semi-flexible PCB, a motion sensor, a memory, a transceiver, a temperature sensor, and a processor which identifies gestures based on data from the motion sensor.

U.S. Pat. No. 11,874,702 (von Badinski et al., Jan. 16, 2024, "Wearable Computing Device") discloses a smart ring with a curved housing with a substantially transparent portion, a battery, a semi-flexible PCB, a motion sensor, a memory, a transceiver, a temperature sensor, and a processor. U.S. patent application 20240126328 (von Badinski et al., Apr. 18, 2024, "Wearable Computing Device") discloses a smart ring with a curved housing having a U-shape interior, a battery, a semi-flexible PCB, a galvanic sensor, light emitters, light receivers, a memory, a transceiver, a temperature sensor, and a processor. U.S. patent application 20240126329 (von Badinski et al., Apr. 18, 2024, "Wearable Computing Device") discloses a wearable ring device with a ring-shaped housing, a printed circuit board, and a sensor module with infrared light emitters, visible light emitters, and light receivers.

U.S. patent application 20240126330 (von Badinski et al., Apr. 18, 2024, "Wearable Computing Device") discloses a wearable ring device with a ring-shaped housing comprising two metallic materials, a printed circuit board, light emitters, and light receivers. U.S. patent application 20240134417 (von Badinski et al., Apr. 25, 2024, "Wearable Computing Device") discloses a wearable ring device with a ring-shaped housing, a thermoelectric generator, a printed circuit board, light emitters, and light receivers. U.S. patent application 20240143027 (von Badinski et al., May 2, 2024, "Wearable Computing Device") discloses a wearable ring device with a ring-shaped housing with one or more windows, a printed circuit board, light emitters, and light receivers. U.S. patent application 20240143028 (von Badinski et al., May 2, 2024, "Wearable Computing Device") discloses a wearable ring device with a ring-shaped housing, a printed circuit board, and a sensor module that includes red light emitters, infrared light emitters, and light receivers.

U.S. patent application 20240168521 (von Badinski et al., May 23, 2024, "Wearable Computing Device") discloses a wearable ring device with a ring-shaped housing, one or more temperature sensors, a printed circuit board, light emitters, and light receivers. U.S. Pat. No. 12,013,725 (von Badinski et al., Jun. 18, 2024, "Wearable Computing Device") discloses a wearable ring device with a ring-shaped housing, a printed circuit board, a haptic feedback module, red light emitters, infrared light emitters, and light receivers. U.S. patent application 20240201736 (von Badinski et al., Jun. 20, 2024, "Wearable Computing Device") discloses a wearable ring device with a ring-shaped housing, a first conductive contact component, a second conductive contact component, a printed circuit board, light emitters, and light receivers.

U.S. patent application 20170209095 (Wagner et al., Jul. 27, 2017, "Optical Physiological Sensor Modules with Reduced Signal Noise") discloses an optical sensor module with light guides which have outwardly-diverging axial directions. U.S. patent application 20180020979 (Wagner et al., Jan. 25, 2018, "Optical Adapters for Wearable Monitoring Devices") discloses a wearable optical biometric sensor with stabilizing members. U.S. patent application 20180042554 (Wagner et al., Feb. 15, 2018, "Optical Monitoring Apparatus and Methods") discloses a biometric device with a digital camera and a photoplethysmography (PPG) sensor. U.S. patent application 20180078209 (Wagner et al., Mar. 22, 2018, "Stabilized Sensor Modules and Monitoring Devices Incorporating Same") discloses a wearable optical biometric sensor with stabilizing protrusions.

U.S. patent application 20230043018 (Wai et al., Feb. 9, 2023, "Smart Ring for Use with a User Device and Wi-Fi Network") discloses a smart ring with a battery, a memory, processing circuitry, a plurality of sensors, and a plurality of antennas. U.S. patent applications 20180074010 (Wang et al., Mar. 15, 2018, "Application of Electrochemical Impedance Spectroscopy in Sensor Systems, Devices, and Related Methods" and 20180074011 (Wang et al., Mar. 15, 2018, "Application of Electrochemical Impedance Spectroscopy in Sensor Systems, Devices, and Related Methods"), and 20180074012 (Wang et al., Mar. 15, 2018, "Application of Electrochemical Impedance Spectroscopy in Sensor Systems, Devices, and Related Methods") disclose using electrochemical impedance spectroscopy to measure glucose level.

U.S. Pat. No. 10,739,820 (Wang et al., Aug. 11, 2020, "Expandable Ring Device") discloses a ring device including force sensors, ultrasonic sensors, inertial measurement units, optical sensors, touch sensors, and other components. U.S. patent application 20240176425 (Wang et al., May 30, 2024, "Method for Controlling Wearable Device and Wearable Device") discloses detecting an abnormal touch event on a display screen of a wearable device and enabling gesture recognition in response to the abnormal touch event. U.S. patent application 20180123629 (Wetzig, May 3, 2018, "Smart-Ring Methods and Systems") discloses a computerized smart ring which is embedded with electronics, software, sensors wherein the ring can be electronically connected to another computing system.

U.S. patent applications 20170292908 (Wilk et al., Oct. 12, 2017, "Spectrometry System Applications") and 20180143073 (Goldring et al., May 24, 2018, "Spectrometry System Applications") disclose a spectrometer system to determine spectra of an object. U.S. patent application 20170071518 (Xavier Da Silveira et al., Mar. 16, 2017, "Apparatus and Method for Optical Tissue Detection") discloses optical discrimination between body tissue and non-tissue materials. U.S. patent application 20170303788 (Xavier Da Silveira et al., Oct. 26, 2017, "Wearable Device for Tissue Monitoring with Effective Ambient Light Blocking") discloses an optical biometric device with a shield to block ambient light. U.S. patent application 20170319131 (Xavier Da Silveira et al., Nov. 9, 2017, "Method and Device for Hydration Monitoring") discloses using three different wavelengths to measure hydration.

U.S. patent application 20190167201 (Xavier Da Silveira et al., Jun. 6, 2019, "Wearable Athletic Monitoring Using Digital Modulation") discloses a wearable spectroscopic sensor with digital modulation. U.S. patent application 20160338601 (Yang, Nov. 24, 2016, "Optical Fiber Continuous Detecting Blood Sensor and Wearing Apparatus Thereof") discloses using optical fibers and spectroscopic sensors to measure blood pressure. U.S. patent application 20190067257 (Yeon et al., Feb. 28, 2019, "Light-Emitting Diode (LED) Device") discloses a multi-color display includes a plurality of light-emitting cells at least partially defined by a partition layer.

U.S. Pat. No. 11,540,599 (Yokoyama et al., Jan. 3, 2023, "Watch Band with Adjustable Fit") discloses shape-memory tensioning elements which respond to a stimulus in order to adjust the fit of a watch band. U.S. patent application 20240126382 (Yoo, Apr. 18, 2024, "Wearable Device and Method for Controlling Same") discloses a method of controlling a smart ring by sensing contact from a finger on an outer surface electrode on an outer circumference of the ring. U.S. Pat. No. 10,357,165 (Yoon, Jul. 23, 2019, "Method and Apparatus for Acquiring Bioinformation and Apparatus for Testing Bioinformation") discloses a biometric sensor analyzing laser speckle patterns.

SUMMARY OF THE INVENTION

This invention is a biometric wearable device which can be embodied in a smart watch or finger ring with radiowave or microwave energy emitters/transmitters and energy receivers for measuring the level of a biometric parameter such as body oxygenation, hydration, or glucose level. In an example, an energy emitter/transmitter can emit electromagnetic energy which sweeps through a range of frequencies. In an example, an energy emitter/transmitter and an energy receiver can be parallel and/or nested. In an example, energy emitters/transmitters and energy receivers can collectively comprise a two-dimensional array, wherein emitters/transmitters and energy receivers in the array have different locations along circumferential lines of the device and also have different locations along lines which are perpendicular to the circumferential lines. In an example, this device can further comprise a split ring resonator which is located between an energy emitter/transmitter and an energy receiver.

BRIEF INTRODUCTION TO THE FIGURES

FIG. 1 shows a biometric wearable device with at least one radiowave or microwave energy emitter and at least one energy receiver on a housing, wherein the emitters and receivers are parallel to each other and to a circumferential line around the device, and wherein an energy receiver is between energy emitters.

FIG. 2 shows a biometric wearable device with at least one radiowave or microwave energy emitter and at least one energy receiver on a housing, wherein the emitters and receivers are parallel to each other and to a circumferential line around the device, and wherein an energy emitter is between energy receivers.

Figures 15, 16:
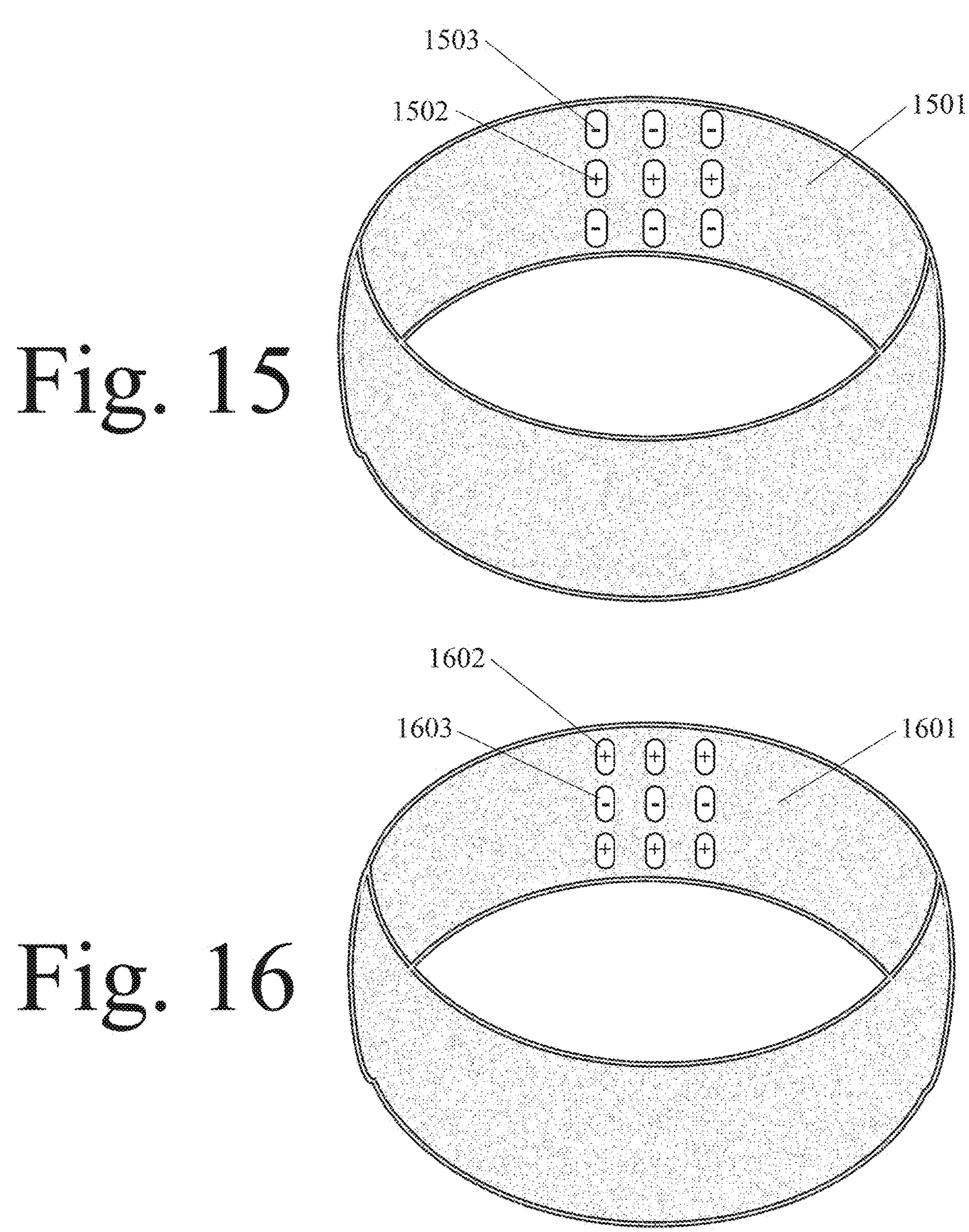

FIG. 15 shows a biometric wearable device (e.g. finger ring) with a two-dimensional array of radiowave or microwave energy emitters and receivers which differ in location along circumferential lines and along lines which are perpendicular to circumferential lines, wherein individual emitters and receivers are perpendicular to circumferential lines, and wherein energy emitters are between energy receivers.

FIG. 16 shows a biometric wearable device (e.g. finger ring) with a two-dimensional array of radiowave or microwave energy emitters and receivers which differ in location along circumferential lines and along lines which are perpendicular to circumferential lines, wherein individual emitters and receivers are perpendicular to circumferential lines, and wherein energy receivers are between energy emitters.

Figures 17, 18:
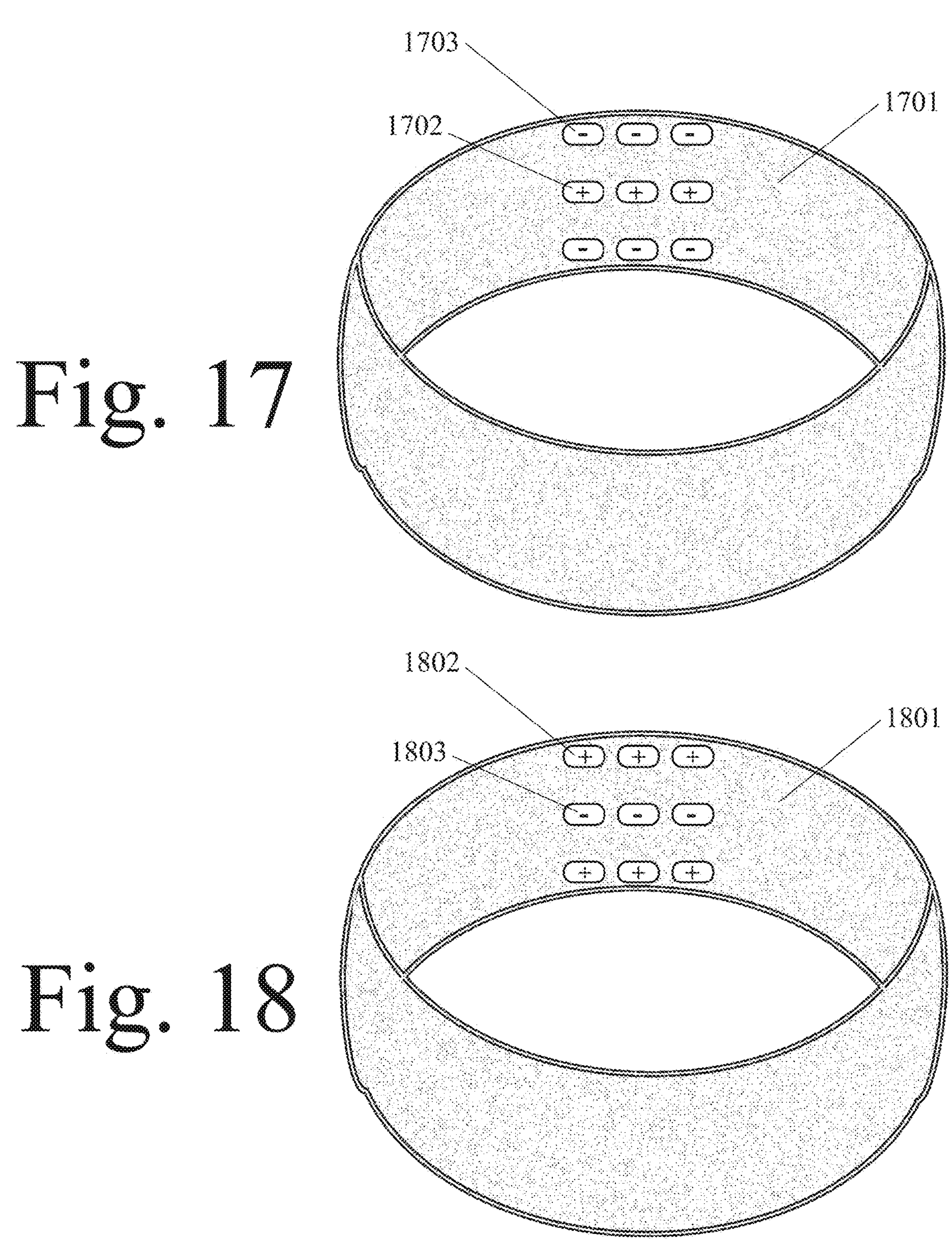

FIG. 17 shows a biometric wearable device (e.g. finger ring) with a two-dimensional array of radiowave or microwave energy emitters and receivers which differ in location along circumferential lines and along lines which are perpendicular to circumferential lines, wherein individual emitters and receivers are parallel to circumferential lines, and wherein energy emitters are between energy receivers.

FIG. 18 shows a biometric wearable device (e.g. finger ring) with a two-dimensional array of radiowave or microwave energy emitters and receivers which differ in location along circumferential lines and along lines which are perpendicular to circumferential lines, wherein individual emitters and receivers are parallel to circumferential lines, and wherein energy receivers are between energy emitters.

Figures 19, 20:
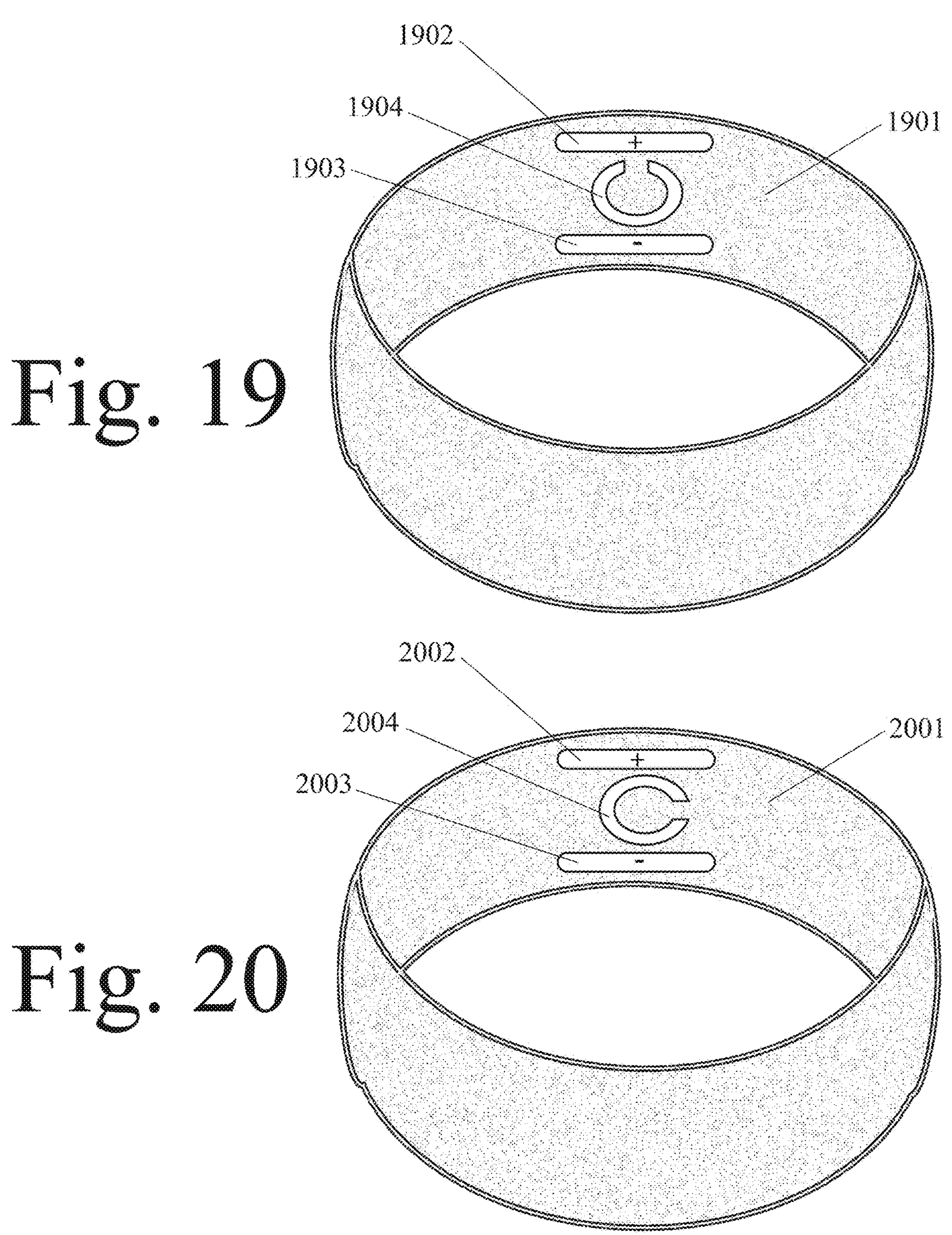

FIG. 19 shows a biometric wearable device with an annular band which holds at least one radiowave or microwave energy emitter, at least one energy receiver, and a split ring resonator between the emitter and the receiver, wherein a gap in the circumference of the resonator is on a radial vector which is perpendicular to the longitudinal axis of the emitter and/or the receiver.

FIG. 20 shows a biometric wearable device with an annular band which holds at least one radiowave or microwave energy emitter, at least one energy receiver, and a split ring resonator between the emitter and the receiver, wherein a gap in the circumference of the resonator is on a radial vector which is parallel to the longitudinal axis of the emitter and/or the receiver.

DETAILED DESCRIPTION OF THE FIGURES

Before discussing the specific embodiments of this invention which are shown in FIGS. 1 through 20, this disclosure provides an introductory section which covers some of the general concepts, components, and methods which comprise this invention. Where relevant, these concepts, components, and methods can be applied as variations to the examples shown in FIGS. 1 through 20 which are discussed afterwards.

In an example, a biometric wearable device can comprise: an arcuate band which is configured to span at least part of the circumference of a body member; a housing which is held on the body member by the arcuate band; an energy emitter on the housing; and an energy receiver on the housing which is configured to receive energy from the energy emitter after that energy has passed through and/or been reflected from the body member.

In an example, a device can be embodied as a smart watch, wrist band, arm band, or finger ring. In an example, the body member can be a wrist, arm, or finger. In an example, data from the energy receiver can be analyzed in order to measure a biometric parameter level selected from the group consisting of: oxygenation level, hydration level, or glucose level. In an example, the energy emitter and/or the energy receiver can comprise an antenna.

In an example, the energy emitter can emit electromagnetic energy with a frequency in the radio wave range. In an example, the energy emitter can emit electromagnetic energy with a frequency in the microwave range. In an example, the energy emitter can emit electromagnetic energy which sweeps through a range of frequencies.

In an example, the energy emitter and the energy receiver can be coplanar. In an example, the energy emitter and the energy receiver can be parallel. In an example, the longitudinal axis of the energy emitter can be parallel to the longitudinal axis of the energy receiver. In an example, the energy emitter and the energy receiver can be nested. In an example, a device can comprise an array, matrix, or series of antennae having different sizes, different shapes, different gaps, and/or different rotations.

In an example, a device can comprise a two-dimensional array of energy emitters and energy receivers which differ in location along a circumference of a device and along axes which are perpendicular to the circumference of a device. In an example, a device can comprise multiple sets of energy emitters and energy receivers which are aligned along a line. In an example, the line can be a circumferential line. In an example, the line can be a proximal-to-distal line. In an example, there can be one energy emitter and multiple energy receivers in a set. In an example, there can be one energy receiver and multiple energy emitters in a set. In an example, a device can further comprise a spit ring resonator between the energy emitter and the energy receiver.

In an example, a biometric wearable device can comprise: an annular band which is configured to span at least part of the circumference of a body member; an energy emitter on the annular band; and an energy receiver on the annular band which is configured to receive energy from the energy emitter after that energy has passed through and/or been reflected from the body member.

In an example, a device can be embodied as a finger ring, wrist band, or arm band. In an example, the body member can be a finger, wrist, or arm. In an example, data from the energy receiver can be analyzed in order to measure a biometric parameter level selected from the group consisting of: oxygenation level, hydration level, or glucose level. In an example, the energy emitter and/or the energy receiver can comprise an antenna.

In an example, the energy emitter can emit electromagnetic energy with a frequency in the radio wave range. In an example, the energy emitter can emit electromagnetic energy with a frequency in the microwave range. In an example, the energy emitter can emit electromagnetic energy which sweeps through a range of frequencies.

In an example, the energy emitter and the energy receiver can be coplanar. In an example, the energy emitter and the energy receiver can be parallel. In an example, the longitudinal axis of the energy emitter can be parallel to the longitudinal axis of the energy receiver. In an example, the energy emitter and the energy receiver can be nested. In an example, a device can comprise an array, matrix, or series of antennae having different sizes, different shapes, different gaps, and/or different rotations.

In an example, a device can comprise a two-dimensional array of energy emitters and energy receivers which differ in location along a circumference of a device and along axes which are perpendicular to the circumference of a device. In an example, a device can comprise multiple sets of energy emitters and energy receivers which are aligned along a line. In an example, the line can be a circumferential line. In an example, the line can be a proximal-to-distal line. In an example, there can be one energy emitter and multiple energy receivers in a set. In an example, there can be one energy receiver and multiple energy emitters in a set. In an example, a device can further comprise a spit ring resonator between the energy emitter and the energy receiver.

In an example, a biometric wearable device can comprise: an energy (e.g. radiowave or microwave) emitter/transmitter; an energy (e.g. radiowave or microwave) receiver; an energy source (e.g. battery), a data processor, and a data transmitter. In an example, a biometric wearable device can be embodied in a finger ring. In an example, a biometric wearable device can be embodied in a smart watch, watch band, wrist band, or other wrist-worn device. In an example, a biometric wearable device can be embodied in an article of clothing.

In an example, a biometric wearable device can comprise: a smart watch or wrist band; an energy (e.g. radiowave or microwave) emitter/transmitter on the smart watch or wrist band; an radiowave or microwave energy (e.g. radiowave or microwave) receiver on the smart watch or wrist band; a power source; a data processor; and a data transmitter. In an example, a body part on which a biometric wearable device is worn can be a person's arm.

In an example, a measured biometric parameter can be blood glucose level. In an example, a measured biometric parameter can be body oxygenation level. In an example, a measured biometric parameter can be oxygen level. In another example, the biometric parameter which is measured by a biometric wearable device can be a person's blood glucose level. In an example, a biometric wearable device can comprise: a first electromagnetic antenna, wherein radiowave or microwave energy is emitted/transmitted from the first antenna; and a second electromagnetic antenna, wherein the radiowave or microwave energy is received by the second antenna.

In another example, a biometric wearable device can have: a first component which is configured to emit radiowave or microwave energy in proximity to body tissue; and a second component which receives this radiowave or microwave energy after it has interacted with the body tissue. In an example, a biometric wearable device can have a radiowave or microwave energy-emitting antenna and a radiowave or microwave energy-receiving antenna. In an example, an energy (e.g. radiowave or microwave) receiver can comprise an antenna. In another embodiment, a biometric wearable device can have two energy (e.g. radiowave or microwave) emitters/transmitters.

In an example, a biometric parameter management system can include: a biometric parameter sensor (e.g. glucose sensor) worn by a person; a wearable pump housing; a pump in the housing; a valve; a substance (e.g. insulin) which affects the biometric parameter level, wherein this substance is pumped into the person's body; a power source (e.g. battery); a data processor; and data transmitter. In another embodiment, a glucose management system can include a biometric wearable device and a wearable insulin pump.

In an example, a closed-loop glucose management system can comprise: a biometric wearable device worn by a person which further comprises an energy (e.g. radiowave or microwave) emitter/transmitter and an energy (e.g. radiowave or microwave) receiver; and a wearable or implanted pump which automatically delivers an insulin into the person's body to maintain glucose levels within a selected range, wherein operation of the pump is based on data collected by the wearable biometric wearable device.

In an example, a biometric wearable device can have a linear energy (e.g. radiowave or microwave) emitter/transmitter which is substantially parallel to the surface of a person's body. In another example, a biometric wearable device can have a planar energy (e.g. radiowave or microwave) emitter/transmitter which is parallel to the surface of a person's body. In an example, a biometric wearable device can have a rectangular radiowave or microwave antenna. In another example, a biometric wearable device can have a circular radiowave or microwave antenna. In an example, a biometric wearable device can have an elliptical radiowave or microwave antenna.

In an example, a longitudinal axis of an energy emitter and/or an individual energy receiver can be parallel to a circumferential line (e.g. a line around a circumference of a device). In another example, a longitudinal axis of an individual energy emitter and/or an individual energy receiver can be perpendicular and/or orthogonal to a circumferential line.

In an example, a biometric wearable device can have a concentric-ring radiowave or microwave antenna. In an example, a biometric wearable device can have an energy (e.g. radiowave or microwave) emitter/transmitter and an energy (e.g. radiowave or microwave) receiver comprising nested and/or concentric rings which form a target or bulls eye configuration. In an example, a biometric wearable device can have a dipole radiowave or microwave antenna. In an example, a biometric wearable device can have a S-shape radiowave or microwave antenna. In another example, first and second biometric wearable devices can be located along the curved surface of a device.

In an example, a biometric wearable device can comprise a spiral-shaped energy (e.g. radiowave or microwave) receiver. In another example, a biometric wearable device can have a flat spiral antenna. In an example, a biometric wearable device can have a spiral energy (e.g. radiowave or microwave) antenna which is substantially parallel to the surface of a person's body. In another embodiment, a biometric wearable device can have an antenna shaped like a circular spiral, oval spiral, square spiral, hexagonal spiral, or octagonal spiral. In an example, a biometric wearable device can include a spiral-shaped energy (e.g. radiowave or microwave) receiver. In another embodiment, a biometric wearable device can include two parallel and/or stacked spiral antennae. In an example, a biometric wearable device can have a tapered antenna which emits radiowave or microwave energy. In another embodiment, a biometric wearable device can have a Y-shaped radiowave or microwave antenna.

In an example, a biometric wearable device can comprise: a first coil which emits/transmits electromagnetic (e.g. radiowave or microwave) energy; and a second coil which receives electromagnetic (e.g. radiowave or microwave) energy. In another example, a biometric wearable device can comprise: a first coil which emits/transmits electromagnetic (e.g. radiowave or microwave) energy; and a second coil which receives electromagnetic (e.g. radiowave or microwave) energy; wherein the first coil and the second coil overlap. In an example, a biometric wearable device can comprise: a first coil which emits/transmits electromagnetic (e.g. radiowave or microwave) energy; and a second coil which receives electromagnetic (e.g. radiowave or microwave) energy; wherein the first coil and the second coil are symmetric (e.g. mirror images) to each other.

In another example, a biometric wearable device can have a hemispherical radiowave or microwave antenna. In an example, a biometric wearable device can have an open-ended coaxial probe. In an example, a biometric wearable device can have a sawtooth shaped radiowave or microwave antenna. In an example, a biometric wearable device can have a spherical radiowave or microwave antenna. In an example, a biometric wearable device can comprise an energy (e.g. radiowave or microwave) emitter/transmitter with a shape selected from the group consisting of: bulls eye pattern, arc of a circle, circle, circular spiral, coaxial probe, comb shape, concentric rings, and conic section.

In an example, a biometric wearable device can comprise an energy (e.g. radiowave or microwave) emitter/transmitter with a shape selected from the group consisting of: S-shape, stacked rings, straight co-linear poles, straight line, target pattern, triangle, T-shape, two complementary sinusoidal shapes, two intertwined spirals, two symmetric spirals, U-shape, Y-shape, and zigzag pattern. In an example, a biometric wearable device can comprise an energy (e.g. radiowave or microwave) receiver with a shape selected from the group consisting of: rectangular spiral, ring, ring between two EM wave (e.g. radiowave or microwave) poles, saddle shape, sawtooth shape, sinusoidal wave, sphere, spit ring, square, square spiral, and square wave.

In an example, a biometric wearable device can comprise one or more radiowave or microwave energy antennae with shapes selected from the group consisting of: convex lens shape, cube shape, cylinder, cylindrical band, dumbbell, ellipse, hemisphere, hexagon, H-shape antenna, microstrip, nested rings, non-equilateral polygon, octagon, Omega-shape, oval, oval spiral, parallel rings, polygon with rounded vertices, polygonal spiral, quadrilateral, rectangle, and rectangular cylinder. In another example, a biometric wearable device can have nested antennae. In an example, an energy (e.g. radiowave or microwave) receiver in a biometric wearable device can have an oval shape.

In another example, a biometric wearable device can have an array, matrix, or series of biometric sensors (e.g. electromagnetic energy emitters and receivers) with a selected progression of different sizes (e.g. smaller to larger), shapes (e.g. less arcuate to more arcuate), gaps (e.g. closer together to farther apart), material compositions, and/or rotations. In an example, a biometric wearable device can have an array, matrix, or series of sets of biometric sensors, wherein each set includes at least one energy (e.g. radiowave or microwave) emitter/transmitter and at least one energy (e.g. radiowave or microwave) receiver, wherein there is a selected progression of different size sets (e.g. smaller to larger), different shape set (e.g. less arcuate to more arcuate), or different distance sets (e.g. closer together to farther apart).

In an example, a biometric wearable device can comprise an array of energy (e.g. radiowave or microwave) emitters/transmitters and energy (e.g. radiowave or microwave) receivers, wherein the distance between energy emitters/transmitters and energy receivers cyclically varies (e.g. alternatingly increasing and decreasing) with distance along an axis of the array. In an example, an energy (e.g. radiowave or microwave) emitter/transmitter can be separated from an energy (e.g. radiowave or microwave) receiver by a selected distance.

In an example, a biometric wearable device can include: a plurality of energy (e.g. radiowave or microwave) emitters/transmitters; and a plurality of energy (e.g. radiowave or microwave) receivers; wherein different emitter-receiver pairs are activated at different times. In an example, a biometric wearable device can include: a plurality of energy (e.g. radiowave or microwave) emitters/transmitters; and a plurality of energy (e.g. radiowave or microwave) receivers; wherein different emitter-receiver pairs are activated at different times to scan the interior of a body part along different scan vectors over time. In an example, a plurality of energy (e.g. radiowave or microwave) emitters/transmitters can emit radiowave or microwave energy at different times. In another example, different antennae or different sections of an antenna can be activated to emit (radiowave or microwave) energy at different times, thereby creating electromagnetic fields of different shapes and sizes.

In another embodiment, a biometric wearable device can comprise: a first electromagnetic antenna, wherein radiowave or microwave energy is emitted/transmitted from the first antenna; and a second electromagnetic antenna, wherein the radiowave or microwave energy is received by the second antenna; wherein the first and second antennae have reversed orientations. In another example, a biometric wearable device can comprise: a first antenna which emits/transmits radiowave or microwave energy; and a second antenna which receives this energy; wherein the first and second antenna are in parallel planes. In an example, a biometric wearable device can have an array of parallel radiowave or microwave antennae. In another embodiment, an array, matrix, or series of biometric wearable sensors can be stacked in parallel to each other. In an example, a biometric wearable device can have a radiowave or microwave antenna comprising parallel rings.

In another embodiment, a biometric wearable device can comprise: an energy (e.g.

radiowave or microwave) emitter/transmitter; and an energy (e.g. radiowave or microwave) receiver; wherein the energy emitter and the energy receiver are colinear. In an example, the longitudinal axis of an energy (e.g. radiowave or microwave) emitter/transmitter and the longitudinal axis of an energy (e.g. radiowave or microwave) receiver can be aligned along a common (virtual) straight line, with a gap or insulator between them. In another example, a biometric wearable device can comprise: an energy (e.g. radiowave or microwave) emitter/transmitter; and an energy (e.g. radiowave or microwave) receiver; wherein the energy emitter and the energy receiver are coplanar. In an example, a biometric wearable device can have an energy (e.g. radiowave or microwave) emitter/transmitter and an energy (e.g. radiowave or microwave) receiver which are both within the same curved planar surface.

In another example, a biometric wearable device can comprise two adjacent radiowave or microwave antennae with interlocking, interdigitating, or intermeshing projections. In an example, a biometric wearable device can comprise: a circular, elliptical, or oval first radiowave or microwave antenna; and a circular, elliptical, or oval second radiowave or microwave antenna; wherein the first antenna and the second antenna are nested. In an example, a biometric wearable device can comprise: an energy (e.g. radiowave or microwave) emitter/transmitter; and an energy (e.g. radiowave or microwave) receiver; wherein the energy emitter and the energy receiver are nested and/or concentric. In an example, a biometric wearable device can comprise: an first radiowave or microwave antenna; and an second radiowave or microwave antenna; wherein the first antenna and the second antenna share a common longitudinal axis.

In an example, a biometric wearable device can comprise: a first energy (e.g. radiowave or microwave) emitter/transmitter with a first polarity vector; a second energy (e.g. radiowave of microwave) emitter/transmitter with a second polarity vector, wherein the second polarity vector is in the opposite direction from the first polarity vector. In an example, a biometric wearable device can comprise: an energy (e.g. radiowave or microwave) emitter/transmitter with a first shape; and an energy (e.g. radiowave or microwave) receiver with a second shape; wherein the second shape is different than the first shape. In an example, a biometric wearable device can comprise: an energy (e.g. radiowave or microwave) emitter/transmitter with a first shape; and an energy (e.g. radiowave or microwave) receiver with a second shape; wherein the first shape is more arcuate and/or rounded than the second shape.

In an example, a biometric wearable device can comprise: first radiowave or microwave antenna with a first shape; and second radiowave or microwave antenna with a second shape; wherein the second shape is more arcuate and/or rounded than the first shape. In an example, a biometric wearable device can comprise: first radiowave or microwave antenna with a first shape; and second radiowave or microwave antenna with a second shape; wherein the first shape is more convoluted and/or undulating than the second shape. In another example, an energy (e.g. radiowave or microwave) emitter/transmitter and energy (e.g. radiowave or microwave) receiver can have interdigitating and/or interlocking shapes.

In an example, a biometric wearable device can comprise: a first electromagnetic antenna, wherein radiowave or microwave energy is emitted/transmitted from the first antenna; and a second electromagnetic antenna, wherein the radiowave or microwave energy is received by the second antenna; wherein the first and second antennae have different sizes. In another example, a biometric wearable device can comprise: an energy (e.g. radiowave or microwave) emitter/transmitter with a first size; and an energy (e.g. radiowave or microwave) receiver with a second size; wherein the second size is greater than the first size.

In an example, a biometric wearable device can comprise: an energy (e.g. radiowave or microwave) emitter/transmitter with a first length; and an energy (e.g. radiowave or microwave) receiver with a second length; wherein the second length is greater than the first length. In another embodiment, a biometric wearable device can comprise: first radiowave or microwave antenna with a first size; and second radiowave or microwave antenna with a second size; wherein the second size is greater than the first size. In an example, a biometric wearable device can comprise: first radiowave or microwave antenna with a first length; and second radiowave or microwave antenna with a second length; wherein the second length is greater than the first length.

In another embodiment, an energy (e.g. radiowave or microwave) emitter/transmitter and an energy (e.g. radiowave or microwave) receiver which comprise a biometric wearable device can be symmetric with respect to a line perpendicular to the shortest-line distance between them. In an example, a biometric wearable device can have a circular or elliptical array, grid, and/or matrix of radiowave or microwave energy transmitters and/or receivers. In another embodiment, a biometric wearable device can have a sunburst and/or radial-spoke array, grid, and/or matrix of radiowave or microwave energy transmitters and/or receivers. In another example, an array of energy (e.g. radiowave or microwave) emitters/transmitters and energy (e.g. radiowave or microwave) receivers can have a circular shape. In an example, an array of energy (e.g. radiowave or microwave) emitters/transmitters and energy (e.g. radiowave or microwave) receivers can have a helical shape. In another example, an array of energy (e.g. radiowave or microwave) emitters/transmitters and energy (e.g. radiowave or microwave) receivers can have a square or rectangular shape.

In an example, a biometric wearable device (e.g. a smart watch) can comprise: a strap or band which spans a portion of the circumference of a person's arm; an enclosure attached to strap or band; and a two-dimensional array of energy emitters and energy receivers on the enclosure. In another example, a biometric wearable device (e.g. for non-invasive glucose monitoring) can comprise a two-dimensional array of energy emitters and energy receivers which is part of a wearable arcuate band or one or more segments (or housings) which are attached to a wearable arcuate band. In an example, a biometric wearable device can comprise a planar array of energy (e.g. radiowave or microwave) emitters/transmitters and energy (e.g. radiowave or microwave) receivers. In an example, a biometric wearable device can comprise a planar matrix or grid of energy (e.g. radiowave or microwave) emitters/transmitters and energy (e.g. radiowave or microwave) receivers.

In an example, a biometric wearable device can comprise a sequence of radiowave or microwave energy sensors, wherein this sequence further comprises an alternating pattern of energy (e.g. radiowave or microwave) emitters/transmitters and energy (e.g. radiowave or microwave) receivers. In an example, a biometric wearable device can comprise a two-dimensional array of energy emitters and energy receivers which is part of a wearable arcuate band or one or more segments (or housings) which are attached to a wearable arcuate band. In an example, a biometric wearable device can comprise an array, matrix, or series of energy (e.g. radiowave or microwave) emitters with a selected progression of different sizes (e.g. smaller to larger), shapes (e.g. less arcuate to more arcuate), gaps (e.g. closer together to farther apart), material compositions, and/or rotations.

In an example, a biometric wearable device can comprise an array, matrix, or series of energy (e.g. radiowave or microwave) emitters and receivers with an alternating sequence of different sizes, different shapes, and/or different rotations/orientations. In an example, a biometric wearable device can have a repeating sequence of energy (e.g. radiowave or microwave) emitters/transmitters and energy (e.g. radiowave or microwave) receivers. In an example, a biometric wearable device can have multiple triads of energy emitters and energy receivers, wherein a triad is aligned along a proximal-to-distal line (e.g. a line which is perpendicular to a circumference of the device). In another example, an array of energy (e.g. radiowave and microwave) emitters/transmitters and energy (e.g. radiowave and microwave) receivers can comprise a plurality of triads of energy emitters and energy receivers, wherein each triad further comprises one energy emitter and two energy receivers.

In an example, an array of energy (e.g. radiowave and microwave) emitters/transmitters and energy (e.g. radiowave and microwave) receivers can comprise a plurality of triads of energy emitters and receivers, wherein each triad further comprises two energy emitters and one energy receiver, and wherein triads are aligned along circumferential lines of the device. In another example, an array of energy (e.g. radiowave and microwave) emitters/transmitters and energy (e.g. radiowave and microwave) receivers can comprise a plurality of sets of energy emitters and energy receivers, wherein each set further comprises one energy emitter and multiple energy receivers. In an example, an array of energy (e.g. radiowave and microwave) emitters/transmitters and energy (e.g. radiowave and microwave) receivers can comprise a plurality of sets of energy emitters and receivers, wherein each set further comprises a central energy receiver surrounded by multiple energy emitters. In an example, there can be multiple triads of energy emitters and energy receivers in a biometric wearable device, wherein a triad is aligned along the same proximal-to-distal line.

In another embodiment, a biometric wearable device can comprise: an energy (e.g. radiowave or microwave) emitter/transmitter at a first location on the circumference of a device worn around a body part (e.g. a finger ring or smart watch); and an energy (e.g. radiowave or microwave) receiver at a second location on the circumference, wherein the first and second locations are separated by 10 to 40 degrees of the circumference. In an example, an array, grid, and/or matrix of (alternating) energy (e.g. radiowave or microwave) emitters/transmitters and receivers can span between 50% and 100% of the circumference of a body part such as a wrist, arm, finger, ankle, or leg. In another embodiment, a plurality of biometric wearable sensors can be stacked in parallel to each other.

In an example, a device (e.g. smart watch) can comprise energy emitters and/or energy receivers on a housing and/or enclosure (e.g. smart watch housing) which is attached to a body part (e.g. wrist) by a band or strap (e.g. watch band or strap). In another example, a device can comprise energy emitters and/or energy receivers on a band or strap (e.g. watch band or strap) which holds a housing and/or enclosure (e.g. smart watch housing) onto a body part (e.g. wrist). In another embodiment, a device (e.g. smart watch) can comprise energy emitters and/or energy receivers on both a housing and/or enclosure (e.g. smart watch housing) and on a band or strap which holds the housing onto a body part (e.g. wrist). In another example, a circumferential array of energy emitters and energy receivers on a smart watch, including those on the watch band as well as those on the watch housing, can collectively span between 60% and 90% of the circumference of the device.

In an example, a biometric wearable device can have one or more actuators which automatically adjust the configuration and/or operation of the device, wherein these actuators are electromagnetic actuators, MEMS actuators, pneumatic actuators, or hydraulic actuators. In another example, a biometric wearable device can include one or more MEMS actuators which change the location, position, and/or orientation of an energy (e.g. radiowave or microwave) emitter/transmitter and/or an energy (e.g. radiowave or microwave) receiver. In an example, a biometric wearable device can include one or more actuators which change the distance between an energy (e.g. radiowave or microwave) emitter/transmitter and an energy (e.g. radiowave or microwave) receiver.

In another example, a biometric wearable device can automatically adjust the angle between an energy (e.g. radiowave or microwave) emitter/transmitter and an energy (e.g. radiowave or microwave) receiver to more accurately measure biometric parameter levels for a specific person or specific type of activity. In an example, a biometric wearable device can comprise: an energy (e.g. radiowave or microwave) emitter/transmitter with a first longitudinal axis; an energy (e.g. radiowave or microwave) receiver with a second longitudinal axis; and an actuator; wherein the actuator selectively and/or cyclically changes the angle between the surface of a person's body and virtual extensions of the first longitudinal axis and/or the second longitudinal axis. In an example, a biometric wearable device can have an actuator which automatically adjusts the angle between two radiowave or microwave antennae.

In an example, a biometric wearable device can further comprise one or more actuators which automatically adjust its internal configuration in response to shifting or rotation of the device on a body part. In an example, a biometric wearable device can automatically adjust the distance (e.g. gap) between an energy (e.g. radiowave or microwave) emitter/transmitter and an energy (e.g. radiowave or microwave) receiver based on changes in their orientation relative to the person's body. In an example, a biometric wearable device can automatically adjust the geometric configuration of an energy (e.g. radiowave or microwave) emitter/transmitter and an energy (e.g. radiowave or microwave) receiver to more accurately measure biometric parameter levels for a specific person or specific type of activity. In an example, a biometric wearable device can have actuators which selectively-adjust and/or cyclically-change the distance between one or more radiowave or microwave antennae and the surface of a body part.

In another example, a biometric wearable device can comprise: an actuator; rotating member (e.g. ring); and one or more energy (e.g. radiowave or microwave) emitters/transmitters and/or receivers which are on the member, wherein the member is rotated by the actuator to identify the optimal location of the emitters/transmitters or receivers from which to measure a biometric parameter. In an example, a biometric wearable device can comprise: an actuator; one or more energy (e.g. radiowave or microwave) emitters/transmitters; and one or more energy (e.g. radiowave or microwave) receivers; wherein the emitters/transmitters and/or the receivers are moved by the actuator to change the distance between the emitters/transmitters and the receivers.

In another example, a biometric wearable device can comprise: an annular housing (e.g. ring or band) which is worn around the circumference of a body part; an energy (e.g. radiowave or microwave) emitter/transmitter; and an actuator (e.g. electromagnetic or MEMS actuator); wherein the actuator changes the radial, clock, and/or compass location of the emitter/transmitter on the circumference of the housing. In an example, a biometric wearable device can comprise: an annular housing (e.g. ring or band) which is worn around the circumference of a body part; a first radiowave or microwave antenna; a second radiowave or microwave antenna; and an actuator (e.g. electromagnetic or MEMS actuator); wherein the actuator changes the radial, clock, and/or compass location of the first radiowave or microwave antenna and/or the second radiowave or microwave antenna on the circumference of the housing.

In an example, a biometric wearable device can further comprise an actuator which automatically adjusts the distance between two radiowave or microwave antennae. In an example, a biometric wearable device can further comprise one or more actuators which automatically adjust its location, orientation, position relative to a body part in response to shifting or rotation of the device on the body part. In another embodiment, a biometric wearable device can further comprise one or more actuators which automatically change the radial (e.g. circumferential, clock hour, and/or compass coordinate) locations of energy (e.g. radiowave or microwave) emitters/transmitters and/or energy (e.g. radiowave or microwave) receivers around the circumference of the device.

In an example, a biometric wearable device can automatically change the size or shape of an energy (e.g. radiowave or microwave) emitter/transmitter based on one or more parameters selected from the group consisting of: changes in the location on a person's body on which they are worn; changes their distance from the surface of the person's body; changes in the pressure and/or force which they apply to the person's body; changes in their angle and/or orientation relative to the person's body; changes in body temperature and/or ambient temperature; changes in body moisture level and/or ambient humidity; and body motion and/or speed.

In another embodiment, a biometric wearable device can comprise: a concave energy (e.g. radiowave or microwave) emitter/transmitter; an energy (e.g. radiowave or microwave) receiver; and an actuator; wherein the actuator automatically changes the concavity of the energy emitter/transmitter. In another example, a biometric wearable device can comprise: an energy (e.g. radiowave or microwave) emitter/transmitter; an energy (e.g. radiowave or microwave) receiver; and an actuator; wherein the actuator automatically increases the size and/or length of the energy receiver. In an example, a biometric wearable device can comprise: an energy (e.g. radiowave or microwave) emitter/transmitter; an energy (e.g. radiowave or microwave) receiver; and an actuator; wherein the actuator selectively and/or cyclically changes the sizes or shapes of the energy emitter/transmitter and/or the energy receiver. In another example, a biometric wearable device can further comprise an actuator which automatically adjusts the size or shape of an EM wave (e.g. radiowave or microwave) antenna.

In another embodiment, a biometric wearable device can have a biometric sensor on a rotating member, wherein rotation of the rotating member moves the biometric sensor in a (circular) sweeping manner. In another example, a biometric wearable device can selectively and/or cyclically vary the power level of energy emitted by one or more energy (e.g. radiowave or microwave) emitters/transmitters. In an example, a biometric wearable device can selectively and/or cyclically change the frequency and/or wavelength of an energy field created by one or more energy (e.g. radiowave or microwave) emitters/transmitters.

In an example, a biometric wearable device can automatically adjust and/or cyclically vary the frequency of energy emitted/transmitted by an energy (e.g. radiowave or microwave) emitter/transmitter. In an example, a biometric wearable device can automatically adjust and/or cyclically vary the wavelength and/or frequency of radiowave or microwave energy emitted from an energy (e.g. radiowave or microwave) emitter/transmitter in order to measure levels of different biometric parameters. In an example, a biometric wearable device can comprise an energy (e.g. radiowave or microwave) emitter/transmitter which emits/transmits energy with sequence of increasing radiowave or microwave frequencies (within a selected frequency range). In an example, a biometric wearable device can comprise: a first radiowave or microwave antenna; and a second radiowave or microwave antenna; wherein a frequency of energy emitted/transmitted by the first antenna is selectively and/or cyclically varied to scan a body part.

In another example, a biometric wearable device can emit radiowave or microwave energy at frequencies which sweep through a selected range. In an example, a biometric wearable device can include an energy (e.g. radiowave or microwave) emitter/transmitter which sweeps through a range of radiowave or microwave frequencies. In another example, multiple resonant frequencies can be identified by transmitting energy over a spectrum (e.g. range) of radiowave or microwave energy frequencies. In an example, the frequency and/or wavelength of radiowave or microwave energy emitted from an energy (e.g. radiowave or microwave) emitter/transmitter can be changed over time to create a chronological sequence of radiowave or microwave energy with different frequencies and/or wavelengths. In another example, a biometric wearable device can be a spectroscopic sensor which measures changes in the spectrum of radiowave or microwave energy caused by interaction with body tissue. In an example, a biometric wearable device can comprise a radiowave or microwave spectroscopic sensor.

In an example, a biometric wearable device array can have at least two sensor triads, wherein each sensor triad includes an energy (e.g. radiowave or microwave) emitter/transmitter, an radiowave or microwave energy resonator, and an radiowave or microwave energy (e.g. radiowave or microwave) receiver. In an example, a biometric wearable device can comprise: an energy (e.g. radiowave or microwave) emitter/transmitter with a first longitudinal axis, an energy (e.g. radiowave or microwave) receiver with a second longitudinal axis, and a split-ring resonator between the emitter/transmitter and the receiver, wherein the mid-point of the split (e.g. gap) in the resonator is along radial vector of the resonator which is parallel to the first longitudinal axis, the second longitudinal axis, or both.

In an example, a biometric wearable device can comprise: an energy (e.g. radiowave or microwave) emitter/transmitter with a first longitudinal axis, an energy (e.g. radiowave or microwave) receiver with a second longitudinal axis, and a split-ring resonator between the emitter/transmitter and the receiver, wherein the split (e.g. gap) in the resonator comprises between 5% and 15% of the circumference of the resonator. In another embodiment, a biometric wearable device can have a cylindrical array, matrix, or series of resonators. In an example, a biometric wearable device can have a non-uniform three-dimensional array, matrix, or series of resonators. In another embodiment, a biometric wearable device can have a plurality of sensor sets, wherein each sensor set further comprises: an energy (e.g. radiowave or microwave) emitter/transmitter, an energy (e.g. radiowave or microwave) receiver, and a split-ring resonator between the energy (e.g. radiowave or microwave) emitter/transmitter and the energy (e.g. radiowave or microwave) receiver.

In an example, a biometric wearable device can have a three-dimensional array, matrix, or series of resonators. In another example, a biometric wearable device can have an array, matrix, or series of co-planar resonators, wherein there is a selected progression in resonator size along an axis of the array, matrix, or series. In another embodiment, a biometric wearable device can have an array, matrix, or series of spit ring resonators with a selected progression of different sizes (e.g. smaller to larger), shapes (e.g. less arcuate to more arcuate), gaps (e.g. closer together to farther apart), material compositions, and/or rotations. In another example, a biometric wearable device can have two or more nested radiowave or microwave energy resonators between an energy (e.g. radiowave or microwave) emitter/transmitter and an radiowave or microwave energy (e.g. radiowave or microwave) receiver.

In an example, a biometric wearable device can have two split ring resonators, wherein a first split ring resonator and a second split ring resonator are nested. In another example, a biometric wearable device can include a circular split-ring resonator. In an example, a biometric wearable device including an electromagnetic resonator comprising two or more stacked rings. In an example, a first resonator and a second resonator can be co-planar. In an example, a resonator can have a gap in its perimeter which produces large capacitance values and lowers the resonant frequency of the resonator. In an example, a resonator which is part of a biometric wearable device can be circular. In an example, a resonator which is part of a biometric wearable device can have a shape which is selected from the group consisting of: cylinder; cylindrical band; ellipse; elliptical ring; and oval.

In an example, an electromagnetic resonator can comprise a spit ring. In an example, an energy conductor between an energy (e.g. radiowave or microwave) emitter/transmitter and an radiowave or microwave energy (e.g. radiowave or microwave) receiver can be a split-ring resonator. In an example, resonators in a three-dimensional array, matrix, or series of resonators can vary in size, shape, resonant frequency, or other features. In another example, the transmission of radiowave or microwave energy from an energy (e.g. radiowave or microwave) emitter/transmitter to an energy (e.g. radiowave or microwave) receiver can be affected by the resonance of a split-ring resonator which, in turn, is affected by the permittivity of nearby body tissue which, in turn, is affected by biometric parameter levels.

In various examples, a resonator can be selected from the group consisting of: annular Bragg resonator, bow tie shape, co-linear elements, comb shape, conic section shape, convex lens shape, C-shape, dumbbell shape, figure eight shape, hemisphere, H-shape, microstrip, Omega-shape, saddle shape, sawtooth shape, semicircle, sinusoidal shape, sphere, square wave shape, S-shape, straight line, T-shape, U-shape, Y-shape, and zigzag shape.

In an example, a biometric wearable device can have a first (split ring) resonator with a first resonant frequency and a second (split ring) resonator with a second resonant frequency. In another example, a biometric wearable device can have a plurality of stacked split ring resonators. In an example, a biometric wearable device can have an energy (e.g. radiowave or microwave) emitter/transmitter and an energy (e.g. radiowave or microwave) receiver, as well as nested split-ring resonators between them. In an example, a resonator can have a number of nested and/or concentric rings, wherein the locations of splits (or gaps) in pairs of adjacent rings (e.g. proximal rings separated by an inter-ring gap) vary from each other by 180-degree rotation.

In another embodiment, a split ring resonator can have a number (X) of perimeter splits of gaps whose radial positions are separated by (360/X) degrees. In an example, the transmission of radiowave or microwave energy from an energy (e.g. radiowave or microwave) emitter/transmitter to an energy (e.g. radiowave or microwave) receiver can be affected by resonances of nested split-ring resonators which, in turn, are affected by the permittivity of nearby body tissue which, in turn, is affected by biometric parameter level. In another embodiment, a biometric wearable device can have a resonator with a shape selected from the group consisting of: circular spiral; oval spiral; square spiral; rectangular spiral; other polygonal spiral; two intertwined spirals; two symmetric spirals; and two stacked spirals.

In an example, a biometric wearable device can collect data which is used to measure biometric parameter levels by creating an electromagnetic field which interacts with body tissue and collecting data concerning this interaction. In another embodiment, a biometric wearable device can measure biometric parameter levels in nearby body fluid and/or tissue by measuring the dielectric constant of that body fluid and/or tissue. In another example, a biometric wearable device can measure the permittivity of body tissue as a function of radiowave or microwave energy at varying frequencies. In an example, the permittivity of body tissue can be different at different radiowave or microwave energy frequencies.

In another example, a biometric wearable device can comprise: an energy (e.g. radiowave or microwave) emitter/transmitter; an energy (e.g. radiowave or microwave) receiver; and an arcuate (e.g. conic-section shaped) electromagnetic energy barrier (e.g. electromagnetic shield) between the energy emitter/transmitter and the energy receiver. In an example, a biometric wearable device can comprise: an energy (e.g. radiowave or microwave) emitter/transmitter; an energy (e.g. radiowave or microwave) receiver; and an electromagnetic energy barrier (e.g. electromagnetic shield) around the energy receiver, wherein the energy emitter/transmitter, the energy receiver, and the electromagnetic energy barrier are coplanar.

In another example, a biometric wearable device can comprise: an energy (e.g. radiowave or microwave) emitter/transmitter; an energy (e.g. radiowave or microwave) receiver; and an electromagnetic energy barrier (e.g. electromagnetic shield) between the energy emitter/transmitter and the energy receiver, wherein the orientation and/or location of the barrier can be automatically adjusted by the device (e.g. by an actuator). In an example, a biometric wearable device can include a circular electromagnetic energy barrier (e.g. electromagnetic shield) can be circular. In an example, a biometric wearable device can include a polygonal (e.g. hexagonal or octagonal) electromagnetic energy barrier (e.g. electromagnetic shield) can be polygonal (e.g. hexagonal or octagonal). In an example, an electromagnetic energy barrier (e.g. electromagnetic shield) can fully encircle an energy (e.g. radiowave or microwave) receiver. In an example, an electromagnetic energy barrier (e.g. electromagnetic shield) can surround an energy (e.g. radiowave or microwave) emitter/transmitter.

In an example, a biometric wearable device can further comprise an arcuate (e.g. circumferential) track, channel, or slot along which an energy (e.g. radiowave or microwave) emitter/transmitter, an energy (e.g. radiowave or microwave) receiver, or both can be moved. In an example, a biometric wearable device can have an arcuate (e.g. circumferential) track, channel, or slot; wherein movement of an energy (e.g. radiowave or microwave) emitter/transmitter, an energy (e.g. radiowave or microwave) receiver, or both along the track, channel, or slot enables customization of the device to the anatomy of a specific person.

In an example, a biometric wearable device can comprise: an energy (e.g. radiowave or microwave) emitter/transmitter; an energy (e.g. radiowave or microwave) receiver; and a fluid-based (e.g. microfluidic) sensor. In an example, a biometric wearable device can include a battery. In an example, a biometric wearable device can transduce, harvest, and/or generate electricity from body motion or kinetic energy. In an example, a biometric wearable device can be integrated into the fabric of an article of clothing such as a shirt, pair of pants or shorts, undershirt, underpants, or sock. In an example, electroconductive threads or yarns in clothing can function as energy (e.g. radiowave or microwave) emitters/transmitters and/or receivers.

In another example, an annular biometric wearable device can comprise multiple moveably-connected (e.g. jointed or hinged) segments (or housings), wherein energy (e.g. radiowave or microwave) emitters/transmitters and energy (e.g. radiowave or microwave) receivers are located on different segments (or housings). In an example, some portions or sections of a biometric wearable device can be relatively flexible and other portions or sections of the device can be rigid, wherein biometric sensors (e.g. electromagnetic energy emitters or receivers) are located on the flexible portions.

In another example, a biometric wearable device can further comprise another sensor selected from the group consisting of: inertial motion unit (e.g. accelerometer and gyroscope), biochemical sensor, camera, capacitive sensor, ECG sensor, EEG sensor, EMG sensor, Hall-effect sensor, infrared sensor, magnetometer, microfluidic sensor, microphone, near-infrared spectroscopic sensor, photoplethysmographic (PPG) sensor, sound sensor, spectrophotometer, and strain gauge. In an example, the operation of a biometric wearable device can be adjusted based on a change in a person's body moisture level and/or environmental moisture level. In another example, the operation of a biometric wearable device can be adjusted based on a change in geographic location (e.g. detected by GPS) and/or proximity to a place that is associated with food consumption. In various examples, a biometric wearable device can continually monitor optical, electromagnetic, temperature, pressure, or motion signals that indicate that the device is properly worn by a person.

In another embodiment, a biometric wearable device can further comprise a human-to-computer communication component (speech recognition, touch screen, keypad or buttons, and/or gesture recognition). In an example, a biometric wearable device can have a data processor which is selected from the group consisting of: central processing unit, computer, microchip, and microprocessor. In another embodiment, a biometric wearable device can provide feedback to the person wearing the device wherein this feedback is selected from the group consisting of: auditory feedback (such as a voice message, alarm, buzzer, ring tone, or song); feedback via computer-generated speech; mild external electric charge or neural stimulation; periodic feedback at a selected time of the day or week; phantom taste or smell; phone call; pre-recorded audio or video message by the person from an earlier time; television-based messages; and tactile, vibratory, or pressure-based feedback.

In an example, data from an energy (e.g. radiowave or microwave) receiver can be analyzed to measure a person's biometric parameter levels. In another embodiment, data from an energy (e.g. radiowave or microwave) receiver can be analyzed using a method selected from the group consisting of: Centroid Analysis, Chi-Squared Analysis, Cluster Analysis, Correlation, Covariance, Data Normalization (DN), Decision Tree Analysis (DTA), Discrete Fourier transform (DFT), and Discriminant Analysis (DA). In an example, data from an energy (e.g. radiowave or microwave) receiver can be analyzed using a method selected from the group consisting of: Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Multi-Band Covariance Analysis, Multi-Channel Covariance Analysis, Multivariate Linear Regression, Multivariate Logit, Multivariate Regression, Naive Bayes Classifier, and Neural Network.

In an example, a biometric wearable device can comprise: an energy (e.g. radiowave or microwave) emitter/transmitter; an energy (e.g. radiowave or microwave) receiver; an energy source (e.g. battery), a data processor, and a data transmitter, wherein data from the energy receiver is analyzed to measure biometric parameter levels. In another example, a biometric wearable device can be embodied in a shirt.

In an example, a biometric wearable device can be embodied in a smart watch, wrist band, wrist phone, wrist watch, fitness watch, or other wrist-worn device; finger ring or artificial finger nail; arm band, arm bracelet, charm bracelet, or smart bracelet; smart necklace, neck chain, neck band, or neck-worn pendant; smart eyewear, smart glasses, electronically-functional eyewear, virtual reality eyewear, or electronically-functional contact lens; cap, hat, visor, helmet, or goggles; smart button, brooch, ornamental pin, clip, smart beads; pin-type, clip-on, or magnetic button; shirt, blouse, jacket, coat, or dress button; head phones, ear phones, hearing aid, ear plug, or ear-worn bluetooth device; dental appliance, dental insert, upper palate attachment or implant; tongue ring, ear ring, or nose ring; electronically-functional skin patch and/or adhesive patch; undergarment with electronic sensors; head band, hair band, or hair clip; ankle strap or bracelet; belt or belt buckle; or key chain or key ring. In another example, a biometric wearable device can be embodied in an article of smart clothing by creating an electromagnetic antenna in fabric used for clothing. In an example, a body part on which a biometric wearable device is worn can be a person's finger. In another example, a body part on which a biometric wearable device is worn can be a person's leg.

In an example, a measured biometric parameter can be body glucose level. In an example, a measured biometric parameter can be heart rate variability. In an example, one of more of the following biometric parameters can also be included in joint statistical analysis: ambient humidity, blood oxygen level, body temperature, cortisol level, external temperature, glucagon level, Hb1Ac level, heart rate, interleukin level, ketone level, lactic acid level, respiration rate, skin moisture level, and skin impedance level. In an example, the biometric parameter which is measured by a biometric wearable device can be a person's body glucose level.

In an example, a biometric wearable device can have a plurality of energy (e.g. radiowave or microwave) emitters/transmitters and/or receivers. In an example, a biometric wearable device can have: an energy (e.g. radiowave or microwave) emitter/transmitter which emits radiowave or microwave energy in proximity to body tissue; and an energy (e.g. radiowave or microwave) receiver which receives this radiowave or microwave energy after it has interacted with the body tissue. In an example, a biometric wearable device can have one or more electromagnetic energy (e.g. radiowave or microwave) antennae. In an example, a biometric wearable device can comprise a radiowave or microwave antenna which is configured to either emit/transmit radiowave or microwave or receive radiowave or microwave energy. In another example, a biometric wearable device can have two energy (e.g. radiowave or microwave) receivers. In an example, a biometric wearable device can be part of a closed-loop system for glycemic control.

In another example, a biometric parameter management system can include a pump which dispenses a parameter-control substances into a person's body when triggered by the results of analysis of data from one or more biometric wearable sensors. In another embodiment, a closed-loop glucose management system can have: a biometric wearable device which automatically collects data which is used to measure a person's glucose levels, wherein this glucose-monitoring biometric wearable device further comprises an energy (e.g. radiowave or microwave) emitter/transmitter, an energy (e.g. radiowave or microwave) receiver, and a resonator between the energy (e.g. radiowave or microwave) emitter/transmitter and the energy (e.g. radiowave or microwave) receiver; and a wearable or implanted pump which automatically delivers a glucose-level-modifying substance into the person's body to maintain glucose levels within a selected range, wherein operation of the pump is based on data collected by the wearable glucose-monitoring biometric wearable device.

In another example, a biometric wearable device can have a linear energy (e.g. radiowave or microwave) antenna which is substantially parallel to the surface of a person's body. In an example, a biometric wearable device can have a planar radiowave or microwave antenna which is substantially parallel to the surface of a person's body. In another embodiment, a biometric wearable device can have a rounded-vertex rectangular radiowave or microwave antenna. In an example, a biometric wearable device can have a conic section shaped radiowave or microwave antenna. In another embodiment, a biometric wearable device can have an H-shaped radiowave or microwave antenna.

In an example, a biometric wearable device can have a nested rings radiowave or microwave antenna. In an example, an energy (e.g. radiowave or microwave) emitter/transmitter can comprise a nested antennae. In an example, a biometric wearable device can have a monopole radiowave or microwave antenna. In another example, a biometric wearable device can have a spit ring radiowave or microwave antenna. In an example, a biometric wearable device can have a coaxial radiowave or microwave antenna.

In another example, a biometric wearable device can comprise: an energy (e.g. radiowave or microwave) emitter/transmitter with a spiral shape; and an energy (e.g. radiowave or microwave) receiver with a spiral shape. In an example, a biometric wearable device can have a polygonal spiral radiowave or microwave antenna. In another example, a biometric wearable device can have a spiral radiowave or microwave antenna. In an example, a biometric wearable device can have one or more radiowave or microwave antennae with spiral-variation shapes selected from the group consisting of: circular spiral; oval spiral; square spiral; rectangular spiral; other polygonal spiral; two intertwined spirals; two symmetric spirals; and two stacked spirals.. In an example, a biometric wearable device can include two adjacent spiral antennae. In an example, a biometric wearable device can include two spiral-shaped antennae, wherein the antennae spiral in opposite clockwise directions.

In an example, a biometric wearable device can have a tapered antenna which receives radiowave or microwave energy. In an example, a biometric wearable device can have a bullseye-shaped radiowave or microwave antenna. In an example, a biometric wearable device can comprise: a first coil which emits/transmits electromagnetic (e.g. radiowave or microwave) energy; and a second coil which receives electromagnetic (e.g. radiowave or microwave) energy; wherein the first coil and the second coil are coplanar. In an example, a biometric wearable device can comprise: a first coil which emits/transmits electromagnetic (e.g. radiowave or microwave) energy; and a second coil which receives electromagnetic (e.g. radiowave or microwave) energy; wherein the first coil and the second coil are nested.

In another embodiment, a biometric wearable device can have a cylindrical radiowave or microwave antenna. In an example, a biometric wearable device can have a hexagonal (mesh) shaped radiowave or microwave antenna. In another example, a biometric wearable device can have a saddle-shaped radiowave or microwave antenna. In another embodiment, a biometric wearable device can have a zigzag pattern radiowave or microwave antenna. In another example, a biometric wearable device can have a radiowave or microwave antenna comprising stacked rings.

In an example, a biometric wearable device can comprise an energy (e.g. radiowave or microwave) emitter/transmitter with a shape selected from the group consisting of: convex lens shape, cube shape, cylinder, cylindrical band, dumbbell, ellipse, hemisphere, hexagon, H-shape antenna, microstrip, nested rings, non-equilateral polygon, octagon, Omega-shape, oval, oval spiral, parallel rings, polygon with rounded vertices, polygonal spiral, quadrilateral, and rectangle. In another embodiment, a biometric wearable device can comprise an energy (e.g. radiowave or microwave) receiver with a shape selected from the group consisting of: bulls eye pattern, arc of a circle, circle, circular spiral, coaxial probe, comb shape, and concentric rings.

In an example, a biometric wearable device can comprise an energy (e.g. radiowave or microwave) receiver with a shape selected from the group consisting of: S-shape, stacked rings, straight co-linear poles, straight line, target pattern, triangle, T-shape, two complementary sinusoidal shapes, two intertwined spirals, two symmetric spirals, U-shape, Y-shape, and zigzag pattern. In an example, a biometric wearable device can comprise one or more radiowave or microwave energy antennae with shapes selected from the group consisting of: rectangular spiral, ring, ring between two EM wave (e.g. radiowave or microwave) poles, saddle shape, sawtooth shape, sinusoidal wave, sphere, spit ring, square, square spiral, and square wave. In an example, a biometric wearable device can have one or more oval-shaped antennae.

In an example, a biometric wearable device can have an array, matrix, or series of defected ground structures with a selected progression of different sizes (e.g. smaller to larger), shapes (e.g. less arcuate to more arcuate), gaps (e.g. closer together to farther apart), material compositions, and/or rotations. In an example, a biometric wearable device can have an array, matrix, or series of energy (e.g. radiowave or microwave) emitters/transmitters with a selected progression of different sizes (e.g. smaller to larger), shapes (e.g. less arcuate to more arcuate), gaps (e.g. closer together to farther apart), material compositions, and/or rotations. In an example, a biometric wearable device can have an array, matrix, or series of energy (e.g. radiowave or microwave) emitters/transmitters and/or receivers of different sizes or configurations.

In an example, a biometric wearable device can have an arcuate energy (e.g. radiowave or microwave) emitter/transmitter and an arcuate energy (e.g. radiowave or microwave) receiver which are configured to be a uniform distance from the curved surface of a person's body. In another example, a biometric wearable device can include an energy (e.g. radiowave or microwave) emitter/transmitter which emits pulses of ultra-wideband radiowave or microwave energy.

In an example, a biometric wearable device can include: a plurality of energy (e.g. radiowave or microwave) emitters/transmitters; and a plurality of energy (e.g. radiowave or microwave) receivers; wherein different emitter-receiver pairs are activated at different times to scan different regions and/or depths of body tissue. In another example, a biometric wearable device can include: a plurality of energy (e.g. radiowave or microwave) emitters/transmitters; and a plurality of energy (e.g. radiowave or microwave) receivers; wherein different emitter-receiver pairs are activated at different times to scan the interior of a body part in a chronological sequence of scan vectors. In an example, a plurality of energy (e.g. radiowave or microwave) emitters/transmitters can emit pulses of radiowave or microwave energy. In an example, different energy (e.g. radiowave or microwave) emitters/transmitters can emit radiowave or microwave energy at different times and/or in a chronological sequence.

In an example, a biometric wearable device can comprise: a first electromagnetic antenna, wherein radiowave or microwave energy is emitted/transmitted from the first antenna; and a second electromagnetic antenna, wherein the radiowave or microwave energy is received by the second antenna; wherein the first and second antennae are parallel to each other. In an example, a biometric wearable device can comprise: a first antenna with a first longitudinal axis, wherein the first antenna emits/transmits radiowave or microwave energy; and a second antenna with a second longitudinal axis, wherein the second antenna receives this energy; wherein the first and second longitudinal axes are parallel to each other. In another embodiment, a biometric wearable device can have an energy (e.g. radiowave or microwave) emitter/transmitter and an energy (e.g. radiowave or microwave) receiver which are parallel. In an example, the ends of an energy (e.g. radiowave or microwave) emitter/transmitter and an energy (e.g. radiowave or microwave) receiver which are closest to each other can be parallel.

In another embodiment, a biometric wearable device can comprise: a first electromagnetic antenna, wherein radiowave or microwave energy is emitted/transmitted from the first antenna; and a second electromagnetic antenna, wherein the radiowave or microwave energy is received by the second antenna; wherein the first and second antennae are colinear. In another embodiment, a biometric wearable device can comprise: an energy (e.g. radiowave or microwave) emitter/transmitter; and an energy (e.g. radiowave or microwave) receiver; wherein longitudinal axes of the energy emitter and the energy receiver are colinear.

In another example, a biometric wearable device can comprise: a first electromagnetic antenna, wherein radiowave or microwave energy is emitted/transmitted from the first antenna; and a second electromagnetic antenna, wherein the radiowave or microwave energy is received by the second antenna; wherein the first and second antennae are coplanar. In an example, a biometric wearable device can comprise: an energy (e.g. radiowave or microwave) emitter/transmitter; and an energy (e.g. radiowave or microwave) receiver; wherein the energy emitter and the energy receiver are in different planes. In another example, an energy (e.g. radiowave or microwave) emitter/transmitter and an energy (e.g. radiowave or microwave) receiver can both be within a common flat plane.

In an example, a biometric wearable device can comprise: a first electromagnetic antenna, wherein radiowave or microwave energy is emitted/transmitted from the first antenna; and a second electromagnetic antenna, wherein the radiowave or microwave energy is received by the second antenna; wherein the first and second antennae are interdigitated. In another example, a biometric wearable device can comprise: a convex energy (e.g. radiowave or microwave) emitter/transmitter; and a convex energy (e.g. radiowave or microwave) receiver; wherein the energy emitter and the energy receiver are nested. In an example, a biometric wearable device can comprise: an energy (e.g. radiowave or microwave) emitter/transmitter; and an energy (e.g. radiowave or microwave) receiver; wherein the energy emitter and the energy receiver share a common longitudinal axis. In an example, a biometric wearable device can comprise: an first radiowave or microwave antenna with a first longitudinal axis; and an second radiowave or microwave antenna with a second longitudinal axis; wherein the first longitudinal axis and the second longitudinal axis are colinear. In an example, a biometric wearable device can comprise: an energy (e.g. radiowave or microwave) emitter/transmitter with a first polarity vector; an energy (e.g. radiowave of microwave) receiver with a second polarity vector, wherein the second polarity vector is different than the first polarity vector.

In an example, a biometric wearable device can comprise: an energy (e.g. radiowave or microwave) emitter/transmitter with a first shape; and an energy (e.g. radiowave or microwave) receiver with a second shape; wherein the second shape is more arcuate and/or rounded than the first shape. In an example, a biometric wearable device can comprise: an energy (e.g. radiowave or microwave) emitter/transmitter with a first shape; and an energy (e.g. radiowave or microwave) receiver with a second shape; wherein the first shape is more convoluted and/or undulating than the second shape. In an example, a biometric wearable device can comprise: first radiowave or microwave antenna with a first shape; and second radiowave or microwave antenna with a second shape; wherein the second shape is more convoluted and/or undulating than the first shape. In an example, an energy (e.g. radiowave or microwave) emitter/transmitter and energy (e.g. radiowave or microwave) receiver can have geometrically-complementary shapes. In an example, the ends of an energy (e.g. radiowave or microwave) emitter/transmitter and an energy (e.g. radiowave or microwave) receiver which face each other can have complementary or interlocking shapes.

In an example, a biometric wearable device can comprise: an energy (e.g. radiowave or microwave) emitter/transmitter with a first size; and an energy (e.g. radiowave or microwave) receiver with a second size; wherein the first size is greater than the second size. In an example, a biometric wearable device can comprise: an energy (e.g. radiowave or microwave) emitter/transmitter with a first size; and an energy (e.g. radiowave or microwave) receiver with a second size; wherein the second size is at least 20% greater than the first size. In another example, a biometric wearable device can comprise: first radiowave or microwave antenna with a first size; and second radiowave or microwave antenna with a second size; wherein the first size is greater than the second size. In an example, a biometric wearable device can comprise: first radiowave or microwave antenna with a first size; and second radiowave or microwave antenna with a second size; wherein the second size is at least 20% greater than the first size.

In another example, a biometric wearable device can comprise: a first antenna which emits/transmits radiowave or microwave energy; and a second antenna which receives this energy; wherein the first and second antenna are symmetric to each other. In an example, a biometric wearable device can comprise a planar array of electromagnetic sensors, wherein this array further comprises one or more energy (e.g. radiowave or microwave) emitters/transmitters and one or more energy (e.g. radiowave or microwave) receivers. In another example, a biometric wearable device can have a linear sequence of energy (e.g. radiowave or microwave) emitters/transmitters and energy (e.g. radiowave or microwave) receivers.

In an example, a biometric wearable device can have an arcuate array, matrix, or series of energy (e.g. radiowave or microwave) emitters/transmitters. In an example, an array of energy (e.g. radiowave or microwave) emitters/transmitters and energy (e.g. radiowave or microwave) receivers can have a conic section shape. In an example, an array of energy (e.g. radiowave or microwave) emitters/transmitters and energy (e.g. radiowave or microwave) receivers can have a hexagonal shape. In an example, an array of energy (e.g. radiowave or microwave) emitters/transmitters and energy (e.g. radiowave or microwave) receivers can have a sunburst (e.g. radial spoke) shape.

In another embodiment, a biometric wearable device (e.g. a smart watch) can comprise: a strap or band which spans a portion of the circumference of a person's arm; an enclosure attached to strap or band; and a two-dimensional sensor array on the enclosure, wherein sensors in the two-dimensional array differ in location along a device circumference and differ in location along axes which are perpendicular to the circumference, and wherein sensors in the two-dimensional sensor array are electromagnetic energy sensors which measure parameters and/or patterns of electromagnetic energy passing through tissue of a person's arm.

In an example, a biometric wearable device (e.g. for the arm) with a plurality of close-fitting biometric sensors can comprise: an attachment member, such as a strap or band, which is configured to span at least a portion of the circumference of a person's arm; an enclosure which is part of (or attached to) the attachment member; and a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device. In an example, a biometric wearable device can comprise a planar array of multiple energy (e.g. radiowave or microwave) emitters/transmitters and multiple energy (e.g. radiowave or microwave) receivers.

In an example, a biometric wearable device can comprise a planar matrix or grid of alternating energy (e.g. radiowave or microwave) emitters/transmitters and energy (e.g. radiowave or microwave) receivers. In an example, a biometric wearable device can comprise a two-dimensional array of energy emitters and energy receivers which is part of a wearable arcuate band or one or more segments (or housings) which are attached to a wearable arcuate band. In an example, a biometric wearable device can comprise an array of energy (e.g. radiowave or microwave) emitters and receivers with different sizes, different shapes, and/or different rotations/orientations. In another example, a biometric wearable device can comprise an array, matrix, or series of energy (e.g. radiowave or microwave) receivers with a selected progression of different sizes (e.g. smaller to larger), shapes (e.g. less arcuate to more arcuate), gaps (e.g. closer together to farther apart), material compositions, and/or rotations.

In an example, a biometric wearable device can have a central energy (e.g. radiowave or microwave) emitter/transmitter and a plurality of energy (e.g. radiowave or microwave) receivers around the central energy (e.g. radiowave or microwave) emitter/transmitter. In another example, a biometric wearable device can have an alternating sequence of energy (e.g. radiowave or microwave) emitters/transmitters and energy (e.g. radiowave or microwave) receivers. In another embodiment, an annular biometric wearable device can have a circumferential array of alternating energy (e.g. radiowave or microwave) emitters/transmitters and energy (e.g. radiowave or microwave) receivers. In another example, an array of energy (e.g. radiowave and microwave) emitters/transmitters and energy (e.g. radiowave and microwave) receivers can comprise a plurality of triads of energy emitters and receivers, wherein each triad further comprises two energy emitters and one energy receiver.

In an example, an array of energy (e.g. radiowave and microwave) emitters/transmitters and energy (e.g. radiowave and microwave) receivers can comprise a plurality of triads of energy emitters and energy receivers, wherein each triad further comprises one energy emitter and two energy receivers, and wherein triads are aligned along proximal-to-distal (e.g. perpendicular to circumferential) lines of the device. In an example, an array of energy (e.g. radiowave and microwave) emitters/transmitters and energy (e.g. radiowave and microwave) receivers can comprise a plurality of sets of energy emitters and receivers, wherein each set further comprises multiple energy emitters and one energy receiver. In an example, energy (e.g. radiowave or microwave) emitters/transmitters and energy (e.g. radiowave or microwave) receivers can alternate around a device circumference.

In an example, a biometric wearable device array can comprise an alternating sequence of energy (e.g. radiowave or microwave) emitters/transmitters and energy (e.g. radiowave or microwave) receivers around (a portion of) a circumference of the device. In an example, a biometric wearable device can comprise: an energy (e.g. radiowave or microwave) emitter/transmitter at a first location on the circumference of a device worn around a body part (e.g. a finger ring or smart watch); and an energy (e.g. radiowave or microwave) receiver at a second location on the circumference, wherein the first and second locations are separated by 40 to 65 degrees of the circumference. In an example, a biometric wearable device can have a three-dimensionally stacked array of energy (e.g. radiowave or microwave) emitters/transmitters and/or energy (e.g. radiowave or microwave) receivers. In an example, a plurality of biometric wearable sensors can be three-dimensionally stacked.

In another embodiment, a biometric wearable device can include one or more actuators which change the location, position, and/or orientation of an energy (e.g. radiowave or microwave) emitter/transmitter and/or an energy (e.g. radiowave or microwave) receiver. In an example, a biometric wearable device can include one or more pneumatic or hydraulic actuators which change the location, position, and/or orientation of an energy (e.g. radiowave or microwave) emitter/transmitter and/or an energy (e.g. radiowave or microwave) receiver. In an example, a biometric wearable device can include one or more actuators which change the distance between a surface of a person's body and an energy (e.g. radiowave or microwave) emitter/transmitter and/or an energy (e.g. radiowave or microwave) receiver.

In an example, a biometric wearable device can comprise: an energy (e.g. radiowave or microwave) emitter/transmitter; an energy (e.g. radiowave or microwave) receiver; and an actuator; wherein the actuator selectively and/or cyclically changes the angle between the energy emitter/transmitter and the energy receiver. In an example, a biometric wearable device can have (electromagnetic) actuators which selectively-adjust and/or cyclically-change the angles between one or more radiowave or microwave antennae and the surface of a body part. In another example, a biometric wearable device can include an actuator which automatically adjusts the orientation and/or angle of a biometric sensor relative to the surface of a person's body in order to maintain consistent measurement of biometric parameter levels.

In an example, a biometric wearable device can automatically adjust the distance (e.g. gap) between an energy (e.g. radiowave or microwave) emitter/transmitter and an energy (e.g. radiowave or microwave) receiver based on changes in the location on a person's body on which the device is worn. In another example, a biometric wearable device can automatically adjust the distance (e.g. gap) between an energy (e.g. radiowave or microwave) emitter/transmitter and an energy (e.g. radiowave or microwave) receiver in order to scan different tissue depths or regions. In an example, a biometric wearable device can automatically adjust the distance between an energy (e.g. radiowave or microwave) emitter/transmitter and an energy (e.g. radiowave or microwave) receiver to more accurately measure biometric parameter levels for a specific person or specific type of activity. In another example, a biometric wearable device can have actuators which selectively-adjust and/or cyclically-change the distance between one or more energy (e.g. radiowave or microwave) emitters/transmitters and the surface of a body part.

In another embodiment, a biometric wearable device can comprise: an actuator; rotating member (e.g. ring); and one or more energy (e.g. radiowave or microwave) emitters/transmitters and/or receivers which are on the member, wherein the member is rotated by the actuator to scan different tissue regions and/or depths. In an example, a biometric wearable device can comprise: an actuator; one or more energy (e.g. radiowave or microwave) emitters/transmitters; and one or more energy (e.g. radiowave or microwave) receivers; wherein the emitters/transmitters and/or the receivers are moved by the actuator to change the distance between the emitters/transmitters and/or the receivers and the surface of a person's body.

In an example, a biometric wearable device can comprise: an annular housing (e.g. ring or band) which is worn around the circumference of a body part; an energy (e.g. radiowave or microwave) emitter/transmitter; an energy (e.g. radiowave or microwave) receiver; and an actuator (e.g. electromagnetic or MEMS actuator); wherein the actuator changes the radial, clock, and/or compass location of the energy emitter/transmitter and/or energy receiver on the circumference of the housing. In an example, a biometric wearable device can further comprise an actuator which automatically adjusts the location, orientation, position, and/or configuration of an energy receiving antenna in order to more accurately and consistently measure a biometric parameter level. In an example, a biometric wearable device can further comprise a rotating member (e.g. rotating ring or ball) which holds an energy (e.g. radiowave or microwave) emitter/transmitter and/or an energy (e.g. radiowave or microwave) receiver, wherein rotation of the member changes the angle between the surface of a body part and the energy emitter/transmitter and/or energy receiver.

In an example, a biometric wearable device can further comprise one or more actuators which automatically change the location, orientation, position, and/or configuration of energy (e.g. radiowave or microwave) emitters/transmitters and/or energy (e.g. radiowave or microwave) receivers in order to more accurately and consistently measure a biometric parameter level. In an example, a biometric wearable device can have a rotating member (e.g. ring) with one or more energy (e.g. radiowave or microwave) emitters/transmitters or receivers on the member, wherein this member is rotated by a person wearing the device in order to identify the optimal location of the emitters/transmitters or receivers from which to measure a biometric parameter.

In an example, a biometric wearable device can automatically change the size or shape of an energy (e.g. radiowave or microwave) emitter/transmitter. In another embodiment, a biometric wearable device can comprise: a housing which is worn on a body part; a first radiowave or microwave antenna; a second radiowave or microwave antenna; and an actuator (e.g. electromagnetic or MEMS actuator); wherein the actuator changes the size or shape of the first radiowave or microwave antenna and/or the second radiowave or microwave antenna. In an example, a biometric wearable device can comprise: an energy (e.g. radiowave or microwave) emitter/transmitter; an energy (e.g. radiowave or microwave) receiver; and an actuator; wherein the actuator automatically varies the size and/or length of the energy emitter/transmitter in a cyclical manner. In another example, a biometric wearable device can further an actuator which automatically adjusts the size or shape of an radiowave or microwave energy sensor. In an example, the depth, breadth, location, and/or type of body tissue or fluid through which radiowave or microwave energy passes can be changed by adjusting the location or shape of an energy (e.g. radiowave or microwave) emitter/transmitter.

In another example, a biometric wearable device can have a rotating sensor. In an example, a biometric wearable device can selectively and/or cyclically change the direction, orientation, and/or polarity of an energy field created by one or more energy (e.g. radiowave or microwave) emitters/transmitters. In another example, a biometric wearable device can selectively and/or cyclically change the pulsation of an energy field created by one or more energy (e.g. radiowave or microwave) emitters/transmitters.

In an example, a biometric wearable device can automatically adjust and/or cyclically vary the frequency of energy emitted/transmitted by an energy (e.g. radiowave or microwave) emitter/transmitter based on changes in the location on a person's body on which the device is worn, changes their distance from the surface of the person's body, changes in their angle and/or orientation relative to the person's body, changes in body temperature and/or ambient temperature, changes in body moisture level and/or ambient humidity, or body motion. In an example, a biometric wearable device can automatically adjust and/or cyclically vary the wavelength and/or frequency of radiowave or microwave energy emitted from an energy (e.g. radiowave or microwave) emitter/transmitter in order to identify the optical frequency (or frequency range) for measuring the level of a selected biometric parameters.

In an example, a biometric wearable device can comprise an energy (e.g. radiowave or microwave) emitter/transmitter which emits/transmits energy with sequence of increasing radiowave or microwave frequencies (within a selected frequency range) in order to scan different tissue regions or depths. In an example, a biometric wearable device can comprise: an energy (e.g. radiowave or microwave) emitter/transmitter; and an energy (e.g. radiowave or microwave) receiver; wherein a frequency of energy emitted/transmitted by the emitter/transmitter is selectively and/or cyclically varied in order to scan a body part.

In an example, a biometric wearable device can emit radiowave or microwave energy at varying frequencies within a selected range in order to collect information about the interaction between that energy and body tissue across a spectrum of frequencies. In another embodiment, a biometric wearable device can selectively and/or cyclically vary the frequency and/or wavelength of energy emitted by one or more energy (e.g. radiowave or microwave) emitters/transmitters. In an example, the depth, breadth, location, and/or type of body tissue or fluid through which radiowave or microwave energy passes can be changed by adjusting the power, wavelength, and/or frequency of radiowave or microwave energy emitted from an energy (e.g. radiowave or microwave) emitter/transmitter.

In another embodiment, a first energy (e.g. radiowave or microwave) emitter/transmitter can emit radiowave or microwave energy with a first frequency and the second energy (e.g. radiowave or microwave) emitter/transmitter can emit radiowave or microwave energy with a second frequency. In another embodiment, a biometric wearable device can be a spectroscopy sensor which collects information about interaction between radiowave or microwave energy and body tissue at multiple frequencies. In another example, an energy (e.g. radiowave or microwave) emitter/transmitter on a biometric wearable device can sweep through a range of energy frequencies.

In an example, a biometric wearable device can comprise: an energy (e.g. radiowave or microwave) emitter/transmitter, an energy (e.g. radiowave or microwave) receiver, and a split-ring resonator. In another example, a biometric wearable device can comprise: an energy (e.g. radiowave or microwave) emitter/transmitter with a first longitudinal axis, an energy (e.g. radiowave or microwave) receiver with a second longitudinal axis, and a split-ring resonator between the emitter/transmitter and the receiver, wherein the midpoint of the split (e.g. gap) in the resonator is along radial vector of the resonator which is perpendicular to the first longitudinal axis, the second longitudinal axis, or both. In another example, a biometric wearable device can further comprise an electromagnetic resonator between an energy (e.g. radiowave or microwave) emitter/transmitter and an radiowave or microwave energy (e.g. radiowave or microwave) receiver.

In an example, a biometric wearable device can have a defected ground structure. In an example, a biometric wearable device can have a plurality of stacked resonators. In an example, a biometric wearable device can have a radiowave or microwave spectroscopy sensor which measures multiple resonant frequencies of one or more resonators by sweeping through a range of radiowave or microwave frequencies. In an example, a biometric wearable device can have an array, matrix, or series of co-planar resonators, wherein there is a selected progression in resonator frequency along an axis of the array, matrix, or series. In an example, a biometric wearable device can have an array, matrix, or series of co-planar resonators, wherein there is a selected progression in resonator size from a smaller to larger along an axis of the array, matrix, or series.

In an example, a biometric wearable device can have an electromagnetic resonator. In an example, a biometric wearable device can have two or more stacked radiowave or microwave energy resonators between an energy (e.g. radiowave or microwave) emitter/transmitter and an radiowave or microwave energy (e.g. radiowave or microwave) receiver. In an example, a biometric wearable device can have two split ring resonators, wherein a first split ring resonator and a second split ring resonator are symmetric and/or reflected relative to each other. In an example, a biometric wearable device can include a quadrilateral split-ring resonator. In another example, a biometric wearable device including an electromagnetic resonator comprising two or more nested rings.

In an example, a resonator can be a ring with one or more spits or gaps in its circumference. In another example, a resonator which is part of a biometric wearable device can be a ring. In an example, a resonator which is part of a biometric wearable device can be polygonal. In another example, a resonator which is part of a biometric wearable device can have a shape which is selected from the group consisting of: polygon with rounded vertices; square, rectangle, or other quadrilateral; square or rectangular cylinder; triangle; hexagon or octagon; non-equilateral polygon; other polygon or polygon with rounded vertexes; cube; and stacked or parallel squares. In an example, an electromagnetic resonator can comprise two or more stacked rings.

In another example, resonators in a three-dimensional array, matrix, or series which are closer to the surface of a person's body can have a lower resonant frequency and resonators which are farther from the surface of the person's body can have a higher resonant frequency. In an example, resonators which are closer to the surface of a person's body can be smaller and resonators which are farther from the surface of the person's body can be larger. In an example, the transmission of radiowave or microwave energy from the energy (e.g. radiowave or microwave) emitter/transmitter to the energy (e.g. radiowave or microwave) receiver can be affected by the resonance of the split-ring resonator between them which, in turn, is affected by the permittivity of nearby body tissue which, in turn, is affected by biometric parameter levels.

In an example, a biometric wearable device can have a (split ring) resonator which is substantially parallel to the surface of a person's body. In an example, a biometric wearable device can have a first (split ring) resonator with a first orientation and a second (split ring) resonator with a second orientation, wherein the second orientation is different than the first orientation. In an example, a biometric wearable device can have a plurality of split-ring resonators with a combined configuration selected from the group consisting of: nested or concentric; arrayed in series; arrayed in parallel; stacked three-dimensionally; symmetric; asymmetric; spiral and/or helical; and interdigitated or interlocking.

In an example, a first resonator can differ from a second resonator in one or more aspects selected from the group consisting of: resonator shape; resonator size; resonator orientation with respect to the connector line; resonator material; resonator distance from the surface of a person's body; resonator symmetry; number of splits (or gaps); size of splits (or gaps); location and/or orientation of splits (or gaps); nested configuration; and stacked configuration. In an example, a resonator which is part of a biometric wearable device can have one or more splits (or gaps). In another embodiment, changes in the biometric parameter levels of nearby body tissue change the permittivity of that body tissue, which changes the resonant frequency of the split Ring Resonator (SRR), which enables measurement of biometric parameter levels. In an example, there can be two splits (or gaps) in a resonator, one centered at the 360-degree (12 o'clock) location and one at the 180-degree (6 o'clock) location.

In another example, a biometric wearable device can have a spiral-shaped electromagnetic resonator. In another embodiment, a biometric wearable device can include a dielectric constant sensor. In another example, a biometric wearable device can measure biometric parameter levels in nearby body fluid and/or tissue by measuring the permittivity of that body fluid and/or tissue. In an example, a biometric wearable device can monitor a person's biometric parameter levels by measuring changes in the electromagnetic impedance, resistance, conductivity, or permittivity of finger tissue. In another example, there can be an inverse relationship between a biometric parameter level in body tissue and the dielectric constant of that body tissue.

In another embodiment, a biometric wearable device can comprise: an energy (e.g. radiowave or microwave) emitter/transmitter; an energy (e.g. radiowave or microwave) receiver; and an electromagnetic energy barrier (e.g. electromagnetic shield) between the energy emitter/transmitter and the energy receiver. In an example, a biometric wearable device can comprise: an energy (e.g. radiowave or microwave) emitter/transmitter; an energy (e.g. radiowave or microwave) receiver; and an electromagnetic energy barrier (e.g. electromagnetic shield) around the energy receiver. In an example, a biometric wearable device can further comprise an electromagnetic energy barrier (e.g. electromagnetic shield) between an energy (e.g. radiowave or microwave) emitter/transmitter and an energy (e.g. radiowave or microwave) receiver which reduces the transmission of energy directly from the emitter/transmitter to the receiver.

In an example, a biometric wearable device can include a hemispherical electromagnetic energy barrier (e.g. electromagnetic shield). In an example, a biometric wearable device can include an arcuate electromagnetic energy barrier (e.g. electromagnetic shield). In an example, an electromagnetic energy barrier (e.g. electromagnetic shield) can have a circular, elliptical, sinusoidal, or other arcuate shape. In an example, an electromagnetic energy barrier (e.g. electromagnetic shield) can surround an energy (e.g. radiowave or microwave) receiver.

In an example, a biometric wearable device can have an arcuate (e.g. circumferential) track, channel, or slot; wherein the location of an energy (e.g. radiowave or microwave) emitter/transmitter and/or an energy (e.g. radiowave or microwave) receiver relative to the surface of a body part is changed by moving the energy (e.g. radiowave or microwave) emitter/transmitter, the energy (e.g. radiowave or microwave) receiver, or both along the track, channel, or slot.

In an example, a biometric wearable device can be a microfluidic device which comprises: a housing which is worn by a person; a fluid-based biometric sensor which is held by the housing; and a data processor which receives data from the fluid-based biometric sensor, wherein this data is analyzed to measure the person's biometric parameter levels. In another example, a biometric wearable device can have one or more fluid-based sensors (e.g. microfluidic channels). In an example, a biometric wearable device can include a power source such as a battery and/or and energy-harvesting unit. In another example, a biometric wearable device can transduce, harvest, and/or generate electricity from body thermal energy.

In an example, a biometric wearable device can be made from fabric woven from first and second electroconductive threads, wherein these threads create an electromagnetic field which can be used to measure the permittivity of nearby body tissue which, in turn, can be used to estimate biometric parameter levels. In an example, a biometric wearable device can have a flexible array of radiowave or microwave antennas which bend and/or stretch to conform to the arcuate surface of a person's body. In another embodiment, some portions or sections of a biometric wearable device can be relatively flexible and other portions or sections of the device can be rigid.

In an example, a biometric wearable device can be changed from a first level of operation to a second level of operation based on environmental changes detected by an environmental sensor. In another embodiment, a biometric wearable device can further comprise one or more other sensors selected from the group consisting of: accelerometer, gyroscope, other inertial sensor, goniometer, bend sensor, stretch sensor, pressure sensor, GPS sensor, jaw motion sensor, and other motion sensor. In an example, the operation of a biometric wearable device can be adjusted based on a change in a person's body temperature and/or environmental temperature. In another embodiment, the operation of a biometric wearable device can be automatically adjusted by one or more actuators in response to changes in moisture.

In an example, a biometric wearable device can further comprise a wireless data transmitter and/or data receiver. In another example, a biometric wearable device can further comprise a data processor, a battery and/or energy harvesting unit, a data transmitter, and a data receiver. In various examples, a biometric wearable device can be in wireless communication with a separate device selected from the group consisting of: cell phone, electronic tablet, electronically-functional eyewear, home electronics portal, laptop computer, drug pump, and smart utensil.

In an example, a biometric wearable device can provide feedback to a person wearing the device wherein this feedback is selected from the group consisting of: feedback concerning food consumption (such as types and amounts of foods, ingredients, and nutrients consumed, calories consumed, calories expended, and net energy balance during a period of time); information about good or bad ingredients in nearby food; information concerning financial incentives or penalties associated with acts of food consumption and achievement of health-related goals; information concerning progress toward meeting a weight, energy-balance, and/or other health-related goal; information concerning the calories or nutritional components of specific food items; and number of calories consumed per eating event or time period.

In another example, data from an energy (e.g. radiowave or microwave) receiver can be analyzed using artificial intelligence and/or machine learning to measure a person's biometric parameter levels. In an example, data from an energy (e.g. radiowave or microwave) receiver can be analyzed using a method selected from the group consisting of: Empirical Mode Decomposition (EMD), Factor Analysis (FA), Fast Fourier Transform (FFT), Feature vector Analysis (FVA), Fisher Linear Discriminant, Fourier Transformation (FT) Method, Fuzzy Logic (FL) Modeling, Gaussian Model (GM), and Generalized Auto-Regressive Conditional Heteroscedasticity (GARCH) Modeling. In another example, data from an energy (e.g. radiowave or microwave) receiver can be analyzed using a method selected from the group consisting of: Non-Linear Programming, Non-negative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Regression Model, and Signal Amplitude (SA).

In an example, a biometric wearable device can be embodied in a bracelet or bangle. In an example, a biometric wearable device can be embodied in a sock. In an example, a biometric wearable device can be embodied in an armlet or arm band. In an example, a biometric wearable device can comprise: a finger ring; an energy (e.g. radiowave or microwave) emitter/transmitter on the finger ring; an radiowave or microwave energy (e.g. radiowave or microwave) receiver on the finger ring; a power source; a data processor; and a data transmitter. In an example, a body part on which a biometric wearable device is worn can be a person's wrist. In an example, a biometric wearable device can be embodied in a finger ring, smart watch, wrist band, watch band, arm band, or ear-worn device.

In an example, a measured biometric parameter can be body hydration level. In another example, a measured biometric parameter can be heart rate. In an example, the biometric parameter which is measured by a biometric wearable device can be a person's body hydration level. In another example, the biometric parameter which is measured by a biometric wearable device can be a person's oxygenation level. In an example, a biometric wearable device can have a radiowave or microwave energy emitting pole and a radiowave or microwave energy receiving pole. In another example, a biometric wearable device can measure biometric parameter levels by measuring how radiowave or microwave energy emitted by an energy (e.g. radiowave or microwave) emitter/transmitter interacts with body tissue between the energy (e.g. radiowave or microwave) emitter/transmitter and an energy (e.g. radiowave or microwave) receiver.

In an example, an energy (e.g. radiowave or microwave) emitter/transmitter can comprise an antenna. In an example, a biometric wearable device can comprise a radiowave or microwave antenna which is configured to emit/transmit radiowave or microwave and receive radiowave or microwave energy. In an example, a biometric parameter management system can comprise a non-invasive (e.g. radiowave or microwave) glucose sensor and a wearable insulin pump which are in wireless communication with each other. In an example, a biometric wearable device can be part of a system which further comprises a smart phone, mobile phone, cell phone, electronic tablet, other flat-surface mobile electronic device, or smart eyewear. In another embodiment, a wearable pump can deliver a glucose-level-modifying substance into a person's body.

In an example, a glucose management system can comprise: a biometric wearable sensor (e.g. finger ring, smart watch, or wrist band) worn by a person, wherein the sensor further comprises an array of energy (e.g. radiowave or microwave) emitters/transmitters and energy (e.g. radiowave or microwave) receivers around a circumference of the sensor; and a wearable pump which delivers a glucose-level-modifying substance (e.g. insulin) into the person's body based on data from the energy receivers. In an example, a biometric wearable device can have a straight-line radiowave or microwave antenna. In another example, a biometric wearable device can have a quadrilateral radiowave or microwave antenna. In an example, a biometric wearable device can have a square radiowave or microwave antenna.

In another example, a biometric wearable device can have an arcuate energy (e.g. radiowave or microwave) emitter/transmitter and/or an arcuate energy (e.g. radiowave or microwave) receiver with a conic section shape. In an example, a biometric wearable device can have a comb-shaped radiowave or microwave antenna. In another example, a biometric wearable device can have a radiowave or microwave antenna comprising nested (e.g. concentric) rings. In an example, a biometric wearable device can have an octagonal radiowave or microwave antenna. In an example, a biometric wearable device can have a ring-shaped radiowave or microwave antenna. In an example, a biometric wearable device can have an undulating (e.g. sinusoidal and/or serpentine) radiowave or microwave antenna.

In an example, a biometric wearable device can comprise a spiral-shaped energy (e.g. radiowave or microwave) emitter/transmitter. In an example, a biometric wearable device can have a double spiral radiowave or microwave antenna. In an example, a biometric wearable device can have a spiral energy (e.g. radiowave or microwave) emitter/transmitter which is substantially parallel to the surface of a person's body. In an example, a biometric wearable device can have a spiral radiowave or microwave antenna. In an example, a biometric wearable device can include a spiral-shaped energy (e.g. radiowave or microwave) emitter/transmitter. In another example, a biometric wearable device can include two nested and/or intertwined spiral antennae.

In an example, a biometric wearable device can have a T-shaped radiowave or microwave antenna. In another example, a biometric wearable device can have a U-shaped radiowave or microwave antenna. In an example, a biometric wearable device can have a target-pattern-shaped radiowave or microwave antenna. In another example, a biometric wearable device can comprise: a first coil which emits/transmits electromagnetic (e.g. radiowave or microwave) energy; and a second coil which receives electromagnetic (e.g. radiowave or microwave) energy; wherein the first coil and the second coil are in different planes. In an example, a biometric wearable device can comprise: a first coil which emits/transmits electromagnetic (e.g. radiowave or microwave) energy; and a second coil which receives electromagnetic (e.g. radiowave or microwave) energy; wherein the first coil and the second coil are parallel.

In an example, a biometric wearable device can have a dumbbell or dog bone shaped radiowave or microwave antenna. In another embodiment, a biometric wearable device can have a radiowave or microwave probe. In an example, a biometric wearable device can have an arcuate energy (e.g. radiowave or microwave) emitter/transmitter and/or an arcuate energy (e.g. radiowave or microwave) receiver with a saddle shape. In an example, a biometric wearable device can have a sinusoidal radiowave or microwave antenna. In an example, a biometric wearable device can have a triangular radiowave or microwave antenna.

In an example, a biometric wearable device can comprise an energy (e.g. radiowave or microwave) emitter/transmitter with a shape selected from the group consisting of: rectangular cylinder, rectangular spiral, ring, ring between two EM wave (e.g. radiowave or microwave) poles, saddle shape, sawtooth shape, sinusoidal wave, sphere, spit ring, square, square spiral, and square wave. In another example, a biometric wearable device can comprise an energy (e.g. radiowave or microwave) receiver with a shape selected from the group consisting of: conic section, convex lens shape, cube shape, cylinder, cylindrical band, dumbbell, ellipse, hemisphere, hexagon, H-shape antenna, microstrip, nested rings, non-equilateral polygon, octagon, Omega-shape, oval, oval spiral, parallel rings, polygon with rounded vertices, polygonal spiral, quadrilateral, rectangle, and rectangular cylinder.

In an example, a biometric wearable device can comprise one or more radiowave or microwave energy antennae with shapes selected from the group consisting of: bulls eye pattern, arc of a circle, circle, circular spiral, coaxial probe, comb shape, concentric rings, and conic section. In another example, a biometric wearable device can comprise one or more radiowave or microwave energy antennae with shapes selected from the group consisting of: S-shape, stacked rings, straight co-linear poles, straight line, target pattern, triangle, T-shape, two complementary sinusoidal shapes, two intertwined spirals, two symmetric spirals, U-shape, Y-shape, and zigzag pattern. In an example, an energy (e.g. radiowave or microwave) emitter/transmitter in a biometric wearable device can have an oval shape.

In another example, a biometric wearable device can have an array, matrix, or series of EM wave (e.g. radiowave or microwave) spectrometers with a selected progression of different sizes (e.g. smaller to larger), shapes (e.g. less arcuate to more arcuate), gaps (e.g. closer together to farther apart), material compositions, and/or rotations. In an example, a biometric wearable device can have an array, matrix, or series of energy (e.g. radiowave or microwave) receivers with a selected progression of different sizes (e.g. smaller to larger), shapes (e.g. less arcuate to more arcuate), gaps (e.g. closer together to farther apart), material compositions, and/or rotations.

In an example, a biometric wearable device can comprise an array of energy (e.g. radiowave or microwave) emitters/transmitters and energy (e.g. radiowave or microwave) receivers, wherein the distance between energy emitters/transmitters and energy receivers varies (e.g. increases monotonically) with distance along an axis of the array. In an example, a first energy (e.g. radiowave or microwave) emitter/transmitter can be separated from a second energy (e.g. radiowave or microwave) emitter/transmitter by a selected distance.

In an example, a biometric wearable device can automatically sequence the emission of radiowave or microwave energy emitted from multiple energy (e.g. radiowave or microwave) emitters/transmitters in order to scan different tissue regions or depths. In an example, a biometric wearable device can include: a plurality of energy (e.g. radiowave or microwave) emitters/transmitters; and a plurality of energy (e.g. radiowave or microwave) receivers; wherein activation of energy emitters is multiplexed. In an example, a plurality of energy (e.g. radiowave or microwave) emitters/transmitters can emit radiowave or microwave energy in a selected chronological sequence and/or timing pattern. In an example, different antennae or different sections of an antenna can be activated to emit (radiowave or microwave) energy at different times, enabling multiplexing of energy signals and tissue scanning.

In another example, a biometric wearable device can comprise: a first antenna which emits/transmits radiowave or microwave energy; and a second antenna which receives this energy; wherein the first and second antenna are perpendicular to each other. In an example, a biometric wearable device can comprise: a first antenna which emits/transmits radiowave or microwave energy; and a second antenna which receives this energy; wherein the first and second antenna are parallel to each other. In another example, a biometric wearable device can have a radiowave or microwave antenna which is substantially parallel to the surface of a person's body. In another embodiment, a biometric wearable device can have an energy (e.g. radiowave or microwave) emitter/transmitter which is substantially parallel to the surface of a person's body. In another example, the longitudinal axis of an energy (e.g. radiowave or microwave) emitter/transmitter can be parallel to the longitudinal axis of an energy (e.g. radiowave or microwave) receiver.

In an example, a biometric wearable device can comprise: a first antenna with a first longitudinal axis, wherein the first antenna emits/transmits radiowave or microwave energy; and a second antenna with a second longitudinal axis, wherein the second antenna receives this energy; wherein the first and second longitudinal axes are colinear. In an example, a biometric wearable device can have an energy (e.g. radiowave or microwave) emitter/transmitter and an energy (e.g. radiowave or microwave) receiver which are co-linear. In an example, a biometric wearable device can comprise: a first antenna which emits/transmits radiowave or microwave energy; and a second antenna which receives this energy; wherein the first and second antenna are in different planes. In an example, a biometric wearable device can have a co-planar array, matrix, or series of energy (e.g. radiowave or microwave) emitters/transmitters and/or receivers.

In an example, the portions of the perimeter of an energy (e.g. radiowave or microwave) emitter/transmitter and the perimeter of an energy (e.g. radiowave or microwave) receiver which are closest to each other can be separated by a constant distance. In an example, a biometric wearable device can comprise: a circular, elliptical, or oval energy (e.g. radiowave or microwave) emitter/transmitter; and a circular, elliptical, or oval energy (e.g. radiowave or microwave) receiver; wherein the energy emitter and the energy receiver are nested. In an example, a biometric wearable device can comprise: a convex first radiowave or microwave antenna; and a convex second radiowave or microwave antenna; wherein the first antenna and the second antenna are nested. In an example, a biometric wearable device can comprise: an energy (e.g. radiowave or microwave) emitter/transmitter with a first longitudinal axis; and an energy (e.g. radiowave or microwave) receiver with a second longitudinal axis; wherein the first longitudinal axis and the second longitudinal axis are colinear.

In another example, a biometric wearable device can comprise: a first energy (e.g. radiowave or microwave) emitter/transmitter with a first polarity vector; a second energy (e.g. radiowave of microwave) emitter/transmitter with a second polarity vector, wherein the second polarity vector is different than the first polarity vector. In an example, a biometric wearable device can comprise: an energy (e.g. radiowave or microwave) emitter/transmitter with a first polarity vector; an energy (e.g. radiowave of microwave) receiver with a second polarity vector, wherein the second polarity vector is in the opposite direction from the first polarity vector.

In another example, a biometric wearable device can comprise: an energy (e.g. radiowave or microwave) emitter/transmitter with a first shape; and an energy (e.g. radiowave or microwave) receiver with a second shape; wherein the second shape is more convoluted and/or undulating than the first shape. In an example, a biometric wearable device can comprise: first radiowave or microwave antenna with a first shape; and second radiowave or microwave antenna with a second shape; wherein the second shape is different than the first shape. In another example, a biometric wearable device can comprise: first radiowave or microwave antenna with a first shape; and second radiowave or microwave antenna with a second shape; wherein the first shape is more arcuate and/or rounded than the second shape. In an example, an energy (e.g. radiowave or microwave) emitter/transmitter and energy (e.g. radiowave or microwave) receiver can have sinusoidally-complementary shapes. In an example, the ends of an energy (e.g. radiowave or microwave) emitter/transmitter and an energy (e.g. radiowave or microwave) receiver which face each other can have the same shape.

In an example, a biometric wearable device can comprise: an energy (e.g. radiowave or microwave) emitter/transmitter with a first size; and an energy (e.g. radiowave or microwave) receiver with a second size; wherein the first size is at least 20% greater than the second size. In an example, a biometric wearable device can comprise: an energy (e.g. radiowave or microwave) emitter/transmitter with a first length; and an energy (e.g. radiowave or microwave) receiver with a second length; wherein the first length is greater than the second length. In an example, a biometric wearable device can comprise: first radiowave or microwave antenna with a first size; and second radiowave or microwave antenna with a second size; wherein the first size is at least 20% greater than the second size. In another embodiment, a biometric wearable device can comprise: first radiowave or microwave antenna with a first length; and second radiowave or microwave antenna with a second length; wherein the first length is greater than the second length.

In an example, an energy (e.g. radiowave or microwave) emitter/transmitter and an energy (e.g. radiowave or microwave) receiver can be symmetric with respect to a line bisecting the gap between them. In another example, a biometric wearable device can comprise an array, matrix, or series of biometric sensors (e.g. radiowave or microwave energy emitters and/or receivers) with a progression of different sizes, shapes, and/or orientations. In an example, a biometric wearable device can have a rectangular array, grid, and/or matrix of radiowave or microwave energy transmitters and/or receivers. In another example, a biometric wearable device can have an arcuate energy (e.g. radiowave or microwave) emitter/transmitter and an arcuate energy (e.g. radiowave or microwave) receiver which are contained within an arcuate circular band or ring which is worn around a portion of a person's body. In an example, an array of energy (e.g. radiowave or microwave) emitters/transmitters and energy (e.g. radiowave or microwave) receivers can have a cylindrical and/or ring shape. In another example, an array of energy (e.g. radiowave or microwave) emitters/transmitters and energy (e.g. radiowave or microwave) receivers can have a saddle shape.

In an example, a biometric wearable device (e.g. a smart watch) can comprise: a strap or band which spans a portion of the circumference of a person's arm; an enclosure attached to strap or band; and a two-dimensional sensor array on the enclosure, wherein sensors in this two-dimensional array differ in location along a device circumference and differ in location along axes which are perpendicular to the circumference. In an example, a biometric wearable device (e.g. for non-invasive glucose monitoring) can comprise: an attachment member, such as a strap or band, which is configured to span at least a portion of the circumference of a person's arm; an enclosure which is part of (or attached to) the attachment member; and a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device.

In an example, a biometric wearable device can comprise a coplanar array of energy (e.g. radiowave or microwave) emitters and receivers with different sizes, different shapes, and/or different rotations/orientations. In an example, a biometric wearable device can comprise a planar array of alternating energy (e.g. radiowave or microwave) emitters/transmitters and energy (e.g. radiowave or microwave) receivers. In an example, a biometric wearable device can comprise a sequence of sets of electromagnetic sensors, wherein each set further comprises at least one energy (e.g. radiowave or microwave) emitter/transmitter and at least one energy (e.g. radiowave or microwave) receiver. In an example, a biometric wearable device can comprise a two-dimensional array of energy emitters and energy receivers which is part of a housing which is attached to a wearable arcuate band.

In an example, a biometric wearable device can comprise an array, matrix, or series of antennae with a selected progression of different sizes (e.g. smaller to larger), shapes (e.g. less arcuate to more arcuate), gaps (e.g. closer together to farther apart), material compositions, and/or rotations. In an example, a biometric wearable device can comprise an array, matrix, or series of energy (e.g. radiowave or microwave) emitters and receivers with a selected progression of different sizes (e.g. smaller to larger), shapes (e.g. less arcuate to more arcuate), gaps (e.g. closer together to farther apart), material compositions, and/or rotations. In an example, a biometric wearable device can have a central energy (e.g. radiowave or microwave) receiver and a plurality of energy (e.g. radiowave or microwave) emitters/transmitters around the central energy (e.g. radiowave or microwave) receiver.

In another example, a biometric wearable device can have an linear alternating sequence of energy (e.g. radiowave or microwave) emitters/transmitters and energy (e.g. radiowave or microwave) receivers. In another embodiment, an annular biometric wearable device can have a circumferential array of energy (e.g. radiowave or microwave) emitters/transmitters and energy (e.g. radiowave or microwave) receivers. In another example, an array of energy (e.g. radiowave and microwave) emitters/transmitters and energy (e.g. radiowave and microwave) receivers can comprise a plurality of triads of energy emitters and energy receivers, wherein each triad further comprises one energy emitter and two energy receivers, and wherein triads are aligned along circumferential lines of the device.

In an example, an array of energy (e.g. radiowave and microwave) emitters/transmitters and energy (e.g. radiowave and microwave) receivers can comprise a plurality of triads of energy emitters and receivers, wherein each triad further comprises two energy emitters and one energy receiver, and wherein triads are aligned along proximal-to-distal (e.g. perpendicular to circumferential) lines of the device. In another example, an array of energy (e.g. radiowave and microwave) emitters/transmitters and energy (e.g. radiowave and microwave) receivers can comprise a plurality of sets of energy emitters and energy receivers, wherein each set further comprises a central energy emitter surrounded by multiple energy receivers. In an example, sensors in a two-dimensional sensor array can be electromagnetic energy sensors which are each configured to measure parameters and/or patterns of electromagnetic energy passing through (and/or emitted by) tissue (of a person's arm).

In an example, a biometric wearable device can comprise a circumferential array of energy (e.g. radiowave or microwave) emitters/transmitters and energy (e.g. radiowave or microwave) receivers, wherein the distance between energy emitters/transmitters and energy receivers varies (e.g. increases) with distance around (a portion of) the circumference of the array. In an example, a biometric wearable device can comprise: an energy (e.g. radiowave or microwave) emitter/transmitter at a first location on the circumference of a device worn around a body part (e.g. a finger ring or smart watch); and an energy (e.g. radiowave or microwave) receiver at a second location on the circumference, wherein the first and second locations are on opposite sides (e.g. separated by 170 to 190 degrees) of the circumference. In an example, a plurality of biometric wearable sensors can be stacked along a virtual vector which extends radially outward from the cross-sectional center of a body member.

In an example, a biometric wearable device can comprise: an annular device worn around a body part; a biometric sensor on the device; a first actuator whose movement moves the biometric sensor along an X axis which is tangential to the circumference of the device; and a second actuator whose movement moves the biometric sensor along an Y axis which is perpendicular to the X axis. In an example, a biometric wearable device can include one or more electromagnetic (e.g. solenoid) actuators which change the location, position, and/or orientation of an energy (e.g. radiowave or microwave) emitter/transmitter and/or an energy (e.g. radiowave or microwave) receiver. In an example, a biometric wearable device can include one or more actuators which change the radial location of an energy (e.g. radiowave or microwave) emitter/transmitter and/or an energy (e.g. radiowave or microwave) receiver. In another example, a biometric wearable device can include one or more actuators which change the angle between a surface of a person's body and an energy (e.g. radiowave or microwave) emitter/transmitter and/or an energy (e.g. radiowave or microwave) receiver.

In an example, a biometric wearable device can comprise: an energy (e.g. radiowave or microwave) emitter/transmitter with a first longitudinal axis; an energy (e.g. radiowave or microwave) receiver with a second longitudinal axis; and an actuator; wherein the actuator selectively and/or cyclically changes the angle between virtual extensions of the first and second longitudinal axes. In another example, a biometric wearable device can have actuators which automatically adjust the angles between one or more energy (e.g. radiowave or microwave) emitters/transmitters and a body part. In an example, a biometric wearable device can further comprise one or more actuators which automatically adjust its internal configuration in order to more accurately and consistently measure a biometric parameter level.

In another example, a biometric wearable device can automatically adjust the distance (e.g. gap) between an energy (e.g. radiowave or microwave) emitter/transmitter and an energy (e.g. radiowave or microwave) receiver based on movement of the person's body. In an example, a biometric wearable device can automatically adjust the distance (e.g. gap) between an energy (e.g. radiowave or microwave) emitter/transmitter and an energy (e.g. radiowave or microwave) receiver in order to measure the levels of different biometric parameters. In an example, a biometric wearable device can have actuators which selectively-adjust and/or cyclically-change the pressure between one or more energy (e.g. radiowave or microwave) emitters/transmitters and the surface of a body part. In an example, a biometric wearable device can have actuators which selectively-adjust and/or cyclically-change the distance between one or more energy (e.g. radiowave or microwave) receivers and the surface of a body part.

In an example, a biometric wearable device can comprise: an actuator; one or more energy (e.g. radiowave or microwave) emitters/transmitters; and one or more energy (e.g. radiowave or microwave) receivers; wherein the emitters/transmitters and/or the receivers are moved by the actuator to scan different tissue regions and/or depths. In an example, a biometric wearable device can comprise: an actuator; one or more energy (e.g. radiowave or microwave) emitters/transmitters; and one or more energy (e.g. radiowave or microwave) receivers; wherein the emitters/transmitters and/or the receivers are moved by the actuator to change the geometric configuration of the emitters/transmitters and/or the receivers in order to scan through a range of tissue depths, locations, and/or types to measure a biometric parameter level more accurately.

In an example, a biometric wearable device can comprise: an annular housing (e.g. ring or band) which is worn around the circumference of a body part; a radiowave or microwave antenna; and an actuator (e.g. electromagnetic or MEMS actuator); wherein the actuator changes the radial, clock, and/or compass location of the radiowave or microwave antenna on the circumference of the housing. In another embodiment, a biometric wearable device can further comprise an actuator which automatically adjusts the distance (e.g. gap) between an energy (e.g. radiowave or microwave) emitter/transmitter and an EM wave energy (e.g. radiowave or microwave) receiver. In another example, a biometric wearable device can further comprise one or more actuators which automatically adjust its location, orientation, position relative to a body part in order to more accurately and consistently measure a biometric parameter level.

In an example, a biometric wearable device can further comprise one or more actuators which automatically change the radial locations of energy (e.g. radiowave or microwave) emitters/transmitters and/or energy (e.g. radiowave or microwave) receivers in order to more accurately and consistently measure biometric parameter levels. In another example, the location or shape of an energy (e.g. radiowave or microwave) emitter/transmitter on a biometric wearable device can be adjusted automatically (in an iterative manner) by the device in order to more accurately measure biometric parameter level for a specific person, for a specific type of activity, or for a specific configuration of the device relative to the person's body surface.

In another embodiment, a biometric wearable device can automatically change the size or shape of an energy (e.g. radiowave or microwave) receiver. In another example, a biometric wearable device can comprise: an energy (e.g. radiowave or microwave) emitter/transmitter; an energy (e.g. radiowave or microwave) receiver; and an actuator; wherein the actuator automatically increases the size and/or length of the energy emitter/transmitter. In an example, a biometric wearable device can comprise: an energy (e.g. radiowave or microwave) emitter/transmitter; an energy (e.g. radiowave or microwave) receiver; and an actuator; wherein the actuator automatically varies the size and/or length of the energy receiver in a cyclical manner. In an example, a biometric wearable device can further an actuator which automatically adjusts the size or shape of an energy (e.g. radiowave or microwave) emitter/transmitter and/or an radiowave or microwave energy (e.g. radiowave or microwave) receiver.

In an example, biometric sensors (e.g. electromagnetic energy emitters and/or receivers) which are closer to a ventral surface of a body part can have a first size, shape, and/or orientation and biometric sensors which are further from the ventral surface of the body part can have a second size, shape, and/or orientation. In an example, a biometric wearable device can have: a first annular component (e.g. ring or band) which spans the circumference of a body part; a second annular component (e.g. ring or band) which spans the circumference, wherein the first annular component and the second annular component are connected to each other by a mechanism that enables the second annular component to be rotated relative to the first band; and at least one energy (e.g. radiowave or microwave) emitter/transmitter and at least one energy (e.g. radiowave or microwave) receiver on the second annular component.

In an example, a biometric wearable device can selectively and/or cyclically change the strength and/or power of an energy field created by one or more energy (e.g. radiowave or microwave) emitters/transmitters. In an example, the power and/or current of radiowave or microwave energy emitted from an energy (e.g. radiowave or microwave) emitter/transmitter can be changed in response to specific environmental conditions (e.g. temperature or humidity) and/or specific activities in which the person wearing a device is engaged (e.g. high level of movement, eating, sleeping, etc.).

In an example, a biometric wearable device can automatically adjust and/or cyclically vary the wavelength and/or frequency of radiowave or microwave energy emitted from an energy (e.g. radiowave or microwave) emitter/transmitter in order to scan different tissue regions or depths. In an example, a biometric wearable device can comprise a variable-frequency radiowave or microwave energy source. In an example, a biometric wearable device can comprise an energy (e.g. radiowave or microwave) emitter/transmitter which emits/transmits energy with sequence of increasing radiowave or microwave frequencies (within a selected frequency range) in order to scan for different substances in a body part.

In another example, a biometric wearable device can emit radiowave or microwave energy at varying frequencies to collect data on the radiowave or microwave energy interaction between that energy and body tissue at different frequencies. In an example, a biometric wearable device can have a multi-band antenna for radiowave or microwave energy transmission. In another example, a biometric wearable device can sweep through a selected range of radiowave or microwave frequencies. In an example, the frequency and/or wavelength of radiowave or microwave energy emitted from an energy (e.g. radiowave or microwave) emitter/transmitter can be changed in response to specific environmental conditions (e.g. temperature or humidity) and/or specific activities in which the person wearing a device is engaged (e.g. high level of movement, eating, sleeping, etc.). In another example, a biometric wearable device can be a spectroscopic device which collects information about electromagnetic interaction between (radiowave or microwave) energy and body tissue at multiple energy frequencies. In an example, a biometric wearable device can comprise a radiowave or microwave spectrometer.

In an example, a biometric wearable device array can have at least two sensor triads along a circumference of the device, wherein each sensor triad has an energy (e.g. radiowave or microwave) emitter/transmitter, an radiowave or microwave energy resonator, and an radiowave or microwave energy (e.g. radiowave or microwave) receiver. In an example, a biometric wearable device can comprise: an energy (e.g. radiowave or microwave) emitter/transmitter, an energy (e.g. radiowave or microwave) receiver, and a split-ring resonator between the emitter/transmitter and the receiver. In an example, a biometric wearable device can comprise: an energy (e.g. radiowave or microwave) emitter/transmitter with a first longitudinal axis, an energy (e.g. radiowave or microwave) receiver with a second longitudinal axis, and a split-ring resonator between the emitter/transmitter and the receiver, wherein the split (e.g. gap) in the resonator comprises between 10% and 30% of the circumference of the resonator.

In an example, a biometric wearable device can further comprise an electromagnetic resonator. In an example, a biometric wearable device can have a non-uniform array, matrix, or series of co-planar resonators. In another embodiment, a biometric wearable device can have a plurality of resonators with different resonant frequencies, thereby providing more rapid and/or complete information on the permittivity of nearby body tissue (and thus biometric parameter levels) across a selected range of radiowave or microwave frequencies than is possible with a single resonator. In an example, a biometric wearable device can have a saddle-shaped array, matrix, or series of resonators. In another embodiment, a biometric wearable device can have an array, matrix, or series of co-planar resonators, wherein there is a selected progression in resonator frequency from a lower resonant frequency to a higher resonant frequency along an axis of the array, matrix, or series.

In another example, a biometric wearable device can have an array, matrix, or series of electromagnetic resonators with a selected progression of different sizes (e.g. smaller to larger), shapes (e.g. less arcuate to more arcuate), gaps (e.g. closer together to farther apart), material compositions, and/or rotations. In an example, a biometric wearable device can have an electromagnetic resonator. In another example, a biometric wearable device can have two split ring resonators, wherein a first split ring resonator and a second split ring resonator are co-planar. In an example, a biometric wearable device can have: a first component which transmits radiowave or microwave energy; a second component which receives radiowave or microwave energy; and a third component between the first and second components which resonates in response to radiowave or microwave energy transmission.

In another example, a biometric wearable device can include one or more actuators which automatically adjust dimensions of a resonator for greater accuracy in measuring biometric parameter levels. In an example, a biometric wearable device including an electromagnetic resonator comprising a spit ring. In an example, a resonator can comprise two or more nested and/or concentric rings with spits or gaps in their circumferences. In an example, a resonator which is part of a biometric wearable device can be arcuate. In an example, a resonator which is part of a biometric wearable device can be square or rectangular. In an example, an electromagnetic resonator can be located between an energy (e.g. radiowave or microwave) emitter/transmitter and an energy (e.g. radiowave or microwave) receiver.

In an example, an electromagnetic resonator can comprise two or more nested rings. In another embodiment, resonators in a three-dimensional array, matrix, or series which are closer to the surface of a person's body can have a higher resonant frequency and resonators which are farther from the surface of the person's body can have a lower resonant frequency. In an example, resonators which are closer to the surface of a person's body can be larger and resonators which are farther from the surface of the person's body can be smaller. In another example, when a resonator resonates at a resonant frequency, the resonator acts as a partial short-circuit between an energy (e.g. radiowave or microwave) emitter/transmitter and an energy (e.g. radiowave or microwave) receiver.

In an example, a biometric wearable device can have a first (split ring) resonator with a first shape and a second (split ring) resonator with a second shape, wherein the second shape is different than the first shape. In another example, a biometric wearable device can have a first (split ring) resonator and a second (split ring) resonator, wherein the first and second (split ring) resonators are coplanar. In an example, a biometric wearable device can have a three-dimensional array, matrix, or series of split ring resonators. In another example, a resonator can be a Split Ring Resonator (SRR). In an example, a resonator which is part of a biometric wearable device can have a shape which is selected from the group consisting of: circular ring or band; concentric ring; target pattern; nested and/or concentric rings; ring with a single split or gap; ring with multiple splits (or gaps); and three-dimensionally stacked or parallel rings.

In an example, the one or more parameters of a resonator in a biometric wearable device that are automatically adjusted can be selected from the group consisting of: split (or gap) distance; inter-resonator distance in an array, matrix, or series of resonators; distance between a resonator and the surface of a person's body; angle between a resonator and the surface of a person's body; orientation of a resonator relative to the surface of a person's body; location of a resonator on a person's body (relative to anatomical landmarks such as vasculature); frequency of radiowave or microwave energy emitted; distance between a resonator and an energy (e.g. radiowave or microwave) emitter/transmitter or receiver; orientation of a resonator relative to an energy (e.g. radiowave or microwave) emitter/transmitter or receiver; and curvature of an array, matrix, or series of resonators.

In an example, a biometric wearable device can have a double-spiral resonator. In an example, a biometric wearable device can collect data on the permittivity of body tissue across a selected (sub)spectrum of radiowave or microwave frequencies. In another embodiment, a biometric wearable device can include a permittivity sensor. In an example, a biometric wearable device can measure changes in tissue permittivity. In an example, collecting data on the permittivity of body tissue across a range of radiowave or microwave frequencies can provide more accurate estimation of biometric parameter levels than collecting data on permittivity at a single frequency.

In an example, a biometric wearable device can comprise: an energy (e.g. radiowave or microwave) emitter/transmitter; an energy (e.g. radiowave or microwave) receiver; and a metal electromagnetic energy barrier (e.g. electromagnetic shield) between the energy emitter/transmitter and the energy receiver. In another example, a biometric wearable device can comprise: an energy (e.g. radiowave or microwave) emitter/transmitter; an energy (e.g. radiowave or microwave) receiver; and an electromagnetic energy barrier (e.g. electromagnetic shield) between the energy emitter/transmitter and the energy receiver; wherein the emitter/transmitter, the receiver, and the electromagnetic energy barrier are coplanar.

In an example, a biometric wearable device can comprise: an energy (e.g. radiowave or microwave) emitter/transmitter with a first length; an energy (e.g. radiowave or microwave) receiver with a second length; and an electromagnetic energy barrier (e.g. electromagnetic shield) with a third length between the energy emitter/transmitter and the energy receiver; wherein the third length is greater than either the first length or the second length. In another example, a biometric wearable device can have a central energy (e.g. radiowave or microwave) emitter/transmitter, a plurality of energy (e.g. radiowave or microwave) receivers around the central energy (e.g. radiowave or microwave) emitter/transmitter, and an arcuate (e.g. circular) electromagnetic energy barrier (e.g. electromagnetic shield) between the central energy (e.g. radiowave or microwave) emitter/transmitter and the plurality of energy (e.g. radiowave or microwave) receivers.

In an example, a biometric wearable device can include a linear electromagnetic energy barrier (e.g. electromagnetic shield). In another example, an electromagnetic energy barrier (e.g. electromagnetic shield) can be midway between an energy (e.g. radiowave or microwave) emitter/transmitter and an energy (e.g. radiowave or microwave) receiver. In an example, an electromagnetic energy barrier (e.g. electromagnetic shield) can reduce and/or block energy transmission directly from an energy (e.g. radiowave or microwave) emitter/transmitter to an energy (e.g. radiowave or microwave) receiver, apart from transmission through body tissue.

In an example, a biometric wearable device can comprise: an energy (e.g. radiowave or microwave) emitter/transmitter on a circumference of a device worn around a body part; an energy (e.g. radiowave or microwave) receiver on the circumference; and an arcuate (e.g. circumferential) track or channel around (a portion of) the circumference; wherein the radial location (e.g. polar coordinate, clock hour coordinate, and/or compass coordinate) of the emitter/transmitter and/or the receiver is changed by sliding the emitter/transmitter and/or the receiver slides along the arcuate (e.g. circumferential) track or channel. In an example, a biometric wearable device can have an arcuate (e.g. circumferential) track, channel, or slot; wherein the distance between an energy (e.g. radiowave or microwave) emitter/transmitter and an energy (e.g. radiowave or microwave) receiver can be changed by moving the energy (e.g. radiowave or microwave) emitter/transmitter, the energy (e.g. radiowave or microwave) receiver, or both along the track, channel, or slot.

In an example, a biometric wearable device can comprise: an arcuate band which spans the circumference of a body part an energy (e.g. radiowave or microwave) emitter/transmitter; an energy (e.g. radiowave or microwave) receiver; a fluid-based (e.g. microfluidic) sensor; a data processor; an energy source (e.g. battery); and a data transmitter. In an example, measurement of a biometric parameter level with a fluid-based (e.g. microfluidic) sensor can be used to calibrate measurement of the biometric parameter level with a radiowave or microwave sensor.

In an example, a biometric wearable device can transduce, harvest, and/or generate electricity from ambient radiowave or microwave energy. In another example, a biometric wearable device can be an article of clothing in which conductive threads or fibers have been incorporated to create a radiowave or microwave antenna. In an example, biometric wearable device can comprise: a first electroconductive thread or yarn in a woven fabric which functions as an energy (e.g. radiowave or microwave) emitter/transmitter; and a second electroconductive thread of yarn in a woven fabric which functions as an energy (e.g. radiowave or microwave) receiver.

In another example, a biometric wearable device comprise: a flexible energy (e.g. radiowave or microwave) emitter/transmitter; and a flexible arcuate EM wave energy (e.g. radiowave or microwave) receiver; wherein the emitter and receiver are configured to bend and conform to the curved surface of a person's body. In an example, some portions or sections of a biometric wearable device can be relatively flexible and other portions or sections of the device can be rigid, wherein biometric sensors (e.g. electromagnetic energy emitters or receivers) are located on the rigid portions.

In an example, a biometric wearable device can comprise: a radiowave or microwave energy emitter/transmitter; a radiowave or microwave energy receiver; a light energy emitter; and a light energy receiver; wherein data from the radiowave or microwave receiver and data from the light energy receiver are jointly analyzed to measure biometric parameter levels. In an example, a biometric wearable device can use both optical spectroscopy and radiowave (or microwave) spectroscopy to measuring biometric parameter levels. In an example, the operation of a biometric wearable device can be adjusted based on a change in a person's body movement speed, acceleration, orientation, or direction. In an example, the operation of a biometric wearable device can be automatically adjusted by one or more actuators in response to changes in temperature. In another example, a biometric wearable device can further comprise a graphic display component (display screen and/or coherent light projection). In an example, a biometric wearable device can further comprise a display screen.

In an example, a biometric wearable device can be part of a system for management of a biometric parameter, wherein this system provides feedback to the person wearing the device and wherein this feedback is selected from the group consisting of: advice concerning consumption of specific foods or suggested food alternatives (such as advice from a dietician, nutritionist, nurse, physician, health coach, other health care professional, virtual agent, or health plan); electronic verbal or written feedback (such as phone calls, electronic verbal messages, or electronic text messages); live communication from a health care professional; questions to the person that are directed toward better measurement or modification of food consumption; real-time advice concerning whether to eat specific foods and suggestions for alternatives if foods are not healthy; social feedback (such as encouragement or admonitions from friends and/or a social network); suggestions for meal planning and food consumption for an upcoming day; and suggestions for physical activity and caloric expenditure to achieve desired energy balance outcomes. In an example, a system for management of a biometric parameter can comprise: biometric wearable sensor worn by a person; and a behavior-modification (e.g. feedback) device which modifies the person's eating behavior, wherein the sensor is in wireless communication with the behavior-modification device.

In an example, data from an energy (e.g. radiowave or microwave) receiver can be analyzed using a method selected from the group consisting of: Analysis of Variance (ANOVA), Artificial Neural Network (ANN), Auto-Regressive (AR) Modeling, Bayesian Analysis, and Bonferroni Analysis (BA). In another example, data from an energy (e.g. radiowave or microwave) receiver can be analyzed using a method selected from the group consisting of: Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), and Kernel Estimation. In an example, data from an energy (e.g. radiowave or microwave) receiver can be analyzed using a method selected from the group consisting of: Signal Averaging, Signal Decomposition, Sine Wave Compositing, Singular Value Decomposition (SVD), Spine Function, Support vector and/ or Machine (SVM), Time Domain Analysis, Time Frequency Analysis, Time Series Model, Trained Bayes Classifier, Variance, Waveform Identification, Wavelet Analysis, and Wavelet Transformation.

Having completed the introductory section, this disclosure now specifically describes the examples shown in FIGS. 1 through 20. It is to be understood that variations from the introductory section can be applied to these example where relevant.

Figures 1, 2:
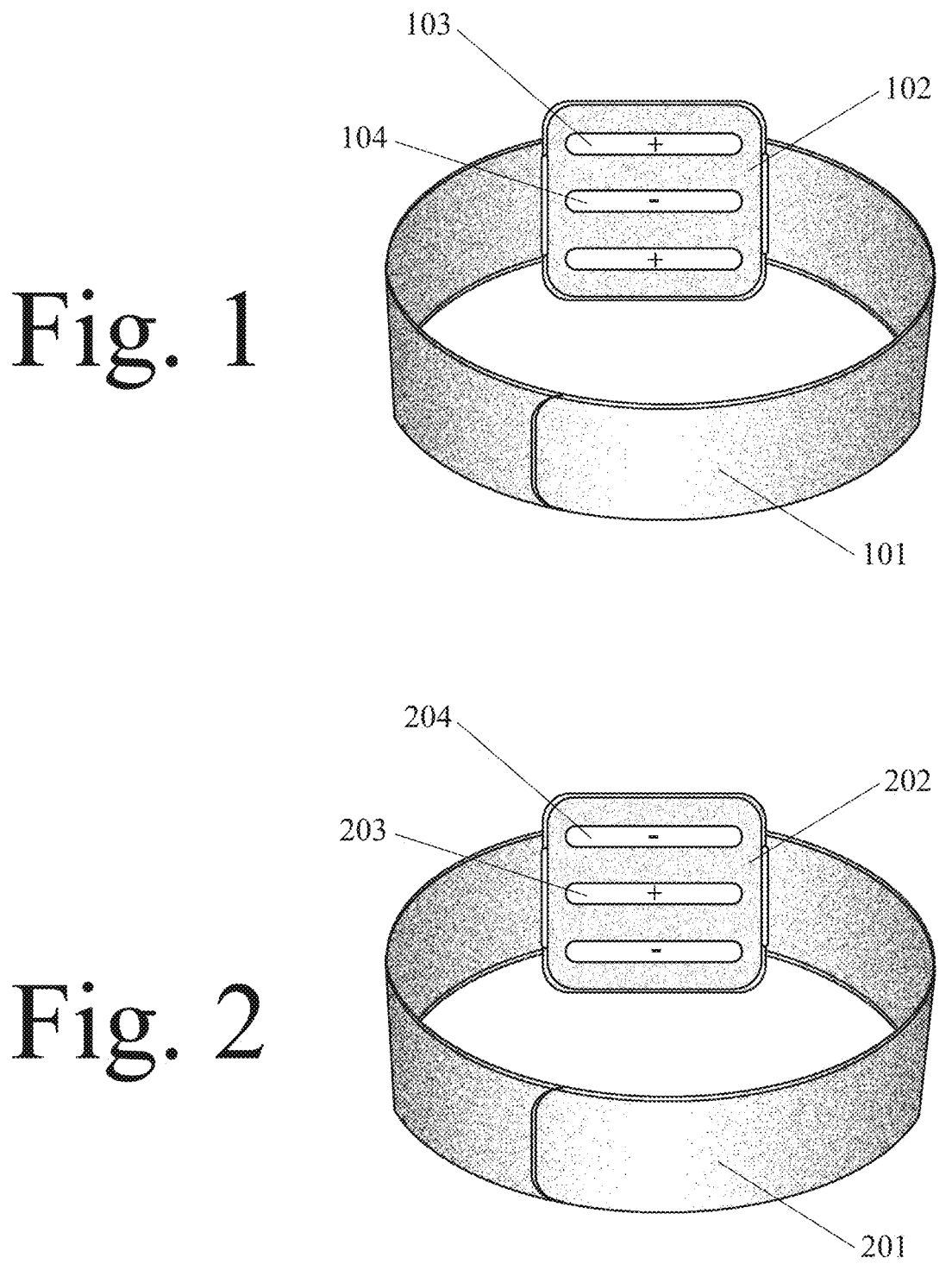

FIG. 1 shows an example of an biometric wearable device comprising: an arcuate band 101 which is configured to span (some or all of) the circumferential perimeter of a part of a person's body (such as a wrist, arm, finger, ankle, and/or leg); a housing 102 which is held on the person's body by the arcuate band; an energy emitter 103 (identified with a plus sign) which is configured to emit energy toward the part of the person's body, wherein the energy emitter is part of (e.g. on or in) the housing; and an energy receiver 104 (identified with a negative sign) which is configured to receive energy from the energy emitter after that energy has passed through and/or been reflected from the part of the person's body, wherein the energy receiver is part of (e.g. on or in) the housing.

In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location.

In an example, an electromagnetic energy emitter can emit electromagnetic energy into body tissue and an electromagnetic energy receiver can receive that electromagnetic energy after the electromagnetic energy has passed through the body tissue. In an example, an energy emitter and/or an energy receiver can be an antenna. In an example, an energy emitter can emit radiowave or microwave energy. In an example, an energy emitter and an energy receiver can be co-planar. In an example, an energy emitter and an energy receiver can be parallel. In an example, the longitudinal axis of an energy emitter can be parallel to the longitudinal axis of an energy receiver.

In this example, a longitudinal axis of an energy emitter and/or an energy receiver is parallel to a circumferential line (e.g. a line around a circumference of the device). In another example, a longitudinal axis of an energy emitter and/or an energy receiver can be perpendicular and/or orthogonal to a circumferential line. In an example, a device can further comprise energy emitters and/or energy receivers on the arcuate band as well as on the housing. In an example, a circumferential array of energy emitters and energy receivers, including those on a band as well as a housing, can collectively span between 60% and 90% of the circumference of the device.

In an example, a biometric wearable device can be a spectroscopic device which collects information about electromagnetic interaction between energy and body tissue at multiple energy frequencies. In an example, the energy emitter on a biometric wearable device can sweep through a range of energy frequencies. In an example, a biometric wearable device can comprise an array, matrix, or series of antennae with a selected progression of different sizes (e.g. smaller to larger), shapes (e.g. less arcuate to more arcuate), gaps (e.g. closer together to farther apart), material compositions, and/or rotations. In an example, a device can have different size or different shape energy emitters and/or energy receivers. In an example, a device can have nested energy emitters and/or energy receivers.

This figure can also be described as showing an example of a biometric wearable device comprising: an arcuate band which is configured to span (some or all of) the circumferential perimeter of a part of a person's body (such as a wrist, arm, finger, ankle, and/or leg); a first energy emitter (identified with a plus sign) which is configured to emit energy toward the part of the person's body; a second energy emitter (identified with a plus sign) which is configured to emit energy toward the part of the person's body; and an energy receiver (identified with a negative sign) which is configured to receive energy from the first energy emitter and/or the second energy emitter after that energy has passed through and/or been reflected from the part of the person's body, wherein the energy receiver is located between the first energy emitter and the second energy emitter. Relevant variations discussed elsewhere in this disclosure or in priority-linked disclosures can also be applied to this example.

FIG. 2 shows an example of an biometric wearable device comprising: an arcuate band 201 which is configured to span (some or all of) the circumferential perimeter of a part of a person's body (such as a wrist, arm, finger, ankle, and/or leg); a housing 202 which is held on the person's body by the arcuate band; an energy emitter 203 (identified with a plus sign) which is configured to emit energy toward the part of the person's body, wherein the energy emitter is part of (e.g. on or in) the housing; and an energy receiver 204 (identified with a negative sign) which is configured to receive energy from the energy emitter after that energy has passed through and/or been reflected from the part of the person's body, wherein the energy receiver is part of (e.g. on or in) the housing. In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location.

In an example, an electromagnetic energy emitter can emit electromagnetic energy into body tissue and an electromagnetic energy receiver can receive that electromagnetic energy after the electromagnetic energy has passed through the body tissue. In an example, an energy emitter and/or an energy receiver can be an antenna. In an example, an energy emitter can emit radiowave or microwave energy. In an example, an energy emitter and an energy receiver can be co-planar. In an example, an energy emitter and an energy receiver can be parallel. In an example, the longitudinal axis of an energy emitter can be parallel to the longitudinal axis of an energy receiver.

In this example, a longitudinal axis of an energy emitter and/or an energy receiver is parallel to a circumferential line (e.g. a line around a circumference of the device). In another example, a longitudinal axis of an energy emitter and/or an energy receiver can be perpendicular and/or orthogonal to a circumferential line. In an example, a device can further comprise energy emitters and/or energy receivers on the arcuate band as well as on the housing. In an example, a circumferential array of energy emitters and energy receivers, including those on a band as well as a housing, can collectively span between 60% and 90% of the circumference of the device.

In an example, a biometric wearable device can be a spectroscopic device which collects information about electromagnetic interaction between energy and body tissue at multiple energy frequencies. In an example, the energy emitter on a biometric wearable device can sweep through a range of energy frequencies. In an example, a biometric wearable device can comprise an array, matrix, or series of antennae with a selected progression of different sizes (e.g. smaller to larger), shapes (e.g. less arcuate to more arcuate), gaps (e.g. closer together to farther apart), material compositions, and/or rotations. In an example, a device can have different size or different shape energy emitters and/or energy receivers. In an example, a device can have nested energy emitters and/or energy receivers.

This figure can also be described as showing an example of a biometric wearable device comprising: an arcuate band which is configured to span (some or all of) the circumferential perimeter of a part of a person's body (such as a wrist, arm, finger, ankle, and/or leg); an energy emitter (identified with a plus sign) which is configured to emit energy toward the part of the person's body; a first energy receiver (identified with a negative sign) which is configured to receive energy from the energy emitter after that energy has passed through and/or been reflected from the part of the person's body; a second energy receiver (identified with a negative sign) which is configured to receive energy from the energy emitter after that energy has passed through and/or been reflected from the part of the person's body, wherein the energy emitter is located between the first energy receiver and the second energy receiver. Relevant variations discussed elsewhere in this disclosure or in priority-linked disclosures can also be applied to this example.

Figures 3, 4:
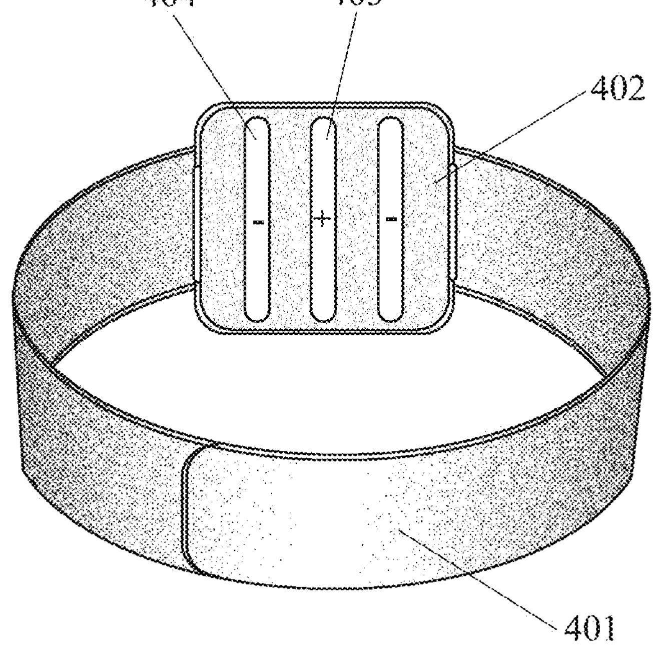
FIG. 3 shows a biometric wearable device with at least one radiowave or microwave energy emitter and at least one energy receiver on a housing, wherein the emitters and receivers are parallel to each other and perpendicular to a circumferential line around the device, and wherein an energy receiver is between energy emitters.
FIG. 4 shows a biometric wearable device with at least one radiowave or microwave energy emitter and at least one energy receiver on a housing, wherein the emitters and receivers are parallel to each other and perpendicular to a circumferential line around the device, and wherein an energy emitter is between energy receivers.

FIG. 3 shows an example of an biometric wearable device comprising: an arcuate band 301 which is configured to span (some or all of) the circumferential perimeter of a part of a person's body (such as a wrist, arm, finger, ankle, and/or leg); a housing 302 which is held on the person's body by the arcuate band; an energy emitter 303 (identified with a plus sign) which is configured to emit energy toward the part of the person's body, wherein the energy emitter is part of (e.g. on or in) the housing; and an energy receiver 304 (identified with a negative sign) which is configured to receive energy from the energy emitter after that energy has passed through and/or been reflected from the part of the person's body, wherein the energy receiver is part of (e.g. on or in) the housing. In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location.

In an example, an electromagnetic energy emitter can emit electromagnetic energy into body tissue and an electromagnetic energy receiver can receive that electromagnetic energy after the electromagnetic energy has passed through the body tissue. In an example, an energy emitter and/or an energy receiver can be an antenna. In an example, an energy emitter can emit radiowave or microwave energy. In an example, an energy emitter and an energy receiver can be co-planar. In an example, an energy emitter and an energy receiver can be parallel. In an example, the longitudinal axis of an energy emitter can be parallel to the longitudinal axis of an energy receiver.

In this example, a longitudinal axis of an energy emitter and/or an energy receiver is perpendicular and/or orthogonal to a circumferential line (e.g. a line around a circumference of the device). In another example, a longitudinal axis of an energy emitter and/or an energy receiver can be parallel to a circumferential line. In an example, a device can further comprise energy emitters and/or energy receivers on the arcuate band as well as on the housing. In an example, a circumferential array of energy emitters and energy receivers, including those on a band as well as a housing, can collectively span between 60% and 90% of the circumference of the device.

In an example, a biometric wearable device can be a spectroscopic device which collects information about electromagnetic interaction between energy and body tissue at multiple energy frequencies. In an example, the energy emitter on a biometric wearable device can sweep through a range of energy frequencies. In an example, a biometric wearable device can comprise an array, matrix, or series of antennae with a selected progression of different sizes (e.g. smaller to larger), shapes (e.g. less arcuate to more arcuate), gaps (e.g. closer together to farther apart), material compositions, and/or rotations. In an example, a device can have different size or different shape energy emitters and/or energy receivers. In an example, a device can have nested energy emitters and/or energy receivers.

This figure can also be described as showing an example of a biometric wearable device comprising: an arcuate band which is configured to span (some or all of) the circumferential perimeter of a part of a person's body (such as a wrist, arm, finger, ankle, and/or leg); a first energy emitter (identified with a plus sign) which is configured to emit energy toward the part of the person's body; a second energy emitter (identified with a plus sign) which is configured to emit energy toward the part of the person's body; and an energy receiver (identified with a negative sign) which is configured to receive energy from the first energy emitter and/or the second energy emitter after that energy has passed through and/or been reflected from the part of the person's body, wherein the energy receiver is located between the first energy emitter and the second energy emitter. Relevant variations discussed elsewhere in this disclosure or in priority-linked disclosures can also be applied to this example.

FIG. 4 shows an example of an biometric wearable device comprising: an arcuate band 401 which is configured to span (some or all of) the circumferential perimeter of a part of a person's body (such as a wrist, arm, finger, ankle, and/or leg); a housing 402 which is held on the person's body by the arcuate band; an energy emitter 403 (identified with a plus sign) which is configured to emit energy toward the part of the person's body, wherein the energy emitter is part of (e.g. on or in) the housing; and an energy receiver 404 (identified with a negative sign) which is configured to receive energy from the energy emitter after that energy has passed through and/or been reflected from the part of the person's body, wherein the energy receiver is part of (e.g. on or in) the housing. In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location.

In an example, an electromagnetic energy emitter can emit electromagnetic energy into body tissue and an electromagnetic energy receiver can receive that electromagnetic energy after the electromagnetic energy has passed through the body tissue. In an example, an energy emitter and/or an energy receiver can be an antenna. In an example, an energy emitter can emit radiowave or microwave energy. In an example, an energy emitter and an energy receiver can be co-planar. In an example, an energy emitter and an energy receiver can be parallel. In an example, the longitudinal axis of an energy emitter can be parallel to the longitudinal axis of an energy receiver.

In this example, a longitudinal axis of an energy emitter and/or an energy receiver is perpendicular and/or orthogonal to a circumferential line (e.g. a line around a circumference of the device). In another example, a longitudinal axis of an energy emitter and/or an energy receiver can be parallel to a circumferential line. In an example, a device can further comprise energy emitters and/or energy receivers on the arcuate band as well as on the housing. In an example, a circumferential array of energy emitters and energy receivers, including those on a band as well as a housing, can collectively span between 60% and 90% of the circumference of the device.

In an example, a biometric wearable device can be a spectroscopic device which collects information about electromagnetic interaction between energy and body tissue at multiple energy frequencies. In an example, the energy emitter on a biometric wearable device can sweep through a range of energy frequencies. In an example, a biometric wearable device can comprise an array, matrix, or series of antennae with a selected progression of different sizes (e.g. smaller to larger), shapes (e.g. less arcuate to more arcuate), gaps (e.g. closer together to farther apart), material compositions, and/or rotations. In an example, a device can have different size or different shape energy emitters and/or energy receivers. In an example, a device can have nested energy emitters and/or energy receivers.

This figure can also be described as showing an example of a biometric wearable device comprising: an arcuate band which is configured to span (some or all of) the circumferential perimeter of a part of a person's body (such as a wrist, arm, finger, ankle, and/or leg); an energy emitter (identified with a plus sign) which is configured to emit energy toward the part of the person's body; a first energy receiver (identified with a negative sign) which is configured to receive energy from the energy emitter after that energy has passed through and/or been reflected from the part of the person's body; a second energy receiver (identified with a negative sign) which is configured to receive energy from the energy emitter after that energy has passed through and/or been reflected from the part of the person's body, wherein the energy emitter is located between the first energy receiver and the second energy receiver. Relevant variations discussed elsewhere in this disclosure or in priority-linked disclosures can also be applied to this example.

Figure 5:
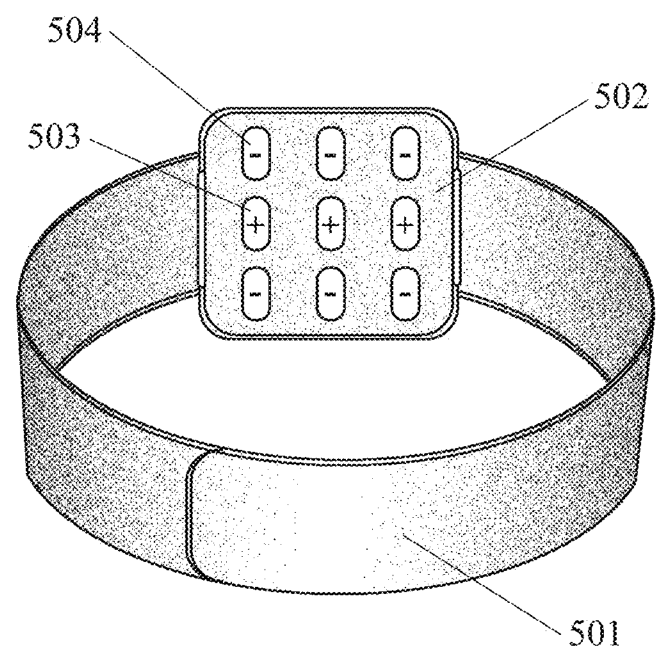
FIG. 5 shows a biometric wearable device with a two-dimensional array of radiowave or microwave energy emitters and receivers which differ in location along circumferential lines and along lines which are perpendicular to circumferential lines, wherein individual emitters and receivers are perpendicular to circumferential lines, and wherein energy emitters are between energy receivers.

FIG. 5 shows an example of a wearable device for the arm with a plurality of close-fitting biometric sensors comprising: an attachment member 501, such as a strap or band, which is configured to span at least a portion of the circumference of a person's arm; an enclosure 502 which is part of (or attached to) the attachment member; and a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device. This device comprises a two-dimensional array of energy emitters (including 503) and energy receivers (including 504) which is part of a housing (e.g. enclosure) attached to a wearable arcuate band.

In this example, sensors in the two-dimensional sensor array are electromagnetic energy sensors which measure parameters and/or patterns of electromagnetic energy passing through tissue of the person's arm. In this example, there are multiple triads of energy emitters and energy receivers and a triad is aligned along a proximal-to-distal line. In this example, there is one energy emitter and two energy receivers in a triad of energy emitters and energy receivers.

In this example, a longitudinal axis of an individual energy emitter and/or an individual energy receiver is perpendicular and/or orthogonal to a circumferential line (e.g. a line around a circumference of the device). In another example, a longitudinal axis of an individual energy emitter and/or an individual energy receiver can be parallel to a circumferential line. In an example, a device can further comprise energy emitters and/or energy receivers on the arcuate band as well as on the housing. In an example, a circumferential array of energy emitters and energy receivers, including those on a band as well as a housing, can collectively span between 60% and 90% of the circumference of the device. Relevant variations discussed elsewhere in this disclosure or in priority-linked disclosures can also be applied to this example.

Figure 6:
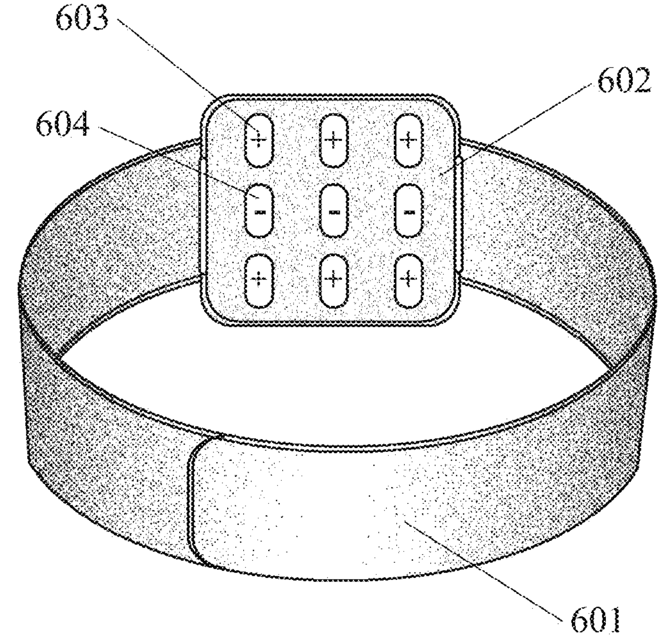
FIG. 6 shows a biometric wearable device with a two-dimensional array of radiowave or microwave energy emitters and receivers which differ in location along circumferential lines and along lines which are perpendicular to circumferential lines, wherein individual emitters and receivers are perpendicular to circumferential lines, and wherein energy receivers are between energy emitters.

FIG. 6 shows an example of a wearable device for the arm with a plurality of close-fitting biometric sensors comprising: an attachment member 601, such as a strap or band, which is configured to span at least a portion of the circumference of a person's arm; an enclosure 602 which is part of (or attached to) the attachment member; and a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device. This device comprises a two-dimensional array of energy emitters (including 603) and energy receivers (including 604) which is part of a housing (e.g. enclosure) attached to a wearable arcuate band.

In this example, sensors in the two-dimensional sensor array are electromagnetic energy sensors which measure parameters and/or patterns of electromagnetic energy passing through tissue of the person's arm. In this example, there are multiple triads of energy emitters and energy receivers and a triad is aligned along a proximal-to-distal line. In this example, there are two energy emitters and one energy receiver in a triad of energy emitters and energy receivers.

In this example, a longitudinal axis of an individual energy emitter and/or an individual energy receiver is perpendicular and/or orthogonal to a circumferential line (e.g. a line around a circumference of the device). In another example, a longitudinal axis of an individual energy emitter and/or an individual energy receiver can be parallel to a circumferential line. In an example, a device can further comprise energy emitters and/or energy receivers on the arcuate band as well as on the housing. In an example, a circumferential array of energy emitters and energy receivers, including those on a band as well as a housing, can collectively span between 60% and 90% of the circumference of the device. Relevant variations discussed elsewhere in this disclosure or in priority-linked disclosures can also be applied to this example.

Figure 7:
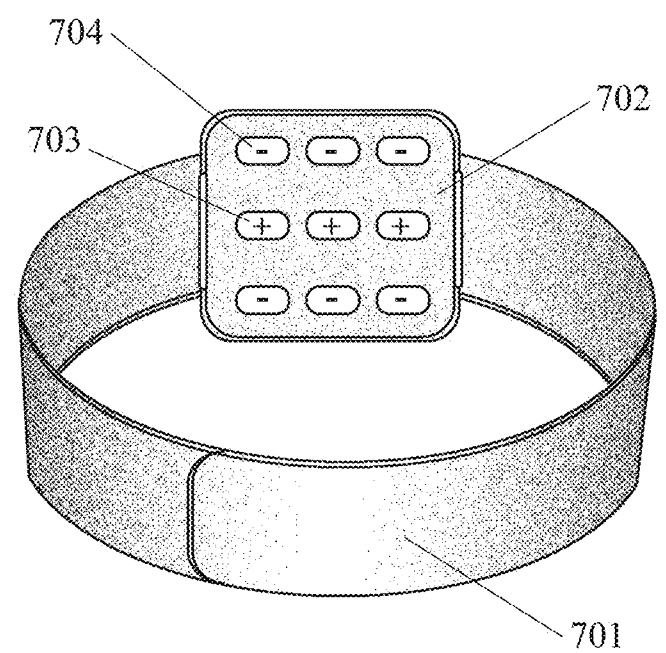
FIG. 7 shows a biometric wearable device with a two-dimensional array of radiowave or microwave energy emitters and receivers which differ in location along circumferential lines and along lines which are perpendicular to circumferential lines, wherein individual emitters and receivers are parallel to circumferential lines, and wherein energy emitters are between energy receivers.

FIG. 7 shows an example of a wearable device for the arm with a plurality of close-fitting biometric sensors comprising: an attachment member 701, such as a strap or band, which is configured to span at least a portion of the circumference of a person's arm; an enclosure 702 which is part of (or attached to) the attachment member; and a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device. This device comprises a two-dimensional array of energy emitters (including 703) and energy receivers (including 704) which is part of a housing (e.g. enclosure) attached to a wearable arcuate band.

In this example, sensors in the two-dimensional sensor array are electromagnetic energy sensors which measure parameters and/or patterns of electromagnetic energy passing through tissue of the person's arm. In this example, there are multiple triads of energy emitters and energy receivers and a triad is aligned along a proximal-to-distal line. In this example, there is one energy emitter and two energy receivers in a triad of energy emitters and energy receivers.

In this example, a longitudinal axis of an individual energy emitter and/or an individual energy receiver is parallel to a circumferential line (e.g. a line around a circumference of the device). In another example, a longitudinal axis of an individual energy emitter and/or an individual energy receiver can be perpendicular and/or orthogonal to a circumferential line. In an example, a device can further comprise energy emitters and/or energy receivers on the arcuate band as well as on the housing. In an example, a circumferential array of energy emitters and energy receivers, including those on a band as well as a housing, can collectively span between 60% and 90% of the circumference of the device. Relevant variations discussed elsewhere in this disclosure or in priority-linked disclosures can also be applied to this example.

Figure 8:
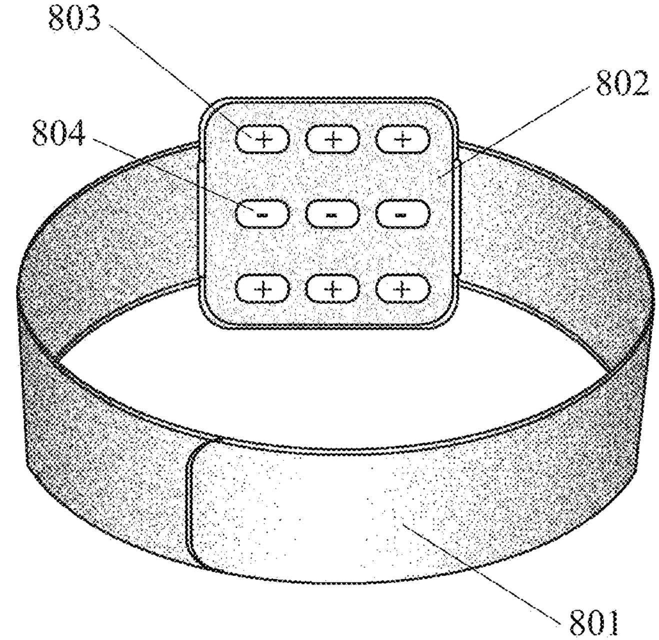
FIG. 8 shows a biometric wearable device with a two-dimensional array of radiowave or microwave energy emitters and receivers which differ in location along circumferential lines and along lines which are perpendicular to circumferential lines, wherein individual emitters and receivers are parallel to circumferential lines, and wherein energy receivers are between energy emitters.

FIG. 8 shows an example of a wearable device for the arm with a plurality of close-fitting biometric sensors comprising: an attachment member 801, such as a strap or band, which is configured to span at least a portion of the circumference of a person's arm; an enclosure 802 which is part of (or attached to) the attachment member; and a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device. This device comprises a two-dimensional array of energy emitters (including 803) and energy receivers (including 804) which is part of a housing (e.g. enclosure) attached to a wearable arcuate band.

In this example, sensors in the two-dimensional sensor array are electromagnetic energy sensors which measure parameters and/or patterns of electromagnetic energy passing through tissue of the person's arm. In this example, there are multiple triads of energy emitters and energy receivers and a triad is aligned along a proximal-to-distal line. In this example, there are two energy emitters and one energy receiver in a triad of energy emitters and energy receivers.

In this example, a longitudinal axis of an individual energy emitter and/or an individual energy receiver is parallel to a circumferential line (e.g. a line around a circumference of the device). In another example, a longitudinal axis of an individual energy emitter and/or an individual energy receiver can be perpendicular and/or orthogonal to a circumferential line. In an example, a device can further comprise energy emitters and/or energy receivers on the arcuate band as well as on the housing. In an example, a circumferential array of energy emitters and energy receivers, including those on a band as well as a housing, can collectively span between 60% and 90% of the circumference of the device. Relevant variations discussed elsewhere in this disclosure or in priority-linked disclosures can also be applied to this example.

Figure 9:
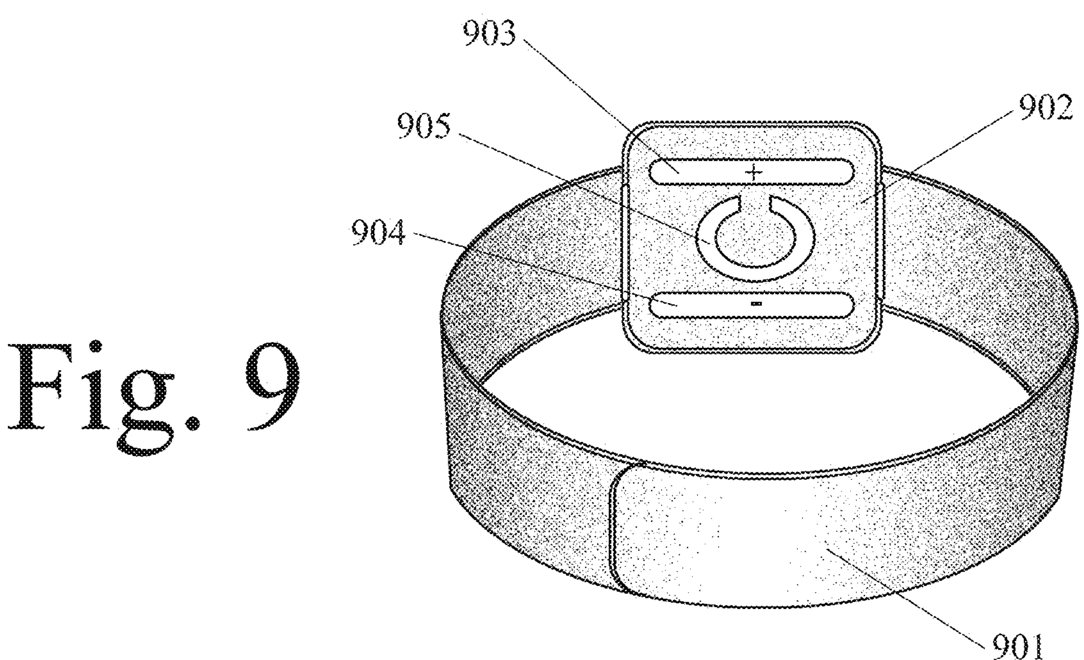
FIG. 9 shows a biometric wearable device with a housing which holds at least one radiowave or microwave energy emitter, at least one energy receiver, and a split ring resonator between the emitter and the receiver, wherein a gap in the circumference of the resonator is on a radial vector which is perpendicular to the longitudinal axis of the emitter and/or the receiver.

FIG. 9 shows an example of an biometric wearable device (e.g. smart watch or arm band) comprising: an arcuate band (e.g. watch strap or band) 901 which is configured to span (some or all of) the circumferential perimeter of a part of a person's body (such as a wrist, arm, finger, ankle, and/or leg); a housing (e.g. smart watch housing) 902 which is held on the person's body by the arcuate band; an energy (e.g. radiowave or microwave) emitter 903 (identified with a plus sign) which is configured to emit energy toward the part of the person's body, wherein the energy emitter is part of (e.g. on or in) the housing; an energy (e.g. radiowave or microwave) receiver 904 (identified with a negative sign) which is configured to receive energy from the energy emitter after that energy has passed through and/or been reflected from the part of the person's body, wherein the energy receiver is part of (e.g. on or in) the housing; and a split ring resonator 905 between the energy emitter and the energy receiver.

In this example, the split and/or gap in the circumference of the spit ring resonator is on a radial vector which is substantially perpendicular to the longitudinal axis of the energy emitter and/or the longitudinal axis of the energy receiver. In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location. Relevant variations discussed elsewhere in this disclosure or in priority-linked disclosures can also be applied to this example.

Figure 10:
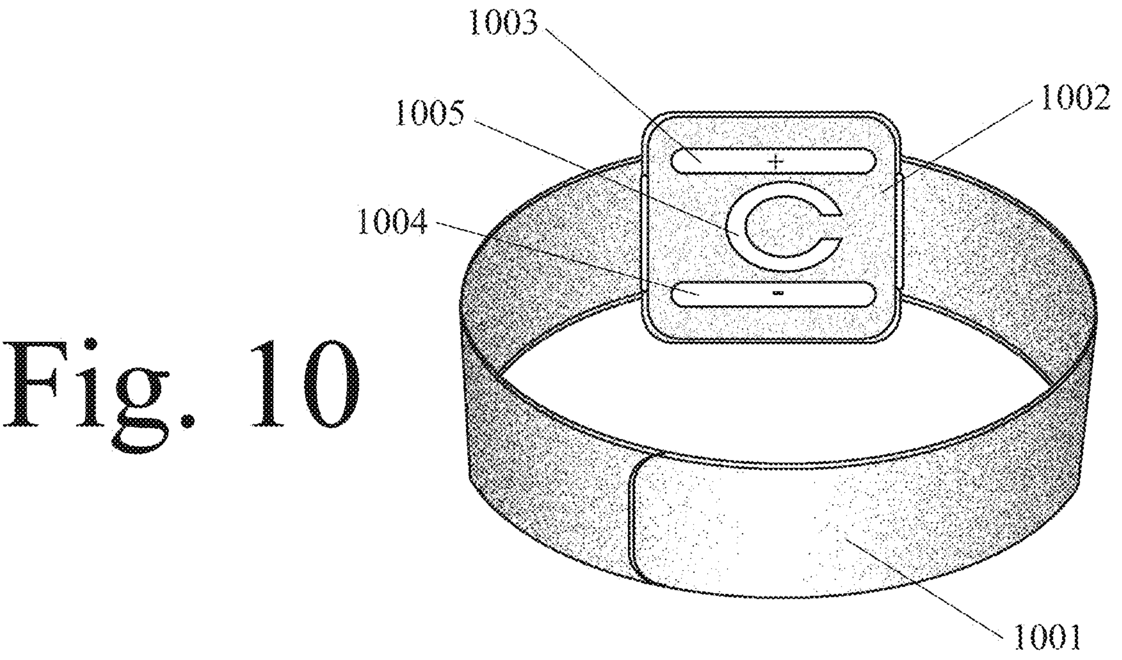
FIG. 10 shows a biometric wearable device with a housing which holds at least one radiowave or microwave energy emitter, at least one energy receiver, and a split ring resonator between the emitter and the receiver, wherein a gap in the circumference of the resonator is on a radial vector which is parallel to the longitudinal axis of the emitter and/or the receiver.

FIG. 10 shows an example of an biometric wearable device (e.g. smart watch or arm band) comprising: an arcuate band (e.g. watch strap or band) 1001 which is configured to span (some or all of) the circumferential perimeter of a part of a person's body (such as a wrist, arm, finger, ankle, and/or leg); a housing 1002 which is held on the person's body by the arcuate band; an energy (e.g. radiowave or microwave) emitter 1003 (identified with a plus sign) which is configured to emit energy toward the part of the person's body, wherein the energy emitter is part of (e.g. on or in) the housing; an energy (e.g. radiowave or microwave) receiver 1004 (identified with a negative sign) which is configured to receive energy from the energy emitter after that energy has passed through and/or been reflected from the part of the person's body, wherein the energy receiver is part of (e.g. on or in) the housing; and a split ring resonator 1005 between the energy emitter and the energy receiver.

In this example, the split and/or gap in the circumference of the spit ring resonator is on a radial vector which is substantially perpendicular to the longitudinal axis of the energy emitter and/or the longitudinal axis of the energy receiver. In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location. Relevant variations discussed elsewhere in this disclosure or in priority-linked disclosures can also be applied to this example.

Figures 11, 12:
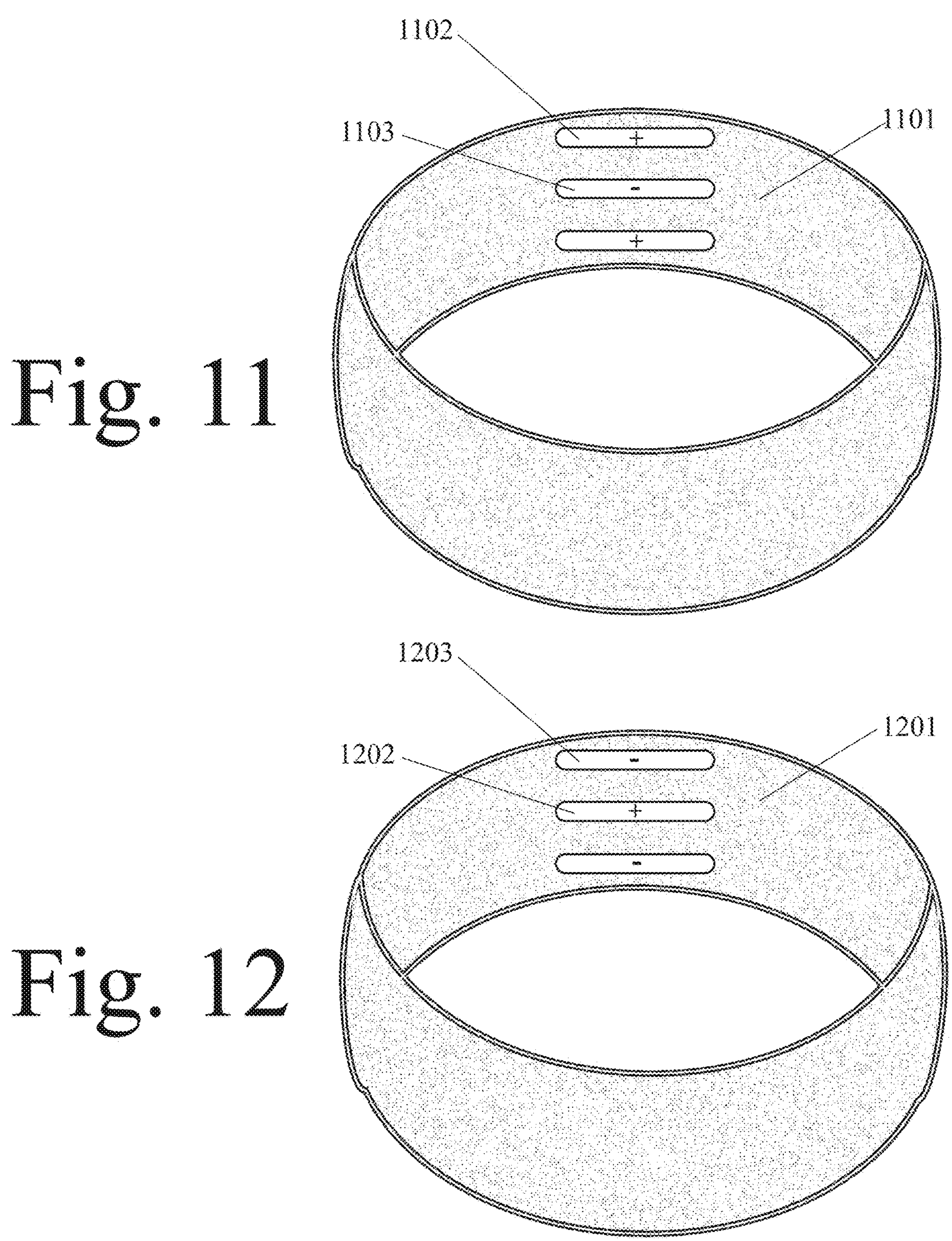
FIG. 11 shows a biometric wearable device with at least one radiowave or microwave energy emitter and at least one energy receiver on an annular band, wherein the emitters and receivers are parallel to each other and to a circumferential line around the device, and wherein an energy receiver is between energy emitters.
FIG. 12 shows a biometric wearable device with at least one radiowave or microwave energy emitter and at least one energy receiver on an annular band, wherein the emitters and receivers are parallel to each other and to a circumferential line around the device, and wherein an energy emitter is between energy receivers.

FIG. 11 shows an example of an biometric wearable device comprising: an arcuate band (e.g. finger ring) 1101 which is configured to span (some or all of) the circumferential perimeter of a part of a person's body (e.g. finger); an energy emitter 1102 (identified with a plus sign) which is configured to emit energy toward the part of the person's body, wherein the energy emitter is on the band; and an energy receiver 1103 (identified with a negative sign) which is configured to receive energy from the energy emitter after that energy has passed through and/or been reflected from the part of the person's body, wherein the energy receiver is on the band.

In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location.

In an example, an electromagnetic energy emitter can emit electromagnetic energy into body tissue and an electromagnetic energy receiver can receive that electromagnetic energy after the electromagnetic energy has passed through the body tissue. In an example, an energy emitter and/or an energy receiver can be an antenna. In an example, an energy emitter can emit radiowave or microwave energy. In an example, an energy emitter and an energy receiver can be co-planar. In an example, an energy emitter and an energy receiver can be parallel. In an example, the longitudinal axis of an energy emitter can be parallel to the longitudinal axis of an energy receiver.

In an example, a finger ring can comprise a circumferential array of energy (e.g. radiowave or microwave) emitters/transmitters and energy (e.g. radiowave or microwave) receivers which collectively span between 60% and 90% of the circumference of the ring. In an example, a finger ring can comprise an alternating circumferential array of energy (e.g. radiowave or microwave) emitters/transmitters and energy (e.g. radiowave or microwave) receivers which collectively span between 60% and 90% of the circumference of the ring. In an example, a finger ring can comprise a circumferential array of sets of energy (e.g. radiowave or microwave) emitters/transmitters and energy (e.g. radiowave or microwave) receivers, wherein each set further comprises an energy emitter between two or more energy receivers.

In an example, a biometric wearable device can be a spectroscopic device which collects information about electromagnetic interaction between energy and body tissue at multiple energy frequencies. In an example, the energy emitter on a biometric wearable device can sweep through a range of energy frequencies. In an example, a biometric wearable device can comprise an array, matrix, or series of antennae with a selected progression of different sizes (e.g. smaller to larger), shapes (e.g. less arcuate to more arcuate), gaps (e.g. closer together to farther apart), material compositions, and/or rotations. In an example, a device can have different size or different shape energy emitters and/or energy receivers. In an example, a device can have nested energy emitters and/or energy receivers.

This figure can also be described as showing an example of a biometric wearable device comprising: an arcuate band (e.g. finger ring) which is configured to span (some or all of) the circumferential perimeter of a part of a person's body (e.g. finger); a first energy emitter (identified with a plus sign) which is configured to emit energy toward the part of the person's body; a second energy emitter (identified with a plus sign) which is configured to emit energy toward the part of the person's body; and an energy receiver (identified with a negative sign) which is configured to receive energy from the first energy emitter and/or the second energy emitter after that energy has passed through and/or been reflected from the part of the person's body, wherein the energy receiver is located between the first energy emitter and the second energy emitter. Relevant variations discussed elsewhere in this disclosure or in priority-linked disclosures can also be applied to this example.

FIG. 12 shows an example of an biometric wearable device comprising: an arcuate band (e.g. finger ring) 1201 which is configured to span (some or all of) the circumferential perimeter of a part of a person's body (e.g. finger); an energy emitter 1202 (identified with a plus sign) which is configured to emit energy toward the part of the person's body, wherein the energy emitter is on the band; and an energy receiver 1203 (identified with a negative sign) which is configured to receive energy from the energy emitter after that energy has passed through and/or been reflected from the part of the person's body, wherein the energy receiver is on the band.

In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location.

In an example, an electromagnetic energy emitter can emit electromagnetic energy into body tissue and an electromagnetic energy receiver can receive that electromagnetic energy after the electromagnetic energy has passed through the body tissue. In an example, an energy emitter and/or an energy receiver can be an antenna. In an example, an energy emitter can emit radiowave or microwave energy. In an example, an energy emitter and an energy receiver can be co-planar. In an example, an energy emitter and an energy receiver can be parallel. In an example, the longitudinal axis of an energy emitter can be parallel to the longitudinal axis of an energy receiver.

In an example, a finger ring can comprise a circumferential array of energy (e.g. radiowave or microwave) emitters/transmitters and energy (e.g. radiowave or microwave) receivers which collectively span between 60% and 90% of the circumference of the ring. In an example, a finger ring can comprise an alternating circumferential array of energy (e.g. radiowave or microwave) emitters/transmitters and energy (e.g. radiowave or microwave) receivers which collectively span between 60% and 90% of the circumference of the ring. In an example, a finger ring can comprise a circumferential array of sets of energy (e.g. radiowave or microwave) emitters/transmitters and energy (e.g. radiowave or microwave) receivers, wherein each set further comprises an energy emitter between two or more energy receivers.

In an example, a biometric wearable device can be a spectroscopic device which collects information about electromagnetic interaction between energy and body tissue at multiple energy frequencies. In an example, the energy emitter on a biometric wearable device can sweep through a range of energy frequencies. In an example, a biometric wearable device can comprise an array, matrix, or series of antennae with a selected progression of different sizes (e.g. smaller to larger), shapes (e.g. less arcuate to more arcuate), gaps (e.g. closer together to farther apart), material compositions, and/or rotations. In an example, a device can have different size or different shape energy emitters and/or energy receivers. In an example, a device can have nested energy emitters and/or energy receivers.

This figure can also be described as showing an example of a biometric wearable device comprising: an arcuate band (e.g. finger ring) which is configured to span (some or all of) the circumferential perimeter of a part of a person's body (e.g. finger); an energy emitter (identified with a plus sign) which is configured to emit energy toward the part of the person's body; a first energy receiver (identified with a negative sign) which is configured to receive energy from the energy emitter after that energy has passed through and/or been reflected from the part of the person's body; a second energy receiver (identified with a negative sign) which is configured to receive energy from the energy emitter after that energy has passed through and/or been reflected from the part of the person's body, wherein the energy emitter is located between the first energy receiver and the second energy receiver. Relevant variations discussed elsewhere in this disclosure or in priority-linked disclosures can also be applied to this example.

Figures 13, 14:
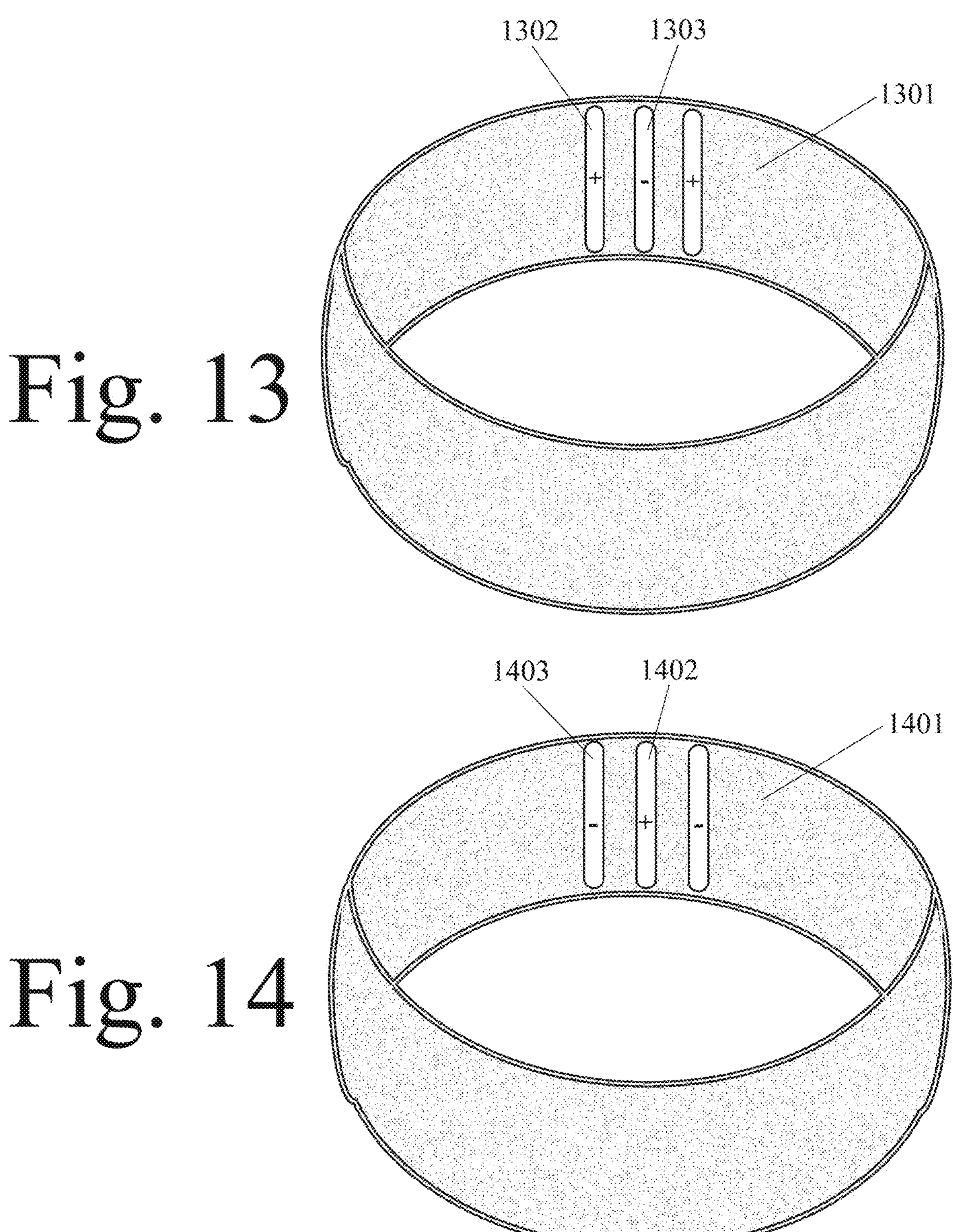
FIG. 13 shows a biometric wearable device with at least one radiowave or microwave energy emitter and at least one energy receiver on an annular band, wherein the emitters and receivers are parallel to each other and perpendicular to a circumferential line around the device, and wherein an energy receiver is between energy emitters.
FIG. 14 shows a biometric wearable device with at least one radiowave or microwave energy emitter and at least one energy receiver on an annular band, wherein the emitters and receivers are parallel to each other and perpendicular to a circumferential line around the device, and wherein an energy emitter is between energy receivers.

FIG. 13 shows an example of an biometric wearable device comprising: an arcuate band (e.g. finger ring) 1301 which is configured to span (some or all of) the circumferential perimeter of a part of a person's body (e.g. finger); an energy emitter 1302 (identified with a plus sign) which is configured to emit energy toward the part of the person's body, wherein the energy emitter is on the band; and an energy receiver 1303 (identified with a negative sign) which is configured to receive energy from the energy emitter after that energy has passed through and/or been reflected from the part of the person's body, wherein the energy receiver is on the band.

In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location.

In an example, an electromagnetic energy emitter can emit electromagnetic energy into body tissue and an electromagnetic energy receiver can receive that electromagnetic energy after the electromagnetic energy has passed through the body tissue. In an example, an energy emitter and/or an energy receiver can be an antenna. In an example, an energy emitter can emit radiowave or microwave energy. In an example, an energy emitter and an energy receiver can be co-planar. In an example, an energy emitter and an energy receiver can be parallel. In an example, the longitudinal axis of an energy emitter can be parallel to the longitudinal axis of an energy receiver.

In an example, a finger ring can comprise a circumferential array of energy (e.g. radiowave or microwave) emitters/transmitters and energy (e.g. radiowave or microwave) receivers which collectively span between 60% and 90% of the circumference of the ring. In an example, a finger ring can comprise an alternating circumferential array of energy (e.g. radiowave or microwave) emitters/transmitters and energy (e.g. radiowave or microwave) receivers which collectively span between 60% and 90% of the circumference of the ring. In an example, a finger ring can comprise a circumferential array of sets of energy (e.g. radiowave or microwave) emitters/transmitters and energy (e.g. radiowave or microwave) receivers, wherein each set further comprises an energy emitter between two or more energy receivers.

In an example, a biometric wearable device can be a spectroscopic device which collects information about electromagnetic interaction between energy and body tissue at multiple energy frequencies. In an example, the energy emitter on a biometric wearable device can sweep through a range of energy frequencies. In an example, a biometric wearable device can comprise an array, matrix, or series of antennae with a selected progression of different sizes (e.g. smaller to larger), shapes (e.g. less arcuate to more arcuate), gaps (e.g. closer together to farther apart), material compositions, and/or rotations. In an example, a device can have different size or different shape energy emitters and/or energy receivers. In an example, a device can have nested energy emitters and/or energy receivers.

This figure can also be described as showing an example of a biometric wearable device comprising: an arcuate band (e.g. finger ring) which is configured to span (some or all of) the circumferential perimeter of a part of a person's body (e.g. finger); a first energy emitter (identified with a plus sign) which is configured to emit energy toward the part of the person's body; a second energy emitter (identified with a plus sign) which is configured to emit energy toward the part of the person's body; and an energy receiver (identified with a negative sign) which is configured to receive energy from the first energy emitter and/or the second energy emitter after that energy has passed through and/or been reflected from the part of the person's body, wherein the energy receiver is located between the first energy emitter and the second energy emitter. Relevant variations discussed elsewhere in this disclosure or in priority-linked disclosures can also be applied to this example.

FIG. 14 shows an example of an biometric wearable device comprising: an arcuate band (e.g. finger ring) 1401 which is configured to span (some or all of) the circumferential perimeter of a part of a person's body (e.g. finger); an energy emitter 1402 (identified with a plus sign) which is configured to emit energy toward the part of the person's body, wherein the energy emitter is on the band; and an energy receiver 1403 (identified with a negative sign) which is configured to receive energy from the energy emitter after that energy has passed through and/or been reflected from the part of the person's body, wherein the energy receiver is on the band.

In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location.

In an example, an electromagnetic energy emitter can emit electromagnetic energy into body tissue and an electromagnetic energy receiver can receive that electromagnetic energy after the electromagnetic energy has passed through the body tissue. In an example, an energy emitter and/or an energy receiver can be an antenna. In an example, an energy emitter can emit radiowave or microwave energy. In an example, an energy emitter and an energy receiver can be co-planar. In an example, an energy emitter and an energy receiver can be parallel. In an example, the longitudinal axis of an energy emitter can be parallel to the longitudinal axis of an energy receiver.

In an example, a finger ring can comprise a circumferential array of energy (e.g. radiowave or microwave) emitters/transmitters and energy (e.g. radiowave or microwave) receivers which collectively span between 60% and 90% of the circumference of the ring. In an example, a finger ring can comprise an alternating circumferential array of energy (e.g. radiowave or microwave) emitters/transmitters and energy (e.g. radiowave or microwave) receivers which collectively span between 60% and 90% of the circumference of the ring. In an example, a finger ring can comprise a circumferential array of sets of energy (e.g. radiowave or microwave) emitters/transmitters and energy (e.g. radiowave or microwave) receivers, wherein each set further comprises an energy emitter between two or more energy receivers.

In an example, a biometric wearable device can be a spectroscopic device which collects information about electromagnetic interaction between energy and body tissue at multiple energy frequencies. In an example, the energy emitter on a biometric wearable device can sweep through a range of energy frequencies. In an example, a biometric wearable device can comprise an array, matrix, or series of antennae with a selected progression of different sizes (e.g. smaller to larger), shapes (e.g. less arcuate to more arcuate), gaps (e.g. closer together to farther apart), material compositions, and/or rotations. In an example, a device can have different size or different shape energy emitters and/or energy receivers. In an example, a device can have nested energy emitters and/or energy receivers.

This figure can also be described as showing an example of a biometric wearable device comprising: an arcuate band (e.g. finger ring) which is configured to span (some or all of) the circumferential perimeter of a part of a person's body (e.g. finger); an energy emitter (identified with a plus sign) which is configured to emit energy toward the part of the person's body; a first energy receiver (identified with a negative sign) which is configured to receive energy from the energy emitter after that energy has passed through and/or been reflected from the part of the person's body; a second energy receiver (identified with a negative sign) which is configured to receive energy from the energy emitter after that energy has passed through and/or been reflected from the part of the person's body, wherein the energy emitter is located between the first energy receiver and the second energy receiver. Relevant variations discussed elsewhere in this disclosure or in priority-linked disclosures can also be applied to this example.

FIG. 15 shows an example of a biometric wearable device with a plurality of close-fitting biometric sensors comprising: an annular band 1501, such as a finger ring, which is configured to span at least a portion of the circumference of a person's finger; and a two-dimensional sensor array which is part of the annular band, wherein sensors in this two-dimensional array differ in location along a portion of the circumference of the band, and wherein sensors in this two-dimensional array differ in location along axes which are perpendicular to the circumference of the band. This device comprises a two-dimensional array of energy emitters (including 1502) and energy receivers (including 1503) which is part of the band.

In this example, sensors in the two-dimensional sensor array are electromagnetic energy sensors which measure parameters and/or patterns of electromagnetic energy passing through tissue of the person's finger. In this example, there are multiple triads of energy emitters and energy receivers and a triad is aligned along a proximal-to-distal line. In this example, there is one energy emitter and two energy receivers in a triad of energy emitters and energy receivers.

In an example, a finger ring can comprise a circumferential array of energy (e.g. radiowave or microwave) emitters/transmitters and energy (e.g. radiowave or microwave) receivers which collectively span between 60% and 90% of the circumference of the ring. In an example, a finger ring can comprise an alternating circumferential array of energy (e.g. radiowave or microwave) emitters/transmitters and energy (e.g. radiowave or microwave) receivers which collectively span between 60% and 90% of the circumference of the ring. In an example, a finger ring can comprise a circumferential array of sets of energy (e.g. radiowave or microwave) emitters/transmitters and energy (e.g. radiowave or microwave) receivers, wherein each set further comprises an energy emitter between two or more energy receivers. Relevant variations discussed elsewhere in this disclosure or in priority-linked disclosures can also be applied to this example.

FIG. 16 shows an example of a biometric wearable device with a plurality of close-fitting biometric sensors comprising: an annular band 1601, such as a finger ring, which is configured to span at least a portion of the circumference of a person's finger; and a two-dimensional sensor array which is part of the annular band, wherein sensors in this two-dimensional array differ in location along a portion of the circumference of the band, and wherein sensors in this two-dimensional array differ in location along axes which are perpendicular to the circumference of the band. This device comprises a two-dimensional array of energy emitters (including 1602) and energy receivers (including 1603) which is part of the band.

In this example, sensors in the two-dimensional sensor array are electromagnetic energy sensors which measure parameters and/or patterns of electromagnetic energy passing through tissue of the person's finger. In this example, there are multiple triads of energy emitters and energy receivers and a triad is aligned along a proximal-to-distal line. In this example, there are two energy emitters and one energy receiver in a triad of energy emitters and energy receivers.

In an example, a finger ring can comprise a circumferential array of energy (e.g. radiowave or microwave) emitters/transmitters and energy (e.g. radiowave or microwave) receivers which collectively span between 60% and 90% of the circumference of the ring. In an example, a finger ring can comprise an alternating circumferential array of energy (e.g. radiowave or microwave) emitters/transmitters and energy (e.g. radiowave or microwave) receivers which collectively span between 60% and 90% of the circumference of the ring. In an example, a finger ring can comprise a circumferential array of sets of energy (e.g. radiowave or microwave) emitters/transmitters and energy (e.g. radiowave or microwave) receivers, wherein each set further comprises an energy emitter between two or more energy receivers. Relevant variations discussed elsewhere in this disclosure or in priority-linked disclosures can also be applied to this example.

FIG. 17 shows an example of a biometric wearable device with a plurality of close-fitting biometric sensors comprising: an annular band 1701, such as a finger ring, which is configured to span at least a portion of the circumference of a person's finger; and a two-dimensional sensor array which is part of the annular band, wherein sensors in this two-dimensional array differ in location along a portion of the circumference of the band, and wherein sensors in this two-dimensional array differ in location along axes which are perpendicular to the circumference of the band. This device comprises a two-dimensional array of energy emitters (including 1702) and energy receivers (including 1703) which is part of the band.

In this example, sensors in the two-dimensional sensor array are electromagnetic energy sensors which measure parameters and/or patterns of electromagnetic energy passing through tissue of the person's finger. In this example, there are multiple triads of energy emitters and energy receivers and a triad is aligned along a proximal-to-distal line. In this example, there is one energy emitter and two energy receivers in a triad of energy emitters and energy receivers.

In an example, a finger ring can comprise a circumferential array of energy (e.g. radiowave or microwave) emitters/transmitters and energy (e.g. radiowave or microwave) receivers which collectively span between 60% and 90% of the circumference of the ring. In an example, a finger ring can comprise an alternating circumferential array of energy (e.g. radiowave or microwave) emitters/transmitters and energy (e.g. radiowave or microwave) receivers which collectively span between 60% and 90% of the circumference of the ring. In an example, a finger ring can comprise a circumferential array of sets of energy (e.g. radiowave or microwave) emitters/transmitters and energy (e.g. radiowave or microwave) receivers, wherein each set further comprises an energy emitter between two or more energy receivers. Relevant variations discussed elsewhere in this disclosure or in priority-linked disclosures can also be applied to this example.

FIG. 18 shows an example of a biometric wearable device with a plurality of close-fitting biometric sensors comprising: an annular band 1801, such as a finger ring, which is configured to span at least a portion of the circumference of a person's finger; and a two-dimensional sensor array which is part of the annular band, wherein sensors in this two-dimensional array differ in location along a portion of the circumference of the band, and wherein sensors in this two-dimensional array differ in location along axes which are perpendicular to the circumference of the band. This device comprises a two-dimensional array of energy emitters (including 1802) and energy receivers (including 1803) which is part of the band. In this example, sensors in the two-dimensional sensor array are electromagnetic energy sensors which measure parameters and/or patterns of electromagnetic energy passing through tissue of the person's finger. In this example, there are multiple triads of energy emitters and energy receivers and a triad is aligned along a proximal-to-distal line. In this example, there are two energy emitters and one energy receiver in a triad of energy emitters and energy receivers.

In an example, a finger ring can comprise a circumferential array of energy (e.g. radiowave or microwave) emitters/transmitters and energy (e.g. radiowave or microwave) receivers which collectively span between 60% and 90% of the circumference of the ring. In an example, a finger ring can comprise an alternating circumferential array of energy (e.g. radiowave or microwave) emitters/transmitters and energy (e.g. radiowave or microwave) receivers which collectively span between 60% and 90% of the circumference of the ring. In an example, a finger ring can comprise a circumferential array of sets of energy (e.g. radiowave or microwave) emitters/transmitters and energy (e.g. radiowave or microwave) receivers, wherein each set further comprises an energy emitter between two or more energy receivers. Relevant variations discussed elsewhere in this disclosure or in priority-linked disclosures can also be applied to this example.

FIG. 19 shows an example of a biometric wearable device comprising: an arcuate band (e.g. finger ring) 1901 which is configured to span (some or all of) the circumferential perimeter of a part of a person's body (e.g. finger); an energy (e.g. radiowave or microwave) emitter 1903 (identified with a plus sign) which is configured to emit energy toward the part of the person's body, wherein the energy emitter is on the band; an energy (e.g. radiowave or microwave) receiver 1903 (identified with a negative sign) which is configured to receive energy from the energy emitter after that energy has passed through and/or been reflected from the part of the person's body, wherein the energy receiver is on the band; and a split ring resonator 1904 between the energy emitter and the energy receiver.

In this example, the split and/or gap in the circumference of the spit ring resonator is on a radial vector which is substantially perpendicular to the longitudinal axis of the energy emitter and/or the longitudinal axis of the energy receiver. In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location. Relevant variations discussed elsewhere in this disclosure or in priority-linked disclosures can also be applied to this example.

FIG. 20 shows an example of an biometric wearable device comprising: an arcuate band (e.g. finger ring) 2001 which is configured to span (some or all of) the circumferential perimeter of a part of a person's body (e.g. finger); an energy (e.g. radiowave or microwave) emitter 2002 (identified with a plus sign) which is configured to emit energy toward the part of the person's body, wherein the energy emitter is on the band; an energy (e.g. radiowave or microwave) receiver 2003 (identified with a negative sign) which is configured to receive energy from the energy emitter after that energy has passed through and/or been reflected from the part of the person's body, wherein the energy receiver is on the band; and a split ring resonator 2004 between the energy emitter and the energy receiver.

In this example, the split and/or gap in the circumference of the spit ring resonator is on a radial vector which is substantially perpendicular to the longitudinal axis of the energy emitter and/or the longitudinal axis of the energy receiver. In an example, this device can further comprise: a data processor which receives data from the energy receiver which is analyzed in order to measure a biometric parameter level (e.g. body oxygenation, hydration, or glucose level); an energy source which provides power to the energy emitter and/or to the data processor; and a data transmitter which transmits data from the data processor to a remote device and/or location. Relevant variations discussed elsewhere in this disclosure or in priority-linked disclosures can also be applied to this example.

I claim:

1. A biometric wearable device comprising:

an arcuate band which is configured to span at least part of the circumference of a body member;

a housing which is held on the body member by the arcuate band;

an energy emitter on the housing;

an energy receiver on the housing which is configured to receive energy from the energy emitter after that energy has passed through and/or been reflected from the body member, wherein a connector line is defined as a straight line between the energy emitter and the energy receiver; and;

a split ring resonator between the energy emitter and the energy receiver, wherein a resonant frequency of the resonator is changed by a change in a permittivity of tissue or fluid in the body member, wherein compass coordinates are defined around the resonator so that the connector line intersects 270-degree and the 90-degree compass coordinates, and wherein there is a gap in the resonator at a 360-degree compass coordinate.

2. The device in claim 1 wherein the device is embodied as a smart watch, wrist band, arm band, or finger ring.

3. The device in claim 1 wherein the body member is a wrist, arm, or finger.

4. The device in claim 1 wherein data from the energy receiver is analyzed in order to measure a biometric parameter level selected from the group consisting of: oxygenation level, hydration level, or glucose level.

5. The device in claim 1 wherein the energy emitter and/or the energy receiver comprises an antenna.

6. The device in claim 1 wherein the energy emitter emits electromagnetic energy with a frequency in the radio wave range.

7. The device in claim 1 wherein the energy emitter emits electromagnetic energy with a frequency in the microwave range.

8. The device in claim 1 wherein the energy emitter emits electromagnetic energy which sweeps through a range of frequencies.

9. The device in claim 1 wherein the energy emitter and the energy receiver are coplanar.

10. The device in claim 1 wherein the energy emitter and the energy receiver are parallel.

11. The device in claim 1 wherein the longitudinal axis of the energy emitter is parallel to the longitudinal axis of the energy receiver.

12. The device in claim 1 wherein the device comprises an array, matrix, or series of antennae having different sizes, different shapes, different gaps, and/or different rotations.

* * * * *